US009181530B2

(12) United States Patent
Emerson et al.

(10) Patent No.: US 9,181,530 B2
(45) Date of Patent: Nov. 10, 2015

(54) INFECTIOUS HEPATITIS E VIRUS GENOTYPE 3 RECOMBINANTS

(75) Inventors: Suzanne U. Emerson, Gaithersburg, MD (US); Priyanka Shukla, Mumbai (IN); Hanh T. Nguyen, Lanham, MD (US); Robert H. Purcell, Gaithersburg, MD (US); Harry R. Dalton, Bodmin (GB); Richard Bendall, Cornwall (GB)

(73) Assignees: The United States of America, as represented by the Secretary, Department of Health and Human Services, Washington, DC (US); Royal Cornwall Hospital Trust, Cornwall (GB)

( * ) Notice: Subject to any disclaimer, the term of this patent is extended or adjusted under 35 U.S.C. 154(b) by 27 days.

(21) Appl. No.: 13/978,839

(22) PCT Filed: Jan. 10, 2012

(86) PCT No.: PCT/US2012/020830
§ 371 (c)(1),
(2), (4) Date: Jul. 9, 2013

(87) PCT Pub. No.: WO2012/096999
PCT Pub. Date: Jul. 19, 2012

(65) Prior Publication Data
US 2013/0302790 A1    Nov. 14, 2013

Related U.S. Application Data

(60) Provisional application No. 61/431,377, filed on Jan. 10, 2011, provisional application No. 61/554,323, filed on Nov. 1, 2011.

(51) Int. Cl.
| | |
|---|---|
| A61K 39/29 | (2006.01) |
| A61K 39/12 | (2006.01) |
| C07H 21/00 | (2006.01) |
| C12N 7/00 | (2006.01) |
| C12N 15/86 | (2006.01) |
| C12Q 1/70 | (2006.01) |
| C07K 14/005 | (2006.01) |
| A61K 39/00 | (2006.01) |

(52) U.S. Cl.
CPC ............. *C12N 7/00* (2013.01); *C07K 14/005* (2013.01); *C12N 15/86* (2013.01); *C12Q 1/707* (2013.01); *A61K 39/00* (2013.01); *C12N 2770/28121* (2013.01); *C12N 2770/28122* (2013.01); *C12N 2770/28143* (2013.01); *C12N 2770/28151* (2013.01)

(58) Field of Classification Search
None
See application file for complete search history.

(56) References Cited

U.S. PATENT DOCUMENTS

| 7,084,266 B1 | 8/2006 | Yanagi et al. |
| 2003/0049601 A1 | 3/2003 | Schlauder et al. |
| 2010/0034845 A1 | 2/2010 | Meng et al. |

OTHER PUBLICATIONS

Pudupakam et al., Journal of Virology, Jan. 2009, 83(1):384-395.*
Shukla et al., Journal of Virology, 2012, pp. 5697-5707.*
Legrand-Abravanel et al., Emerging Infectious Diseases, 2009, 15(1):110-114.*
Dalton HR, et al., "Persistent carriage of hepatitis E virus in patients with HIV infection," *N Engl J Med*, 2009, pp. 1025-1027, vol. 361.
Huang, Y., et al., "Capped RNA Transcripts of Full-Length cDNA Clones of Swine Hepatitis E Virus Are Replication Competent When Transfected Into Huh7 Cells and Infection When Intrahepatically Inoculated into Pigs," *Journal of Virology*, 2005, pp. 1552-1558, vol. 79(3).
Okamoto, H., "Genetic variability and evolution of hepatitis E virus," *Virus Research*, 2007, pp. 216-228, vol. 127.
Shukla, P., et al., "Cross-species infections of cultured cells by hepatitis E virus and discovery of an infectious virus-host recombinant," *Proc. Natl. Acad. Sci.*, 2011, pp. 2438-2443, vol. 108(6).
Trueb, B., et al., "Sequence of a cDNA clone encoding chicken ribosomal protein S17," *Nucleic Acids Research*, 1988, p. 4723, vol. 16(10).
International Search Report for PCT/US2012/020830 mailed May 1, 2012, 6 pgs.
Written Opinion for PCT/US2012/020830 mailed May 1, 2012, 5 pgs.
Shukla et al., "Adpatation of a Genotype 3 Hepatitis E Virus to Efficient Growth in Cell Culture Depends on an Inserted Human Gene Segment Acquired by Recombination", *Journal of Virology*, vol. 86, No. 10, pp. 5697-5707 (2012).
Tanaka et al., "Development and Characterization of a Genotype 4 Hepatitis E Virus Cell Culture System Using a HE-JF5/15F Strain Recovered from a Fulminant Hepatitis Patient", *J Clin Microbiol*, vol. 47, No. 6, pp. 1906-1910 (2009).
Yamada et al., "Construction of an infectious cDNA clone of hepatitis E virus strain JE03-1760F that can propagate efficiently in culture cells" *Journal of General Virology*, vol. 90, pp. 457-462 (2009).
Extended European Search Report dated Aug. 8, 2014 for EP Application No. 12734409.1, 6 pages.

* cited by examiner

*Primary Examiner* — Stacy B Chen
(74) *Attorney, Agent, or Firm* — Kilpatrick Townsend & Stockton LLP

(57) ABSTRACT

The invention relates to the discovery of an HEV strain from a chronically infected patient. The virus grow unusually well in numerous cell cultures. Thus, the invention provides cell cultures, vectors, and vaccine compositions based on the virus. The invention relates, in part, on the identification of a new strain of HEV genotype 3 virus. Strain Kernow-C1 (genotype 3) of HEV, which was isolated from a chronically infected patient, was used to identify human, pig and deer cell lines permissive for infection. Adaptation of the Kernow-C 1 strain to growth in human hepatoma cells selected for a rare virus recombinant that contained an insertion of 174 ribonucleotides (58 amino acids) of a human ribosomal protein gene and additional mutations.

19 Claims, 13 Drawing Sheets

A  (HEV) 2267 CGAGGAGTGCTACACGCGGCTGGGCAACGACTTCCACACGAACAAGCGCGTGTGCGAGGAGATCGCCAT
              ||||||||||||||||||||||||||||||||||||||||||||||||||||||||||||||||||||
     (S17) 76 CTACACGCGGCTGGGCAACGACTTCCACACGAACAAGCGCGTGTGCGAGGAGATCGCCAT 135

TATCCCTAGCAAAAAGCCCCGCAACAAGATGGCAGGTTATGTCACGCATCTGATGAAGCG 122
              ||||| *||||||||||||||||||||||||| *||||||||||||||||||||||||||
          136 TATCCCCAGCAAAAAGCTCCGCAACAAGATAGCAGGTTATGTCACGCATCTGATGAAGCG 195

AATTCAGAGAGGCCCAGTAAGAGGTATCTCCATCAAGCTGCAGGAGGAGGCTCAGGTTCG 2283
              |||||||||||||||||||||||||||||||||||||||||||||||||||||||||| |
          196 AATTCAGAGAGGCCCAGTAAGAGGTATCTCTATCAAGCTGCAGGAGGAGG 245

B  (HEV) ALPPPSEECYTRLGNDFHTNKRVCEEIAIIPSKKPRNKMAGYVTHLMKRIQRGPVRGISIKLQEEAQVDAASV
         |||||||||||||||||||||||||||| |||| |||| ||||||||||||||||||||||
   (S17) 21 YTRLGNDFHTNKRVCEEIAIIPSKKLRNKIAGYVTHLMKRIQRGPVRGISIKLQE 75

SEQUENCE LISTING

<160> NUMBER OF SEQ ID NOS: 14

<210> SEQ ID NO 1
<211> LENGTH: 7430
<212> TYPE: DNA
<213> ORGANISM: Hepatitis E virus
<220> FEATURE:
<223> OTHER INFORMATION: Hepatitis E virus Kernow genotype 3 replicating
      variant

<400> SEQUENCE: 1

```
ggcagaccac gtatgtggtc gatgccatgg aggcccacca gttcattaag gctcctggca      60
ttactactgc cattgagcag gctgctctgg ctgcggccaa ttccgccttg gcgaatgctg     120
tggtggttcg gccgttttta tcccgtctac aaaccgagat tcttatcaat ttgatgcaac     180
cccggcagtt ggttttccgc cctgaagtgc tttggaatca tcctatccag cgggttatac     240
acaatgaact agaacagtac tgccgggccc gtgctggccg ctgtttggag gtcggagccc     300
atccgagatc tattaatgat aaccccaacg tcttgcaccg tgtttccttt agaccggttg     360
gcagggatgt tcagcgctgg tactctgccc ccacccgtgg ccctgcggcc aattgccgcc     420
gctccgcgct gcgtggcctc cccccgttg accgcaccta ctgttttgat ggattctccc     480
gttgtgcttt tgctgcagag accggtgtgg ccctttactc tttgcatgac ctttggccag     540
ctgatgttgc agaggcgatg gcccgtcatg gatgacacg gttgtatgcc gcactacatc     600
ttccccctga ggtgctgcta ccacccggca cctatcacac aacttcgtat ctcctgattc     660
acgacggcga tcgcgccgtt gtaacctatg agggcgatac cagtgcgggc tataaccatg     720
atgtttccat acttcgtgcg tggatccgta ctactaaaat agttggtgac cacccgttgg     780
ttatagagcg tgtgcgggcc attggttgtc atttcgtgct gttgctcacc gcggcccctg     840
agccgtcacc tatgccttat gtcccctacc ctcgttcaac ggaggtgtat gttcggtcta     900
tatttgcccc tggcggctct ccatctttgt ttccgtcagc ctgctctact aaatctacct     960
tccacgctgt cccggtccat atctgggatc ggctcatgct ctttggtgcc acctggatg    1020
```

```
atcaggcgtt ctgttgttca cgactcatga cttacctccg tggtattagc tacaaggtca    1080
ctgttggtgc gcttgttgct aatgaggggt ggaacgcctc tgaagatgct cttactgcag    1140
tgatcactgc ggcttatctg actatctgcc atcagcgcta cctccgtacc caggcgatat    1200
ccaagggcat gcgccggttg gaggttgagc atgcccagaa atttatcaca agactctaca    1260
gttggctatt tgagaagtct ggccgtgatt acatccccgg ccgccagctc cagttttatg    1320
cacagtgccg acggtggcta tctgcaggat ccatctgga ccccagggtg cttgtttttg     1380
atgaatcagt gccatgtcgt gtaggacgt tcctgaagaa agtcgcgggt aaattctgct     1440
gttttatgcg gtggttaggg caggagtgca cctgcttcct ggagccagcc gagggtttag    1500
ttggcgacca tggccatgac aatgaggctt atgaaggttc tgaggtcgac caggctgaac    1560
ctgcccatct tgatgtttcg ggacttatg ccgtccacgg caccagctt gtagccctct      1620
atagggcact taatgtccca catgatattg ccgctcgagc ttcccgatta acggctactg    1680
ttgagcttgt tgcaggtcca gaccgcttgg agtgccgcac tgtgctcggt aataagacct    1740
tccggacgac ggtggttgat ggcgcccatc ttgaagcgaa tgcccagag cagtatgtcc     1800
tgtcatttga cgcctcccgt cagtctatgg gggcgggtc gcacaacctc acttatgagc     1860
tcaccctgc cggtttgcag gttaggatct catctaacgg tctggattgc actgctacat     1920
tccccccgg cggtgcccct agcgccgcgc caggggaggt ggcagccttc tgtgctgccc     1980
tttacagata taacaggttc acccagcggc actcgctgac cggtggacta tggttacacc    2040
ctgagggatt gctgggtatc ttccctccat tctcccctgg gcatatctgg gagtctgcta    2100
accccttttg cggggagggg actttgtata cccggacctg gtcaacatct ggcttttcta    2160
gtgatttctc tcccctgag gcggccgccc ctgcttcggc tgctgcccg gggctgcccc      2220
accctacccc gcctgctagt gatatttggg cgttaccacc gccctccgag gagtgctaca    2280
cgcgcctggg caacgacttc cacacgaaca agcgcgtgtg cgaggagatc gccattatcc    2340
ctagcaaaaa gccccgcaac aagatggcag gttatgtcac gcatctgatg aagcgaattc    2400
agagaggccc agtaagaggt atctccatca agctgcagga ggaggctcag gtcgatgcag    2460
catctgtgcc ccttaccctc gtgcctgctg ggtcgcccag ccctgttgtg tcaccttccc    2520
ccccccccc tccccccgtg cgtaagccat caacaccccc gccttctcgt acccgtcgcc     2580
tcctctacac ctaccccgac ggcgctaagg tgtatgcagg gtcattgttt gaatcagact    2640
gtgattggct ggttaacgcc tcaaacccgg gccatcgccc tggaggtggc ctctgtcatg    2700
cctttcatca acgttttccg gaggcgtttt atccgactga attcattatg cgtgagggcc    2760
tagcggcata caccctgacc ccgcgcccta tcatccacgc agtggcgccc gactacaggg    2820
ttgagcagaa cccgaagagg ctcgaggcag cgtaccggga aacttgctcc cgtcgtggca    2880
ccgctgctta cccgctttta ggctcgggca tataccaggt ccctgtcagc ctcagttttg    2940
atgcctggga acgcaatcat cgccccggcg atgagcttta cttgactgag cccgctgcgg    3000
cttggtttga ggctaataag ccggcgcagc cggcgcttac cataactgag gatacggctc    3060
gtacggccag cctggcatta gagatcgacg ccgctacaga ggttggccgt gcttgtgccg    3120
gctgcactat cagtcctggg attgtgcact atcagtttac cgctgggtc ccgggctcgg     3180
gcaagtcaag gtccatacaw cagggagatg ttgatgtggt ggttgtgccc acccgggagc    3240
tccgtaacag ttggcgccgc cggggtttcg cggctttcac acctcacaca gcggccgtg    3300
ttactaacgg ccgccgcgtt gtgattgatg aggcccatc tctcccgcca cacctgttgc     3360
tgctacatat gcagcgggcc tcctcggtcc acctactcgg tgacccaaat cagatccctg    3420
```

```
ctatcgattt tgaacacgcc ggcctggtcc ccgcgatccg ccccgagctt gcaccaacga   3480
gctggtggca cgtcacacac cgttgcccgg ccgatgtgtg cgaactcata cgcggggcct   3540
accccaaaat ccagaccacg agccgtgtgc tacggtccct gttttggaat gaaccggcta   3600
tcggccagaa gttggttttty acgcaggctg ccaaggccgc taaccctggt gcgattacgg   3660
ttcacgaagc tcagggtgcc accttcactg agaccacagt tatagccacg gccgacgcca   3720
ggggcctcat tcagtcatcc cgggcccatg ctatagttgc acttacccgc cacaccgaga   3780
agtgcgtcat tttggatgct cccggcctgc tgcgtgaagt sggtatctcg gatgtgattg   3840
tcaataattt tttccttgca ggcggagagg tcggccatca ccgcccttct gtgatacccc   3900
gcggtaaccc cgatcagaac ctcgggactt tacaagcctt cccgccgtcc tgccagatta   3960
gtgcttacca ccagctggct gaggaattag gccatcgccc tgccctgtt gccgccgtct   4020 tgccccttg ccccgagctt gagcagggcc tgctttacat gccacaagag cttaccgtgt   4080
ctgatagtgt gctggttttt gagcttacgg acatagtcca ctgccgcatg gccgctccaa   4140
gccagcgaaa ggctgttctt tcaacacttg tggggcggta tggccgtagg acgaagttat   4200
atgaggcagc acattcagat gtccgtgagt ccctagccag gttcatcccc actatcgggc   4260
ccgttcaggc caccacatgt gagttgtatg agttggttga ggccatggtg gagaagggtc   4320
aggacgggtc agccgtctta gagctagatc tctgcaatcg tgatgtctcg cgcatcacat   4380
ttttccaaaa ggattgcaac aagtttacaa ctggtgagac tattgcccat ggcaaggttg   4440
gtcagggtat atcggcctgg agcaagacct tctgcgcttt gtttggcccg tggttccgtg   4500
ccattgagaa agaaatactg gccctgctcc cgcctaatgt cttttatggc gatgcttatg   4560
aggagtcagt gcttgctgcc gctgtgtcag gggcggggtc atgcatggta tttgaaaatg   4620
acttttcgga gtttgatagc acccagaaca acttctctct cggccttgag tgtgtggtta   4680
tggaggagtg cggcatgcct caatggttaa ttaggttgta tcacctggta cggtcagcct   4740
ggattctgca ggcgccaaag gagtctctta agggtttctg gaagaagcat tctggtgagc   4800
ccggtaccct tctttggaac accgtttgga acatggcaat catagcacat tgctacgagt   4860
tccgtgactt tcgtgttgct gcctttaagg gtgatgattc ggtggtcctc tgtagcgact   4920
accggcagag ccgcaatgcg gcagctttga ttgctggctg tgggcttaaa ttgaaggttg   4980
actatcgccc cattgggctg tatgctgggg tggtggtggc ccctggcttg gggacactgc   5040
ctgatgtggt gcgttttgct ggtcggctgt ctgaaaagaa ttggggcccc ggcccggaac   5100
gtgctgagca gctacgtctt gctgtttgtg atttccttcg aggggttgacg aacgttgcgc   5160 aggtctgtgt tgatgttgtg tcccgtgtct atggagttag ccccgggctg gtacataacc   5220
ttattggcat gttgcagacc attgccgatg gcaaggccca cttacagag actattaaac   5280 ctgttcttga tcttacaaat tccatcatac agcgggtaga atgaataaca tgtttgttgc   5340 atcgccatg ggatcaccat gtgccctagg gttgttctgc tgctgttctt cgtgtttctg   5400
cctatgctgc ccgcgccacc ggccggccag ccgtctggcc gtcgtcgtgg gcggcgcagc   5460
ggcggtgccg gcggtggttt ctggggtgac agggttgatt ctcagccctt cgccctcccc   5520
tatattcatc caaccaaccc cttcgccgcc gatatcgttt cacaatccgg ggctggaact   5580
cgccctcggc agccgccccg cccccttggc tccgcttggc gtgaccagtc ccagcgcccc   5640
tccgctgccc ccgccgtcg atctgcccca gctgggggtg cgccgttgac tgctgtatca   5700
ccagcccctg acacagcccc tgtacctgat gttgattcac gtggtgctat tctgcgtcgg   5760
```

```
cagtataatt tgtccacgtc cccgctcacg tcatctgttg cttcgggtac caatttggtt      5820
ctctacgctg ccccgctaaa tcccctcttg cccctccagg atggcaccaa cacccatatc      5880
atggctactg aggcatccaa ctatgctcag taccgggtcg ttcgagctac gatccgctac      5940
cgcccgctgg tgccgaatgc tgttggtggt tatgctattt ctatttcttt ttggcctcaa      6000
actacaacta cccctacttc tgttgatatg aattctatta cttccactga tgttaggatt      6060
ttggtccagc ccgtattgc ctccgagtta gtcatcccta gtgagcgcct tcattatcgc       6120
aatcaaggct ggcgctctgt tgagaccaca ggtgtggctg aggaggaggc tacctccggt      6180
ctggtaatgc tttgcattca tggctctcct gttaactctt atactaatac accttacact      6240
ggtgcgttgg ggctccttga ttttgcacta gagcttgaat tcaggaattt gacacccggg      6300
aacaccaaca cccgtgtttc ccggtatacc agcacagccc gtcatcggtt gcgccgcgt      6360 gctgatggga ccgctgagct tactaccaca gcagccacac gatttatgaa ggatctgcat      6420
ttcactggca ctaatggcgt tggtgaggtg ggtcgcggta tcgccctgac actgttcaat      6480
cttgctgata cgcttctagg tggtttaccg acagaattga tttcgtcggc tgggggtcag      6540
ttgttctact cccgcccctgt tgtctcggcc aatggcgagc cgacagtgaa gttatacaca      6600
tctgtggaga atgcgcagca agacaagggc attaccatcc cacacgatat agatttgggt      6660
gactcccgtg tggttattca ggattatgat aatcagcacg agcaagaccg acccacgccg      6720
tcacctgccc cctcacgccc tttctcagtc cttcgcgcta acgatgtttt gtggctctcc      6780
ctcactgccg ctgagtacga tcaggctacg tatgggtcgt ctaccaaccc tatgtatgtc      6840
tctgatacag ttacctttgt caatgtggcc actggtgctc aggctgttgc ccgctctctt      6900
gattggtcta aagttacttt ggatggtcgc ccccttacta ccattcagca gtattctaag      6960
acattttatg ttctcccgct ccgcgggaag ctgtcctttt gggaggctgg cacaactagg      7020
gccggctacc catataacta taacaccact gctagtgatc aaattctgat tgagaatgcg      7080 gccgccatc gtgtcgctat ctccacctac actaccagcc tgggtgccgg ccctacctcg      7140
atctccgcgg tgggtgtatt agccccacac tcggcccttg ctgttcttga ggacactgtt      7200
gattaccctg ctcgtgctca cacttttgat gatttctgcc cggagtgtcg tacccctaggt      7260 ttgcagggtt gtgcattcca gtccactatt gctgagcttc agcgccttaa aacggaggta      7320
ggcaaaaccc gggagtctta attaattcct tccgtgcccc cttcgcagtc ttccttttgg      7380
ctttatttct tatttctgct ttccgcgctc cctggaaaaa aaaaaaaaaa                 7430
```

<210> SEQ ID NO 2
<211> LENGTH: 1765
<212> TYPE: PRT
<213> ORGANISM: Hepatitis E virus
<220> FEATURE:
<223> OTHER INFORMATION: Hepatitis E virus Kernow genotype 3 replicating
      variant ORF1, including insertion in hypervariable region
<220> FEATURE:
<221> NAME/KEY: SITE
<222> LOCATION: (750)..(807)
<223> OTHER INFORMATION: insertion in hypervariable region
<220> FEATURE:
<221> NAME/KEY: VARIANT
<222> LOCATION: 1058
<223> OTHER INFORMATION: Xaa = Gln or His

<400> SEQUENCE: 2

Met Glu Ala His Gln Phe Ile Lys Ala Pro Gly Ile Thr Thr Ala Ile
 1               5                  10                  15

Glu Gln Ala Ala Leu Ala Ala Ala Asn Ser Ala Leu Ala Asn Ala Val

-continued

```
                20                  25                  30
Val Val Arg Pro Phe Leu Ser Arg Leu Gln Thr Glu Ile Leu Ile Asn
             35                  40                  45
Leu Met Gln Pro Arg Gln Leu Val Phe Arg Pro Glu Val Leu Trp Asn
         50                  55                  60
His Pro Ile Gln Arg Val Ile His Asn Glu Leu Gln Tyr Cys Arg
 65                  70                  75                  80
Ala Arg Ala Gly Arg Cys Leu Glu Val Gly Ala His Pro Arg Ser Ile
                 85                  90                  95
Asn Asp Asn Pro Asn Val Leu His Arg Cys Phe Leu Arg Pro Val Gly
                100                 105                 110
Arg Asp Val Gln Arg Trp Tyr Ser Ala Pro Thr Arg Gly Pro Ala Ala
             115                 120                 125
Asn Cys Arg Arg Ser Ala Leu Arg Gly Leu Pro Pro Val Asp Arg Thr
         130                 135                 140
Tyr Cys Phe Asp Gly Phe Ser Arg Cys Ala Phe Ala Ala Glu Thr Gly
145                 150                 155                 160
Val Ala Leu Tyr Ser Leu His Asp Leu Trp Pro Ala Asp Val Ala Glu
                165                 170                 175
Ala Met Ala Arg His Gly Met Thr Arg Leu Tyr Ala Ala Leu His Leu
             180                 185                 190
Pro Pro Glu Val Leu Leu Pro Pro Gly Thr Tyr His Thr Thr Ser Tyr
         195                 200                 205
Leu Leu Ile His Asp Gly Asp Arg Ala Val Val Thr Tyr Glu Gly Asp
     210                 215                 220
Thr Ser Ala Gly Tyr Asn His Asp Val Ser Ile Leu Arg Ala Trp Ile
225                 230                 235                 240
Arg Thr Thr Lys Ile Val Gly Asp His Pro Leu Val Ile Glu Arg Val
                245                 250                 255
Arg Ala Ile Gly Cys His Phe Val Leu Leu Thr Ala Ala Pro Glu
             260                 265                 270
Pro Ser Pro Met Pro Tyr Val Pro Tyr Pro Arg Ser Thr Glu Val Tyr
         275                 280                 285
Val Arg Ser Ile Phe Gly Pro Gly Ser Pro Ser Leu Phe Pro Ser
     290                 295                 300
Ala Cys Ser Thr Lys Ser Thr Phe His Ala Val Pro Val His Ile Trp
305                 310                 315                 320
Asp Arg Leu Met Leu Phe Gly Ala Thr Leu Asp Asp Gln Ala Phe Cys
                325                 330                 335
Cys Ser Arg Leu Met Thr Tyr Leu Arg Gly Ile Ser Tyr Lys Val Thr
             340                 345                 350
Val Gly Ala Leu Val Ala Asn Glu Gly Trp Asn Ala Ser Glu Asp Ala
         355                 360                 365
Leu Thr Ala Val Ile Thr Ala Ala Tyr Leu Thr Ile Cys His Gln Arg
     370                 375                 380
Tyr Leu Arg Thr Gln Ala Ile Ser Lys Gly Met Arg Arg Leu Glu Val
385                 390                 395                 400
Glu His Ala Gln Lys Phe Ile Thr Arg Leu Tyr Ser Trp Leu Phe Glu
                405                 410                 415
Lys Ser Gly Arg Asp Tyr Ile Pro Gly Arg Gln Leu Gln Phe Tyr Ala
             420                 425                 430
Gln Cys Arg Arg Trp Leu Ser Ala Gly Phe His Leu Asp Pro Arg Val
         435                 440                 445
```

```
Leu Val Phe Asp Glu Ser Val Pro Cys Arg Cys Arg Thr Phe Leu Lys
    450                 455                 460

Lys Val Ala Gly Lys Phe Cys Cys Phe Met Arg Trp Leu Gly Gln Glu
465                 470                 475                 480

Cys Thr Cys Phe Leu Glu Pro Ala Glu Gly Leu Val Gly Asp His Gly
                485                 490                 495

His Asp Asn Glu Ala Tyr Glu Gly Ser Glu Val Asp Gln Ala Glu Pro
                500                 505                 510

Ala His Leu Asp Val Ser Gly Thr Tyr Ala Val His Gly His Gln Leu
        515                 520                 525

Val Ala Leu Tyr Arg Ala Leu Asn Val Pro His Asp Ile Ala Ala Arg
    530                 535                 540

Ala Ser Arg Leu Thr Ala Thr Val Glu Leu Val Ala Gly Pro Asp Arg
545                 550                 555                 560

Leu Glu Cys Arg Thr Val Leu Gly Asn Lys Thr Phe Arg Thr Thr Val
                565                 570                 575

Val Asp Gly Ala His Leu Glu Ala Asn Gly Pro Glu Gln Tyr Val Leu
                580                 585                 590

Ser Phe Asp Ala Ser Arg Gln Ser Met Gly Ala Gly Ser His Asn Leu
        595                 600                 605

Thr Tyr Glu Leu Thr Pro Ala Gly Leu Gln Val Arg Ile Ser Ser Asn
    610                 615                 620

Gly Leu Asp Cys Thr Ala Thr Phe Pro Pro Gly Ala Pro Ser Ala
625                 630                 635                 640

Ala Pro Gly Glu Val Ala Ala Phe Cys Ala Ala Leu Tyr Arg Tyr Asn
                645                 650                 655

Arg Phe Thr Gln Arg His Ser Leu Thr Gly Gly Leu Trp Leu His Pro
                660                 665                 670

Glu Gly Leu Leu Gly Ile Phe Pro Pro Phe Ser Pro Gly His Ile Trp
        675                 680                 685

Glu Ser Ala Asn Pro Phe Cys Gly Glu Gly Thr Leu Tyr Thr Arg Thr
    690                 695                 700

Trp Ser Thr Ser Gly Phe Ser Ser Asp Phe Ser Pro Pro Glu Ala Ala
705                 710                 715                 720

Ala Pro Ala Ser Ala Ala Pro Gly Leu Pro His Pro Thr Pro Pro
                725                 730                 735

Ala Ser Asp Ile Trp Ala Leu Pro Pro Ser Glu Glu Cys Tyr Thr
                740                 745                 750

Arg Leu Gly Asn Asp Phe His Thr Asn Lys Arg Val Cys Glu Glu Ile
    755                 760                 765

Ala Ile Ile Pro Ser Lys Lys Pro Arg Asn Lys Met Ala Gly Tyr Val
770                 775                 780

Thr His Leu Met Lys Arg Ile Gln Arg Gly Pro Val Arg Gly Ile Ser
785                 790                 795                 800

Ile Lys Leu Gln Glu Glu Ala Gln Val Asp Ala Ala Ser Val Pro Leu
                805                 810                 815

Thr Leu Val Pro Ala Gly Ser Pro Ser Pro Val Val Ser Pro Ser Pro
                820                 825                 830

Pro Pro Pro Pro Pro Val Arg Lys Pro Ser Thr Pro Pro Pro Ser Arg
        835                 840                 845

Thr Arg Arg Leu Leu Tyr Thr Tyr Pro Asp Gly Ala Lys Val Tyr Ala
    850                 855                 860
```

Gly Ser Leu Phe Glu Ser Asp Cys Asp Trp Leu Val Asn Ala Ser Asn
865                 870                 875                 880

Pro Gly His Arg Pro Gly Gly Leu Cys His Ala Phe His Gln Arg
            885                 890                 895

Phe Pro Glu Ala Phe Tyr Pro Thr Glu Phe Ile Met Arg Glu Gly Leu
        900                 905                 910

Ala Ala Tyr Thr Leu Thr Pro Arg Pro Ile Ile His Ala Val Ala Pro
        915                 920                 925

Asp Tyr Arg Val Glu Gln Asn Pro Lys Arg Leu Glu Ala Ala Tyr Arg
    930                 935                 940

Glu Thr Cys Ser Arg Arg Gly Thr Ala Ala Tyr Pro Leu Leu Gly Ser
945                 950                 955                 960

Gly Ile Tyr Gln Val Pro Val Ser Leu Ser Phe Asp Ala Trp Glu Arg
            965                 970                 975

Asn His Arg Pro Gly Asp Glu Leu Tyr Leu Thr Glu Pro Ala Ala Ala
            980                 985                 990

Trp Phe Glu Ala Asn Lys Pro Ala Gln Pro Ala Leu Thr Ile Thr Glu
        995                 1000                1005

Asp Thr Ala Arg Thr Ala Ser Leu Ala Leu Glu Ile Asp Ala Ala Thr
    1010                1015                1020

Glu Val Gly Arg Ala Cys Ala Gly Cys Thr Ile Ser Pro Gly Ile Val
1025                1030                1035                1040

His Tyr Gln Phe Thr Ala Gly Val Pro Gly Ser Gly Lys Ser Arg Ser
            1045                1050                1055

Ile Xaa Gln Gly Asp Val Asp Val Val Val Pro Thr Arg Glu Leu
            1060                1065                1070

Arg Asn Ser Trp Arg Arg Gly Phe Ala Ala Phe Thr Pro His Thr
    1075                1080                1085

Ala Ala Arg Val Thr Asn Gly Arg Arg Val Val Ile Asp Glu Ala Pro
    1090                1095                1100

Ser Leu Pro Pro His Leu Leu Leu His Met Gln Arg Ala Ser Ser
1105                1110                1115                1120

Val His Leu Leu Gly Asp Pro Asn Gln Ile Pro Ala Ile Asp Phe Glu
            1125                1130                1135

His Ala Gly Leu Val Pro Ala Ile Arg Pro Glu Leu Ala Pro Thr Ser
            1140                1145                1150

Trp Trp His Val Thr His Arg Cys Pro Ala Asp Val Cys Glu Leu Ile
        1155                1160                1165

Arg Gly Ala Tyr Pro Lys Ile Gln Thr Thr Ser Arg Val Leu Arg Ser
    1170                1175                1180

Leu Phe Trp Asn Glu Pro Ala Ile Gly Gln Lys Leu Val Phe Thr Gln
1185                1190                1195                1200

Ala Ala Lys Ala Ala Asn Pro Gly Ala Ile Thr Val His Glu Ala Gln
            1205                1210                1215

Gly Ala Thr Phe Thr Glu Thr Val Ile Ala Thr Ala Asp Ala Arg
        1220                1225                1230

Gly Leu Ile Gln Ser Ser Arg Ala His Ala Ile Val Ala Leu Thr Arg
    1235                1240                1245

His Thr Glu Lys Cys Val Ile Leu Asp Ala Pro Gly Leu Leu Arg Glu
    1250                1255                1260

Val Gly Ile Ser Asp Val Ile Val Asn Asn Phe Phe Leu Ala Gly Gly
1265                1270                1275                1280

Glu Val Gly His His Arg Pro Ser Val Ile Pro Arg Gly Asn Pro Asp

```
                    1285              1290              1295
Gln Asn Leu Gly Thr Leu Gln Ala Phe Pro Pro Ser Cys Gln Ile Ser
                1300              1305              1310
Ala Tyr His Gln Leu Ala Glu Glu Leu Gly His Arg Pro Ala Pro Val
            1315              1320              1325
Ala Ala Val Leu Pro Pro Cys Pro Glu Leu Glu Gln Gly Leu Leu Tyr
        1330              1335              1340
Met Pro Gln Glu Leu Thr Val Ser Asp Ser Val Leu Val Phe Glu Leu
1345              1350              1355              1360
Thr Asp Ile Val His Cys Arg Met Ala Ala Pro Ser Gln Arg Lys Ala
                1365              1370              1375
Val Leu Ser Thr Leu Val Gly Arg Tyr Gly Arg Arg Thr Lys Leu Tyr
            1380              1385              1390
Glu Ala Ala His Ser Asp Val Arg Glu Ser Leu Ala Arg Phe Ile Pro
        1395              1400              1405
Thr Ile Gly Pro Val Gln Ala Thr Thr Cys Glu Leu Tyr Glu Leu Val
        1410              1415              1420
Glu Ala Met Val Glu Lys Gly Gln Asp Gly Ser Ala Val Leu Glu Leu
1425              1430              1435              1440
Asp Leu Cys Asn Arg Asp Val Ser Arg Ile Thr Phe Phe Gln Lys Asp
                1445              1450              1455
Cys Asn Lys Phe Thr Thr Gly Glu Thr Ile Ala His Gly Lys Val Gly
            1460              1465              1470
Gln Gly Ile Ser Ala Trp Ser Lys Thr Phe Cys Ala Leu Phe Gly Pro
        1475              1480              1485
Trp Phe Arg Ala Ile Glu Lys Glu Ile Leu Ala Leu Leu Pro Pro Asn
        1490              1495              1500
Val Phe Tyr Gly Asp Ala Tyr Glu Glu Ser Val Leu Ala Ala Ala Val
1505              1510              1515              1520
Ser Gly Ala Gly Ser Cys Met Val Phe Glu Asn Asp Phe Ser Glu Phe
                1525              1530              1535
Asp Ser Thr Gln Asn Asn Phe Ser Leu Gly Leu Glu Cys Val Val Met
            1540              1545              1550
Glu Glu Cys Gly Met Pro Gln Trp Leu Ile Arg Leu Tyr His Leu Val
        1555              1560              1565
Arg Ser Ala Trp Ile Leu Gln Ala Pro Lys Glu Ser Leu Lys Gly Phe
        1570              1575              1580
Trp Lys Lys His Ser Gly Glu Pro Gly Thr Leu Leu Trp Asn Thr Val
1585              1590              1595              1600
Trp Asn Met Ala Ile Ile Ala His Cys Tyr Glu Phe Arg Asp Phe Arg
                1605              1610              1615
Val Ala Ala Phe Lys Gly Asp Asp Ser Val Val Leu Cys Ser Asp Tyr
            1620              1625              1630
Arg Gln Ser Arg Asn Ala Ala Ala Leu Ile Ala Gly Cys Gly Leu Lys
        1635              1640              1645
Leu Lys Val Asp Tyr Arg Pro Ile Gly Leu Tyr Ala Gly Val Val Val
        1650              1655              1660
Ala Pro Gly Leu Gly Thr Leu Pro Asp Val Val Arg Phe Ala Gly Arg
1665              1670              1675              1680
Leu Ser Glu Lys Asn Trp Gly Pro Gly Pro Glu Arg Ala Glu Gln Leu
                1685              1690              1695
Arg Leu Ala Val Cys Asp Phe Leu Arg Gly Leu Thr Asn Val Ala Gln
            1700              1705              1710
```

```
Val Cys Val Asp Val Val Ser Arg Val Tyr Gly Val Ser Pro Gly Leu
         1715                1720                1725

Val His Asn Leu Ile Gly Met Leu Gln Thr Ile Ala Asp Gly Lys Ala
    1730                1735                1740

His Phe Thr Glu Thr Ile Lys Pro Val Leu Asp Leu Thr Asn Ser Ile
1745                1750                1755                1760

Ile Gln Arg Val Glu
                1765

<210> SEQ ID NO 3
<211> LENGTH: 113
<212> TYPE: PRT
<213> ORGANISM: Hepatitis E virus
<220> FEATURE:
<223> OTHER INFORMATION: Hepatitis E virus Kernow genotype 3 replicating
      variant ORF3, viral protein

<400> SEQUENCE: 3

Met Gly Ser Pro Cys Ala Leu Gly Leu Phe Cys Cys Ser Ser Cys
1               5                   10                  15

Phe Cys Leu Cys Cys Pro Arg His Arg Pro Ala Ser Arg Leu Ala Val
            20                  25                  30

Val Val Gly Gly Ala Ala Ala Val Pro Ala Val Val Ser Gly Val Thr
        35                  40                  45

Gly Leu Ile Leu Ser Pro Ser Pro Ser Pro Ile Phe Ile Gln Pro Thr
    50                  55                  60

Pro Ser Pro Pro Ile Ser Phe His Asn Pro Gly Leu Glu Leu Ala Leu
65                  70                  75                  80

Gly Ser Arg Pro Ala Pro Leu Ala Pro Leu Gly Val Thr Ser Pro Ser
                85                  90                  95

Ala Pro Pro Leu Pro Pro Ala Val Asp Leu Pro Gln Leu Gly Leu Arg
            100                 105                 110

Arg

<210> SEQ ID NO 4
<211> LENGTH: 660
<212> TYPE: PRT
<213> ORGANISM: Hepatitis E virus
<220> FEATURE:
<223> OTHER INFORMATION: Hepatitis E virus Kernow genotype 3 replicating
      variant ORF2, capsid protein

<400> SEQUENCE: 4

Met Cys Pro Arg Val Val Leu Leu Leu Phe Phe Val Phe Leu Pro Met
1               5                   10                  15

Leu Pro Ala Pro Pro Ala Gly Gln Pro Ser Gly Arg Arg Arg Gly Arg
            20                  25                  30

Arg Ser Gly Gly Ala Gly Gly Gly Phe Trp Gly Asp Arg Val Asp Ser
        35                  40                  45

Gln Pro Phe Ala Leu Pro Tyr Ile His Pro Thr Asn Pro Phe Ala Ala
    50                  55                  60

Asp Ile Val Ser Gln Ser Gly Ala Gly Thr Arg Pro Arg Gln Pro Pro
65                  70                  75                  80

Arg Pro Leu Gly Ser Ala Trp Arg Asp Gln Ser Gln Arg Pro Ser Ala
                85                  90                  95

Ala Pro Arg Arg Arg Ser Ala Pro Ala Gly Ala Ala Pro Leu Thr Ala
            100                 105                 110
```

```
Val Ser Pro Ala Pro Asp Thr Ala Pro Val Pro Asp Val Asp Ser Arg
            115                 120                 125
Gly Ala Ile Leu Arg Arg Gln Tyr Asn Leu Ser Thr Ser Pro Leu Thr
130                 135                 140
Ser Ser Val Ala Ser Gly Thr Asn Leu Val Leu Tyr Ala Ala Pro Leu
145                 150                 155                 160
Asn Pro Leu Leu Pro Leu Gln Asp Gly Thr Asn Thr His Ile Met Ala
                165                 170                 175
Thr Glu Ala Ser Asn Tyr Ala Gln Tyr Arg Val Val Arg Ala Thr Ile
            180                 185                 190
Arg Tyr Arg Pro Leu Val Pro Asn Ala Val Gly Gly Tyr Ala Ile Ser
            195                 200                 205
Ile Ser Phe Trp Pro Gln Thr Thr Thr Pro Thr Ser Val Asp Met
210                 215                 220
Asn Ser Ile Thr Ser Thr Asp Val Arg Ile Leu Val Gln Pro Gly Ile
225                 230                 235                 240
Ala Ser Glu Leu Val Ile Pro Ser Glu Arg Leu His Tyr Arg Asn Gln
                245                 250                 255
Gly Trp Arg Ser Val Glu Thr Thr Gly Val Ala Glu Glu Ala Thr
            260                 265                 270
Ser Gly Leu Val Met Leu Cys Ile His Gly Ser Pro Val Asn Ser Tyr
            275                 280                 285
Thr Asn Thr Pro Tyr Thr Gly Ala Leu Gly Leu Leu Asp Phe Ala Leu
            290                 295                 300
Glu Leu Glu Phe Arg Asn Leu Thr Pro Gly Asn Thr Asn Thr Arg Val
305                 310                 315                 320
Ser Arg Tyr Thr Ser Thr Ala Arg His Arg Leu Arg Arg Gly Ala Asp
                325                 330                 335
Gly Thr Ala Glu Leu Thr Thr Ala Ala Thr Arg Phe Met Lys Asp
            340                 345                 350
Leu His Phe Thr Gly Thr Asn Gly Val Gly Val Gly Arg Gly Ile
            355                 360                 365
Ala Leu Thr Leu Phe Asn Leu Ala Asp Thr Leu Leu Gly Gly Leu Pro
370                 375                 380
Thr Glu Leu Ile Ser Ser Ala Gly Gly Gln Leu Phe Tyr Ser Arg Pro
385                 390                 395                 400
Val Val Ser Ala Asn Gly Glu Pro Thr Val Lys Leu Tyr Thr Ser Val
                405                 410                 415
Glu Asn Ala Gln Gln Asp Lys Gly Ile Thr Ile Pro His Asp Ile Asp
            420                 425                 430
Leu Gly Asp Ser Arg Val Val Ile Gln Asp Tyr Asp Asn Gln His Glu
            435                 440                 445
Gln Asp Arg Pro Thr Pro Ser Pro Ala Pro Ser Arg Pro Phe Ser Val
            450                 455                 460
Leu Arg Ala Asn Asp Val Leu Trp Leu Ser Leu Thr Ala Ala Glu Tyr
465                 470                 475                 480
Asp Gln Ala Thr Tyr Gly Ser Ser Thr Asn Pro Met Tyr Val Ser Asp
                485                 490                 495
Thr Val Thr Phe Val Asn Val Ala Gly Ala Gln Ala Val Ala Arg
            500                 505                 510
Ser Leu Asp Trp Ser Lys Val Thr Leu Asp Gly Arg Pro Leu Thr Thr
            515                 520                 525
Ile Gln Gln Tyr Ser Lys Thr Phe Tyr Val Leu Pro Leu Arg Gly Lys
```

```
                 530              535              540
Leu Ser Phe Trp Glu Ala Gly Thr Thr Arg Ala Gly Tyr Pro Tyr Asn
545                 550              555                  560

Tyr Asn Thr Thr Ala Ser Asp Gln Ile Leu Ile Glu Asn Ala Ala Gly
                565              570              575

His Arg Val Ala Ile Ser Thr Tyr Thr Thr Ser Leu Gly Ala Gly Pro
                580              585              590

Thr Ser Ile Ser Ala Val Gly Val Leu Ala Pro His Ser Ala Leu Ala
                595              600              605

Val Leu Glu Asp Thr Val Asp Tyr Pro Ala Arg Ala His Thr Phe Asp
        610              615              620

Asp Phe Cys Pro Glu Cys Arg Thr Leu Gly Leu Gln Gly Cys Ala Phe
625             630              635                  640

Gln Ser Thr Ile Ala Glu Leu Gln Arg Leu Lys Thr Glu Val Gly Lys
                645              650              655

Thr Arg Glu Ser
            660

<210> SEQ ID NO 5
<211> LENGTH: 7264
<212> TYPE: DNA
<213> ORGANISM: Hepatitis E virus
<220> FEATURE:
<223> OTHER INFORMATION: Hepatitis E virus Kernow C1

<400> SEQUENCE: 5
ggcagaccac gtatgtggtc gatgccatgg aggcccacca gttcattaag gctcctggca      60
ttactactgc cattgagcag gctgctctgg ctgcggccaa ttccgccttg gcgaatgctg     120
tggtggttcg gccgttttta ccccgtctac aaacygagat tcttatcaat ttgatgcaac     180
cccggcagtt ggttttccgc cctgaagtgc tttggaatca tcctatccag cgggttatac     240
acaatgaact agaacagtac tgccgggccc gtgctggccg ctgtttggag gtcggagccc     300
atccgagatc tattaatgat aaccccaacg tcttgcaccg tgcttccttt agaccggttg     360
gcagggatgt tcagcgctgg tactctgccc ccacccgtgg ccctgcggcc aattgccgcc     420
gctccgcgct gcgtggcctc cccccgttg accgcaccta ctgttttgat ggattctccc      480
gttgtgcttt tgctgcagag accggtgtgg cccttactc tttgcatgac ctttggccag      540
ctgatgttgc agaggcgatg gcccgtcatg ggatgacacg gttgtatgcc gcactacatc     600
ttcctcctga ggtgctgcta ccacccggca cctatcacac aacttcgtat ctcctgattc     660
acgacggcga tcgcgccgtt gtaacctatg agggcgatac cagtgcgggc tataaccatg     720
atgtttccat acttcgtgcg tggatccgta ctactaaaat agttggtgac acccgttgg      780
ttatagagcg tgtgcgggcc attggttgtc atttcgtgct gttgctcacc gcggcccctg     840
agccgtcacc tatgccttat gtcccctacc ctcgttcaac ggaggtgtat gttcggtcta     900
tatttggccc tggcggctct ccatccttgt tccgtcagc tgctctact aaatctacct       960
tccatgctgt cccggtccat atctgggatc ggctcatgct ctttggtgcc accctggatg    1020
atcaggcgtt ctgttgttca cgactcatga cttacctccg tggtattagc tacaaggtca    1080
ctgttggtgc gcttgttgct aatgaggggt ggaacgcctc tgaagatgct cttactgcag    1140
tgatcactgc ggcttatctg actatctgcc atcagcgcta cctccgtacc caggcgatat    1200
ccaagggcat gcgccggttg gaggttgagc atgcccagaa atttatcaca agactctaca    1260
gttggctatt tgagaagtct ggccgtgatt acatccccgg ccgccagctc cagttttatg    1320
```

```
cacagtgccg acggtggcta tctgcaggat tccatctgga ccccagggtg cttgttttttg    1380 atgaatcagt gccatgtcgt tgtaggacgt tcttgaagaa agtcgcgggt aaattctgct    1440
gttttatgcg gtggttaggg caggagtgca cctgcttctt ggagccagcc gagggtttag    1500
ttggcgacca tggccatgac aatgaggctt atgaaggttc tgaggtcgac caggctgaac    1560
ctgcccatct tgatgtttcg gggacttatg ccgtccacgg gcaccagctt gtagccctct    1620
atagggcact taatgtccca catgatattg ccgctcgagc ttcccgacta acggctactg    1680
ttgagcttgt tgcaggtcca gaccgcttgg agtgccgcac tgtgctcggt aataagacct    1740
tccggacgac ggtggttgat ggcgcccatc ttgaagcgaa tggcccagag cagtatgtcc    1800
tgtcatttga cgcctcccgt cagtctatgg gggccgggtc gcacaacctc acttatgagc    1860
tcacccctgc cggtttgcag gttaggatct catctaacgg tctggattgc actgctacat    1920 tccccccccgg cggtgcccct agcgccgcgc caggggaggt ggcagccttc tgtggtgccc    1980
tttatagata taacaggttc acccagcggc actcgctgac cggtggacta tggttacacc    2040
ctgagggatt gctgggcatc ttccctccat tctcccctgg gcatatctgg gagtctgcta    2100
accccttttg cggggagggg actttgtata cccggacctg gtcaacatct ggcttttcta    2160
gtgatttctc tcccctgag gcggccgccc ctgcttcggc tgctgccccg gggctgcccc    2220
atcctacccc gcctgttagt gatatttggg cgttaccacc gccctcagag gagtctcagg    2280
tcgatgcagc atctgtgccc cttaccctcg tgcctgctgg gtcgcccaac cctattgtgt    2340
tacctycccc cccccccct ccccccgtgc gtaagccatc aacaccccg ccttctcgta    2400 cccgtcgcct cctctacacc tatcccgacg gcgctaaggt gtatgcaggg tcattgtttg    2460
aatcagactg tgattggctg gttaacgcct caaacccggg ccatcgccct ggaggtggcc    2520
tctgtcatgc ctttcatcaa cgttttccag aggcgtttta ttggactgaa ttcattatgc    2580
gtgagggcct agcggcatac accctgaccc cgcgccctat catccacgca gtggcgcccg    2640
actacagggt tgagcagaac ccgaagaggc tcgaggcagc gtaccgggaa acttgctccc    2700
gtcgtggcac cgctgcttac ccgcttttag gctcgggcat ataccaggtc cctgtcagcc    2760
tcagttttga tgcctgggaa cgcaatcatc gccccggcga tgagctttac ttgactgagc    2820
ccgctgcggc ttggtttgag gctaataagc cggcgcagcc ggcgcttacc ataactgagg    2880
acacggctcg tacggccaac ctggcactag agatcgacgc cgctacagag gttggccgtg    2940
cttgtgccgg ctgcactatc agtcctggga ttgtgcacta tcagtttacc gctggggtcc    3000
cgggctcggg caagtcaagg tccatacaac agggagatgt cgatgtggtg gttgtgccca    3060
cccgggagct ccgtaatagt tggcgccgcc ggggtttcgc ggctttcaca ccccacacag    3120
cggcccgtgt tactaacggc cgccgcgttg tgattgatga ggccccatct ctcccgccac    3180
acctgttgct gctacatatg cagcgggcct cctcggtcca cctactcggt gacccaaatc    3240
agatccctgc tatcgatttt gaacacgccg gcctggtccc cgcgatccgc cccgagcttg    3300
caccaacgag ctggtggcac gtcacacacc gctgcccggc cgatgtgtgc gaactcatac    3360
gcggggccta ccccaaaatc cagaccacga gccgtgtgct acggtccctg ttttggaatg    3420
aaccggctat cggccagaag ttggtttttta cgcaggctgc caaggccgct aaccctggtg    3480
cgattacggt tcacgaagct cagggtgcca ccttcactga gaccacagtt atagccacgg    3540
ccgacgccag gggcctcatt cagtcatccc gggcccatgc tatagttgca cttacccgcc    3600
acaccgagaa gtgcgtcatt ttggatgctc ccggcctgct gcgtgaagtc ggtatctcgg    3660
```

```
atgtgattgt caataatttt ttccttgcag gcggagaggt cggccatcac cgcccttctg    3720
tgatacccog cggtaacccc gatcagaacc tcgggacttt acaagccttc ccgccgtcct    3780
gccagattag tgcttaccac cagctggctg aggaattagg ccatcgccct gcccctgttg    3840
ccgccgtctt gcccccttgc cccgagcttg agcagggcct gctttacatg ccacaagagc    3900
ttaccgtgtc tgatagtgtg ctggttttg agcttacgga catagtccac tgccgcatgg    3960
ccgctccaag ccagcgaaag gctgttcttt caacacttgt ggggcggtat ggccgtagga    4020
cgaagttata tgaggcagca cattcagatg tccgtgagtc cctagccagg ttcatcccca    4080
ctatcgggcc cgttcaggcc accacatgtg agttgtatga gttggttgag gccatggtgg    4140
agaagggtca ggacgggtca gccgtcttag agctagatct ctgcaatcgt gatgtctcgc    4200
gcatcacatt tttccaaaag gattgcaaca agtttacaac tggtgagact atcgcccatg    4260
gcaaggttgg tcagggtata tcggcctgga gcaagacctt ctgcgctttg tttggcccgt    4320
ggttccgtgc cattgagaaa gaaatactgg ccctgctccc gcctaatgtc ttttatggcg    4380
atgcttatga ggagtcagtg tttgctgccg ctgtgtcagg ggcggggtca tgcatggtat    4440
ttgaaaatga cttttcggag tttgatagca cccagaacaa cttctctctc ggccttgagt    4500
gtgtggttat ggaggagtgc ggcatgcctc aatggttaat taggttgtat cacctggtac    4560
ggtcagcctg gattttgcag gcgccaaagg agtctcttaa gggtttytgg aagaagcatt    4620
ctggtgagcc cggtacccct ctttggaaca ccgtttggaa catggcaatc atagcacatt    4680
gctacgagtt ccgtgacttt cgtgttgctg ccttttaaggg tgatgattcg gtggtcctct    4740
gtagcgacta ccggcagagc cgcaatgcgg cagctttgat tgctggctgt gggcttaaat    4800
tgaaggttga ctatcgcccc attgggctgt atgctggggt ggtggtggcc cctggcttgg    4860
ggacactgcc tgatgtggtg cgttttgctg gtcggctgtc tgaaaagaat tggggccccg    4920
gcccggaacg tgctgagcag ctacgtcttg ctgtttgtga tttccttcga gggttgacga    4980
acgttgcgca ggtctgtgtt gatgttgtgt cccgtgtcta tggagttagc cccgggctgg    5040
tacataacct tattggcatg ttgcagacca ttgccgatgg caaggcccac tttacagaga    5100
ctattaaacc tgttcttgat cttacaaatt ccatcataca gcgggtagaa tgaataacat    5160
gtttgttgca tcgcccatgg gatcaccatg cgccctaggg ttgttctgct gctgttcttc    5220
gtgtttctgc ctatgctgcc cgcgccaccg gccggccagc cgtctggccg tcgtcgtggg    5280
cggcgcagcg gcggtgccgg cggtggtttc tggggtgaca gggttgattc tcagcccttc    5340
gccctcccct atattcatcc aaccaacccc ttcgccgccg atgtcgtttc acaatccggg    5400
gctggaactc gccctcggca gccgccccgc ccccttggct ccgcttggcg tgaycagtcc    5460
cagcgccccc ccgctgcccc ccgccgtcga tctgccccag ctggggctgc gccgttgact    5520
gctgtatcac cggcccctga cacagcccct gtacctgatg ttgattcacg tggtgctatt    5580
ctgcgtcggc agtataattt gtccacgtcc ccgctcacgt catctgttgc ttcgggtacc    5640
aacttggttc tctacgctgc cccgctaaat ccctcttgc ccctccagga tggcaccaat    5700
acccatatca tggctactga ggcatccaac tatgctcagt atcgggtcgt tcgagctacg    5760
atccgctacc gcccgctggt gccaaatgct gttggtggtt atgctatttc tatttctttt    5820
tggcctcaaa ctacaactac ccctacttct gttgatatga attccatcac ttccactgat    5880
gttaggattt tggtccagcc cggtattgcc tccgagttag tcatccctag tgagcgcctt    5940
cattatcgca atcaaggctg gcgctctgtt gagaccacag gtgtggctga ggaggaggct    6000
acctccggtc tggtaatgct ttgcattcat ggctctcctg ttaactctta tactaataca    6060
```

-continued

```
ccttacactg gtgcgttggg gctccttgat tttgcactag agcttgaatt caggaacttg    6120
acacccggga acaccaacac ccgtgttttcc cggtatacca gcacagcccg ccatcggttg   6180
cgccgcggtg ctgatgggac cgctgagctt actaccacag cagccacacg atttatgaag   6240
gatctgcatt tcactggtac taatggcgtt ggtgaggtgg gtcgcggtat cgccctgaca   6300
ctgttcaatc tcgctgatac gcttctaggt ggtttaccga cagaattgat ttcgtcggct   6360
gggggtcagt tgttctactc ccgccctgtt gtctcggcca atggcgagcc gacagtaaag   6420
ttatacacat ctgtagagaa tgcgcagcaa gacaagggca ttaccatccc acacgatata   6480
gatttgggtg attcccgtgt ggttattcag gattatgata tcagcacga gcaagaccga   6540 cccacgccgt cacctgcccc ctcacgccct ttctcagtcc ttcgcgctaa cgatgttttg   6600
tggctctccc tcactgccgc tgagtacgat cagactacgt atgggtcgtc taccaaccct   6660
atgtatgtct ctgatacagt caccttttgtc aatgtggcca ctggtgctca ggctgttgcc   6720
cgctctcttg attggtctaa agttactttg gatggtcgcc cccttactac cattcagcag   6780
tattctaaga cattctatgt tctcccgctc cgcgggaagc tgtcctttttg ggaggctggc   6840 acaactaggg ccggctaccc atataactat aacaccactg ctagtgatca aattctgatt   6900
gagaatgcgg ccggccatcg tgtcgctatc tccacctaca ctaccagcct gggtgccggt   6960
cctacctcga tctccgcggt gggtgtatta gccccacact cggcccttgc tgttcttgag   7020
gacactgttg attaccctgc tcgtgctcac acttttgatg atttctgccc ggagtgccgt   7080
accctaggtt tgcaggggttg tgcattccag tccactattg ctgagcttca gcgccttaaa   7140
atgaaggtag gcaaaacccg ggagtcttaa ttaattcctt tcgtgccccc ttcgcagtct   7200
tcctttckgc tttatttctt atttctgctt cccgcgctcc ctggaaaaaa aaaaaaaaaa   7260
aaaa                                                                 7264
```

<210> SEQ ID NO 6
<211> LENGTH: 1708
<212> TYPE: PRT
<213> ORGANISM: Hepatitis E virus
<220> FEATURE:
<223> OTHER INFORMATION: Hepatitis E virus Kernow C1 ORF1, polyprotein
<220> FEATURE:
<221> NAME/KEY: VARIANT
<222> LOCATION: 774
<223> OTHER INFORMATION: Xaa = Pro or Ser

<400> SEQUENCE: 6

```
Met Glu Ala His Gln Phe Ile Lys Ala Pro Gly Ile Thr Thr Ala Ile
 1               5                  10                  15

Glu Gln Ala Ala Leu Ala Ala Ala Asn Ser Ala Leu Ala Asn Ala Val
            20                  25                  30

Val Val Arg Pro Phe Leu Ser Arg Leu Gln Thr Glu Ile Leu Ile Asn
        35                  40                  45

Leu Met Gln Pro Arg Gln Leu Val Phe Arg Pro Glu Val Leu Trp Asn
    50                  55                  60

His Pro Ile Gln Arg Val Ile His Asn Glu Leu Glu Gln Tyr Cys Arg
65                  70                  75                  80

Ala Arg Ala Gly Arg Cys Leu Glu Val Gly Ala His Pro Arg Ser Ile
                85                  90                  95

Asn Asp Asn Pro Asn Val Leu His Arg Cys Phe Leu Arg Pro Val Gly
            100                 105                 110

Arg Asp Val Gln Arg Trp Tyr Ser Ala Pro Thr Arg Gly Pro Ala Ala
```

```
            115                 120                 125
Asn Cys Arg Arg Ser Ala Leu Arg Gly Leu Pro Pro Val Asp Arg Thr
130                 135                 140

Tyr Cys Phe Asp Gly Phe Ser Arg Cys Ala Phe Ala Ala Glu Thr Gly
145                 150                 155                 160

Val Ala Leu Tyr Ser Leu His Asp Leu Trp Pro Ala Asp Val Ala Glu
                165                 170                 175

Ala Met Ala Arg His Gly Met Thr Arg Leu Tyr Ala Ala Leu His Leu
            180                 185                 190

Pro Pro Glu Val Leu Leu Pro Pro Gly Thr Tyr His Thr Thr Ser Tyr
        195                 200                 205

Leu Leu Ile His Asp Gly Asp Arg Ala Val Val Thr Tyr Glu Gly Asp
210                 215                 220

Thr Ser Ala Gly Tyr Asn His Asp Val Ser Ile Leu Arg Ala Trp Ile
225                 230                 235                 240

Arg Thr Thr Lys Ile Val Gly Asp His Pro Leu Val Ile Glu Arg Val
                245                 250                 255

Arg Ala Ile Gly Cys His Phe Val Leu Leu Thr Ala Ala Pro Glu
            260                 265                 270

Pro Ser Pro Met Pro Tyr Val Pro Tyr Pro Arg Ser Thr Glu Val Tyr
        275                 280                 285

Val Arg Ser Ile Phe Gly Pro Gly Gly Ser Pro Ser Leu Phe Pro Ser
290                 295                 300

Ala Cys Ser Thr Lys Ser Thr Phe His Ala Val Pro Val His Ile Trp
305                 310                 315                 320

Asp Arg Leu Met Leu Phe Gly Ala Thr Leu Asp Asp Gln Ala Phe Cys
                325                 330                 335

Cys Ser Arg Leu Met Thr Tyr Leu Arg Gly Ile Ser Tyr Lys Val Thr
            340                 345                 350

Val Gly Ala Leu Val Ala Asn Glu Gly Trp Asn Ala Ser Glu Asp Ala
        355                 360                 365

Leu Thr Ala Val Ile Thr Ala Ala Tyr Leu Thr Ile Cys His Gln Arg
370                 375                 380

Tyr Leu Arg Thr Gln Ala Ile Ser Lys Gly Met Arg Arg Leu Glu Val
385                 390                 395                 400

Glu His Ala Gln Lys Phe Ile Thr Arg Leu Tyr Ser Trp Leu Phe Glu
                405                 410                 415

Lys Ser Gly Arg Asp Tyr Ile Pro Gly Arg Gln Leu Gln Phe Tyr Ala
            420                 425                 430

Gln Cys Arg Arg Trp Leu Ser Ala Gly Phe His Leu Asp Pro Arg Val
        435                 440                 445

Leu Val Phe Asp Glu Ser Val Pro Cys Arg Cys Arg Thr Phe Leu Lys
450                 455                 460

Lys Val Ala Gly Lys Phe Cys Cys Phe Met Arg Trp Leu Gly Gln Glu
465                 470                 475                 480

Cys Thr Cys Phe Leu Glu Pro Ala Glu Gly Leu Val Gly Asp His Gly
                485                 490                 495

His Asp Asn Glu Ala Tyr Glu Gly Ser Glu Val Asp Gln Ala Glu Pro
            500                 505                 510

Ala His Leu Asp Val Ser Gly Thr Tyr Ala Val His Gly His Gln Leu
        515                 520                 525

Val Ala Leu Tyr Arg Ala Leu Asn Val Pro His Asp Ile Ala Ala Arg
530                 535                 540
```

```
Ala Ser Arg Leu Thr Ala Thr Val Glu Leu Val Ala Gly Pro Asp Arg
545                 550                 555                 560

Leu Glu Cys Arg Thr Val Leu Gly Asn Lys Thr Phe Arg Thr Thr Val
            565                 570                 575

Val Asp Gly Ala His Leu Glu Ala Asn Gly Pro Glu Gln Tyr Val Leu
        580                 585                 590

Ser Phe Asp Ala Ser Arg Gln Ser Met Gly Ala Gly Ser His Asn Leu
    595                 600                 605

Thr Tyr Glu Leu Thr Pro Ala Gly Leu Gln Val Arg Ile Ser Ser Asn
610                 615                 620

Gly Leu Asp Cys Thr Ala Thr Phe Pro Pro Gly Gly Ala Pro Ser Ala
625                 630                 635                 640

Ala Pro Gly Glu Val Ala Ala Phe Cys Gly Ala Leu Tyr Arg Tyr Asn
                645                 650                 655

Arg Phe Thr Gln Arg His Ser Leu Thr Gly Gly Leu Trp Leu His Pro
            660                 665                 670

Glu Gly Leu Leu Gly Ile Phe Pro Pro Phe Ser Pro Gly His Ile Trp
        675                 680                 685

Glu Ser Ala Asn Pro Phe Cys Gly Glu Gly Thr Leu Tyr Thr Arg Thr
    690                 695                 700

Trp Ser Thr Ser Gly Phe Ser Ser Asp Phe Ser Pro Pro Glu Ala Ala
705                 710                 715                 720

Ala Pro Ala Ser Ala Ala Pro Gly Leu Pro His Pro Thr Pro Pro
                725                 730                 735

Val Ser Asp Ile Trp Ala Leu Pro Pro Ser Glu Glu Ser Gln Val
                740                 745                 750

Asp Ala Ala Ser Val Pro Leu Thr Leu Val Pro Ala Gly Ser Pro Asn
                755                 760                 765

Pro Ile Val Leu Pro Xaa Pro Pro Pro Pro Val Arg Lys Pro
770                 775                 780

Ser Thr Pro Pro Pro Ser Arg Thr Arg Arg Leu Leu Tyr Thr Tyr Pro
785                 790                 795                 800

Asp Gly Ala Lys Val Tyr Ala Gly Ser Leu Phe Glu Ser Asp Cys Asp
                805                 810                 815

Trp Leu Val Asn Ala Ser Asn Pro Gly His Arg Pro Gly Gly Leu
                820                 825                 830

Cys His Ala Phe His Gln Arg Phe Pro Glu Ala Phe Tyr Trp Thr Glu
                835                 840                 845

Phe Ile Met Arg Glu Gly Leu Ala Ala Tyr Thr Leu Thr Pro Arg Pro
850                 855                 860

Ile Ile His Ala Val Ala Pro Asp Tyr Arg Val Glu Gln Asn Pro Lys
865                 870                 875                 880

Arg Leu Glu Ala Ala Tyr Arg Glu Thr Cys Ser Arg Arg Gly Thr Ala
                885                 890                 895

Ala Tyr Pro Leu Leu Gly Ser Gly Ile Tyr Gln Val Pro Val Ser Leu
                900                 905                 910

Ser Phe Asp Ala Trp Glu Arg Asn His Arg Pro Gly Asp Glu Leu Tyr
                915                 920                 925

Leu Thr Glu Pro Ala Ala Ala Trp Phe Glu Ala Asn Lys Pro Ala Gln
    930                 935                 940

Pro Ala Leu Thr Ile Thr Glu Asp Thr Ala Arg Thr Ala Asn Leu Ala
945                 950                 955                 960
```

-continued

Leu Glu Ile Asp Ala Ala Thr Glu Val Gly Arg Ala Cys Ala Gly Cys
            965                 970                 975

Thr Ile Ser Pro Gly Ile Val His Tyr Gln Phe Thr Ala Gly Val Pro
            980                 985                 990

Gly Ser Gly Lys Ser Arg Ser Ile Gln Gln Gly Asp Val Asp Val Val
            995                 1000                1005

Val Val Pro Thr Arg Glu Leu Arg Asn Ser Trp Arg Arg Gly Phe
    1010                1015                1020

Ala Ala Phe Thr Pro His Thr Ala Ala Arg Val Thr Asn Gly Arg Arg
1025                1030                1035                1040

Val Val Ile Asp Glu Ala Pro Ser Leu Pro Pro His Leu Leu Leu Leu
            1045                1050                1055

His Met Gln Arg Ala Ser Ser Val His Leu Leu Gly Asp Pro Asn Gln
            1060                1065                1070

Ile Pro Ala Ile Asp Phe Glu His Ala Gly Leu Val Pro Ala Ile Arg
            1075                1080                1085

Pro Glu Leu Ala Pro Thr Ser Trp Trp His Val Thr His Arg Cys Pro
            1090                1095                1100

Ala Asp Val Cys Glu Leu Ile Arg Gly Ala Tyr Pro Lys Ile Gln Thr
1105                1110                1115                1120

Thr Ser Arg Val Leu Arg Ser Leu Phe Trp Asn Glu Pro Ala Ile Gly
            1125                1130                1135

Gln Lys Leu Val Phe Thr Gln Ala Ala Lys Ala Ala Asn Pro Gly Ala
            1140                1145                1150

Ile Thr Val His Glu Ala Gln Gly Ala Thr Phe Thr Glu Thr Thr Val
            1155                1160                1165

Ile Ala Thr Ala Asp Ala Arg Gly Leu Ile Gln Ser Ser Arg Ala His
            1170                1175                1180

Ala Ile Val Ala Leu Thr Arg His Thr Glu Lys Cys Val Ile Leu Asp
1185                1190                1195                1200

Ala Pro Gly Leu Leu Arg Glu Val Gly Ile Ser Asp Val Ile Val Asn
            1205                1210                1215

Asn Phe Phe Leu Ala Gly Gly Glu Val Gly His His Arg Pro Ser Val
            1220                1225                1230

Ile Pro Arg Gly Asn Pro Asp Gln Asn Leu Gly Thr Leu Gln Ala Phe
            1235                1240                1245

Pro Pro Ser Cys Gln Ile Ser Ala Tyr His Gln Leu Ala Glu Glu Leu
            1250                1255                1260

Gly His Arg Pro Ala Pro Val Ala Ala Val Leu Pro Pro Cys Pro Glu
1265                1270                1275                1280

Leu Glu Gln Gly Leu Leu Tyr Met Pro Gln Glu Leu Thr Val Ser Asp
            1285                1290                1295

Ser Val Leu Val Phe Glu Leu Thr Asp Ile Val His Cys Arg Met Ala
            1300                1305                1310

Ala Pro Ser Gln Arg Lys Ala Val Leu Ser Thr Leu Val Gly Arg Tyr
            1315                1320                1325

Gly Arg Arg Thr Lys Leu Tyr Glu Ala Ala His Ser Asp Val Arg Glu
            1330                1335                1340

Ser Leu Ala Arg Phe Ile Pro Thr Ile Gly Pro Val Gln Ala Thr Thr
1345                1350                1355                1360

Cys Glu Leu Tyr Glu Leu Val Glu Ala Met Val Glu Lys Gly Gln Asp
            1365                1370                1375

Gly Ser Ala Val Leu Glu Leu Asp Leu Cys Asn Arg Asp Val Ser Arg

```
                  1380              1385              1390
Ile Thr Phe Phe Gln Lys Asp Cys Asn Lys Phe Thr Thr Gly Glu Thr
            1395              1400              1405
Ile Ala His Gly Lys Val Gly Gln Gly Ile Ser Ala Trp Ser Lys Thr
        1410              1415              1420
Phe Cys Ala Leu Phe Gly Pro Trp Phe Arg Ala Ile Glu Lys Glu Ile
1425              1430              1435              1440
Leu Ala Leu Leu Pro Pro Asn Val Phe Tyr Gly Asp Ala Tyr Glu Glu
                1445              1450              1455
Ser Val Phe Ala Ala Ala Val Ser Gly Ala Gly Ser Cys Met Val Phe
            1460              1465              1470
Glu Asn Asp Phe Ser Glu Phe Asp Ser Thr Gln Asn Asn Phe Ser Leu
            1475              1480              1485
Gly Leu Glu Cys Val Val Met Glu Glu Cys Gly Met Pro Gln Trp Leu
        1490              1495              1500
Ile Arg Leu Tyr His Leu Val Arg Ser Ala Trp Ile Leu Gln Ala Pro
1505              1510              1515              1520
Lys Glu Ser Leu Lys Gly Phe Trp Lys Lys His Ser Gly Glu Pro Gly
                1525              1530              1535
Thr Leu Leu Trp Asn Thr Val Trp Asn Met Ala Ile Ile Ala His Cys
            1540              1545              1550
Tyr Glu Phe Arg Asp Phe Arg Val Ala Ala Phe Lys Gly Asp Asp Ser
            1555              1560              1565
Val Val Leu Cys Ser Asp Tyr Arg Gln Ser Arg Asn Ala Ala Ala Leu
        1570              1575              1580
Ile Ala Gly Cys Gly Leu Lys Leu Lys Val Asp Tyr Arg Pro Ile Gly
1585              1590              1595              1600
Leu Tyr Ala Gly Val Val Val Ala Pro Gly Leu Gly Thr Leu Pro Asp
                1605              1610              1615
Val Val Arg Phe Ala Gly Arg Leu Ser Glu Lys Asn Trp Gly Pro Gly
            1620              1625              1630
Pro Glu Arg Ala Glu Gln Leu Arg Leu Ala Val Cys Asp Phe Leu Arg
            1635              1640              1645
Gly Leu Thr Asn Val Ala Gln Val Cys Val Asp Val Val Ser Arg Val
        1650              1655              1660
Tyr Gly Val Ser Pro Gly Leu Val His Asn Leu Ile Gly Met Leu Gln
1665              1670              1675              1680
Thr Ile Ala Asp Gly Lys Ala His Phe Thr Glu Thr Ile Lys Pro Val
                1685              1690              1695
Leu Asp Leu Thr Asn Ser Ile Ile Gln Arg Val Glu
            1700              1705

<210> SEQ ID NO 7
<211> LENGTH: 113
<212> TYPE: PRT
<213> ORGANISM: Hepatitis E virus
<220> FEATURE:
<223> OTHER INFORMATION: Hepatitis E virus Kernow C1 ORF3
<220> FEATURE:
<221> NAME/KEY: VARIANT
<222> LOCATION: 93
<223> OTHER INFORMATION: Xaa = any amino acid

<400> SEQUENCE: 7

Met Gly Ser Pro Cys Ala Leu Gly Leu Phe Cys Cys Cys Ser Ser Cys
 1               5                  10                  15
```

```
Phe Cys Leu Cys Cys Pro Arg His Arg Pro Ala Ser Arg Leu Ala Val
            20                  25                  30

Val Val Gly Gly Ala Ala Val Pro Ala Val Val Ser Gly Val Thr
        35                  40                  45

Gly Leu Ile Leu Ser Pro Ser Pro Ser Pro Ile Phe Ile Gln Pro Thr
50                  55                  60

Pro Ser Pro Pro Met Ser Phe His Asn Pro Gly Leu Glu Leu Ala Leu
65                  70                  75                  80

Gly Ser Arg Pro Ala Pro Leu Ala Pro Leu Gly Val Xaa Ser Pro Ser
            85                  90                  95

Ala Pro Pro Leu Pro Pro Ala Val Asp Leu Pro Gln Leu Gly Leu Arg
                100                 105                 110

Arg

<210> SEQ ID NO 8
<211> LENGTH: 660
<212> TYPE: PRT
<213> ORGANISM: Hepatitis E virus
<220> FEATURE:
<223> OTHER INFORMATION: Hepatitis E virus Kernow C1 ORF2, capsid
      protein

<400> SEQUENCE: 8

Met Arg Pro Arg Val Val Leu Leu Leu Phe Phe Val Phe Leu Pro Met
1               5                   10                  15

Leu Pro Ala Pro Pro Ala Gly Gln Pro Ser Gly Arg Arg Arg Gly Arg
            20                  25                  30

Arg Ser Gly Gly Ala Gly Gly Gly Phe Trp Gly Asp Arg Val Asp Ser
        35                  40                  45

Gln Pro Phe Ala Leu Pro Tyr Ile His Pro Thr Asn Pro Phe Ala Ala
50                  55                  60

Asp Val Val Ser Gln Ser Gly Ala Gly Thr Arg Pro Arg Gln Pro Pro
65                  70                  75                  80

Arg Pro Leu Gly Ser Ala Trp Arg Asp Gln Ser Gln Arg Pro Ser Ala
            85                  90                  95

Ala Pro Arg Arg Ser Ala Pro Ala Gly Ala Ala Pro Leu Thr Ala
                100                 105                 110

Val Ser Pro Ala Pro Asp Thr Ala Pro Val Pro Asp Val Asp Ser Arg
            115                 120                 125

Gly Ala Ile Leu Arg Arg Gln Tyr Asn Leu Ser Thr Ser Pro Leu Thr
130                 135                 140

Ser Ser Val Ala Ser Gly Thr Asn Leu Val Leu Tyr Ala Ala Pro Leu
145                 150                 155                 160

Asn Pro Leu Leu Pro Leu Gln Asp Gly Thr Asn Thr His Ile Met Ala
                165                 170                 175

Thr Glu Ala Ser Asn Tyr Ala Gln Tyr Arg Val Val Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255
```

```
Gly Trp Arg Ser Val Glu Thr Thr Gly Val Ala Glu Glu Ala Thr
            260                 265                 270

Ser Gly Leu Val Met Leu Cys Ile His Gly Ser Pro Val Asn Ser Tyr
        275                 280                 285

Thr Asn Thr Pro Tyr Thr Gly Ala Leu Gly Leu Leu Asp Phe Ala Leu
    290                 295                 300

Glu Leu Glu Phe Arg Asn Leu Thr Pro Gly Asn Thr Asn Thr Arg Val
305                 310                 315                 320

Ser Arg Tyr Thr Ser Thr Ala Arg His Arg Leu Arg Arg Gly Ala Asp
                325                 330                 335

Gly Thr Ala Glu Leu Thr Thr Thr Ala Ala Thr Arg Phe Met Lys Asp
            340                 345                 350

Leu His Phe Thr Gly Thr Asn Gly Val Gly Glu Val Gly Arg Gly Ile
        355                 360                 365

Ala Leu Thr Leu Phe Asn Leu Ala Asp Thr Leu Leu Gly Gly Leu Pro
    370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Thr Ile Pro His Asp Ile Asp
            420                 425                 430

Leu Gly Asp Ser Arg Val Val Ile Gln Asp Tyr Asp Asn Gln His Glu
        435                 440                 445

Gln Asp Arg Pro Thr Pro Ser Pro Ala Pro Ser Arg Pro Phe Ser Val
    450                 455                 460

Leu Arg Ala Asn Asp Val Leu Trp Leu Ser Leu Thr Ala Ala Glu Tyr
465                 470                 475                 480

Asp Gln Thr Thr Tyr Gly Ser Ser Thr Asn Pro Met Tyr Val Ser Asp
                485                 490                 495

Thr Val Thr Phe Val Asn Val Ala Thr Gly Ala Gln Ala Val Ala Arg
            500                 505                 510

Ser Leu Asp Trp Ser Lys Val Thr Leu Asp Gly Arg Pro Leu Thr Thr
        515                 520                 525

Ile Gln Gln Tyr Ser Lys Thr Phe Tyr Val Leu Pro Leu Arg Gly Lys
    530                 535                 540

Leu Ser Phe Trp Glu Ala Gly Thr Thr Arg Ala Gly Tyr Pro Tyr Asn
545                 550                 555                 560

Tyr Asn Thr Thr Ala Ser Asp Gln Ile Leu Ile Glu Asn Ala Ala Gly
                565                 570                 575

His Arg Val Ala Ile Ser Thr Tyr Thr Thr Ser Leu Gly Ala Gly Pro
            580                 585                 590

Thr Ser Ile Ser Ala Val Gly Val Leu Ala Pro His Ser Ala Leu Ala
        595                 600                 605

Val Leu Glu Asp Thr Val Asp Tyr Pro Ala Arg Ala His Thr Phe Asp
    610                 615                 620

Asp Phe Cys Pro Glu Cys Arg Thr Leu Gly Leu Gln Gly Cys Ala Phe
625                 630                 635                 640

Gln Ser Thr Ile Ala Glu Leu Gln Arg Leu Lys Met Lys Val Gly Lys
                645                 650                 655

Thr Arg Glu Ser
            660
```

<210> SEQ ID NO 9
<211> LENGTH: 58
<212> TYPE: PRT
<213> ORGANISM: Hepatitis E virus
<220> FEATURE:
<223> OTHER INFORMATION: Hepatitis E virus Kernow genotype 3 replicating
      variant ORF1 hypervariable region insert

<400> SEQUENCE: 9

Cys Tyr Thr Arg Leu Gly Asn Asp Phe His Thr Asn Lys Arg Val Cys
1               5                   10                  15

Glu Glu Ile Ala Ile Ile Pro Ser Lys Lys Pro Arg Asn Lys Met Ala
            20                  25                  30

Gly Tyr Val Thr His Leu Met Lys Arg Ile Gln Arg Gly Pro Val Arg
        35                  40                  45

Gly Ile Ser Ile Lys Leu Gln Glu Glu Ala
    50                  55

<210> SEQ ID NO 10
<211> LENGTH: 181
<212> TYPE: DNA
<213> ORGANISM: Hepatitis E virus
<220> FEATURE:
<223> OTHER INFORMATION: Hepatitis E virus Kernow genotype 3 replicating
      variant additional insert

<400> SEQUENCE: 10
tgatatttgg gcgttaccac cgccctccga ggaggtaaaa gacaaagatg atctggggcc       60
tgacagattc tcaacactcc cagccctaga ctcagtgcgc aagctcaggt ggctgaggat      120
attaccattt agaagaaag gaaaacaaga gcaggtcgat gcagcatctg tgccccttac      180
c                                                                      181

<210> SEQ ID NO 11
<211> LENGTH: 192
<212> TYPE: DNA
<213> ORGANISM: Hepatitis E virus
<220> FEATURE:
<223> OTHER INFORMATION: Hepatitis E virus Kernow C1 hypervariable
      region insert and flanking region

<400> SEQUENCE: 11
cgaggagtgc tacacgcgcc tgggcaacga cttccacacg aacaagcgcg tgtgcgagga       60
gatcgccatt atccctagca aaaagccccg caacaagatg gcaggttatg tcacgcatct      120
gatgaagcga attcagagag gcccagtaag aggtatctcc atccatcaag ctgcaggagg      180
aggctcaggt cg                                                          192

<210> SEQ ID NO 12
<211> LENGTH: 170
<212> TYPE: DNA
<213> ORGANISM: Homo sapiens
<220> FEATURE:
<223> OTHER INFORMATION: human ribosomal gene S17 (partial)

<400> SEQUENCE: 12
ctacacgcgc ctgggcaacg acttccacac gaacaagcgc gtgtgcgagg agatcgccat       60
tatccccagc aaaaagctcc gcaacaagat agcaggttat gtcacgcatc tgatgaagcg      120
aattcagaga ggcccagtaa gaggtatctc catcaagctg caggaggagg                 170

<210> SEQ ID NO 13
<211> LENGTH: 73

```
<212> TYPE: PRT
<213> ORGANISM: Hepatitis E virus
<220> FEATURE:
<223> OTHER INFORMATION: Hepatitis E virus Kernow C1 hypervariable
      region insert and flanking region

<400> SEQUENCE: 13

Ala Leu Pro Pro Pro Ser Glu Glu Cys Tyr Thr Arg Leu Gly Asn Asp
 1               5                  10                  15

Phe His Thr Asn Lys Arg Val Cys Glu Glu Ile Ala Ile Ile Pro Ser
                20                  25                  30

Lys Lys Pro Arg Asn Lys Met Ala Gly Tyr Val Thr His Leu Met Lys
            35                  40                  45

Arg Ile Gln Arg Gly Pro Val Arg Gly Ile Ser Ile Lys Leu Gln Glu
        50                  55                  60

Glu Ala Gln Val Asp Ala Ala Ser Val
65                  70

<210> SEQ ID NO 14
<211> LENGTH: 55
<212> TYPE: PRT
<213> ORGANISM: Homo sapiens
<220> FEATURE:
<223> OTHER INFORMATION: human ribosomal gene S17 (partial)

<400> SEQUENCE: 14

Tyr Thr Arg Leu Gly Asn Asp Phe His Thr Asn Lys Arg Val Cys Glu
 1               5                  10                  15

Glu Ile Ala Ile Ile Pro Ser Lys Lys Leu Arg Asn Lys Ile Ala Gly
                20                  25                  30

Tyr Val Thr His Leu Met Lys Arg Ile Gln Arg Gly Pro Val Arg Gly
            35                  40                  45

Ile Ser Ile Lys Leu Gln Glu
        50                  55
```

INFECTIOUS HEPATITIS E VIRUS GENOTYPE 3 RECOMBINANTS

CROSS-REFERENCE TO RELATED APPLICATIONS

This application is a U.S. National Phase of PCT Application No. PCT/US2012/020830, filed Jan. 10, 2012, which claims benefit of U.S. provisional application No. 61/554,323, filed Nov. 1, 2011 and U.S. Provisional application No. 61/431,377, filed Jan. 10, 2011, each of which applications is herein incorporated by reference for all purposes.

REFERENCE TO A SEQUENCE LISTING SUBMITTED AS AN ASCII TEXT FILE

The Sequence Listing written in file -601-2.TXT, created on Jul. 26, 2013, 65,536 bytes, machine format IBM-PC, MS-Windows operating system, is hereby incorporated by reference in its entirety and for all purposes.

BACKGROUND OF THE INVENTION

Hepatitis E virus gained notoriety as the cause of epidemics and sporadic cases of acute hepatitis in developing countries: examples include the 29,300 cases occurring during the New Delhi outbreak in 1956 and the 2,621 cases reported over 6 months in an Internally Displaced Persons Camp in Darfur in which pregnant women, as has been reported previously (1), had the highest mortality rate of 26-31% (2). HEV is the most, or second most, important cause of acute hepatitis in adults in developing countries. But contrary to recent dogma, the virus is not restricted to developing countries and sporadic cases are increasingly recognized in industrialized countries as awareness of the potential for infection spreads and tests for the virus are performed.

Historically, hepatitis E was described as an enterically-transmitted, self-limiting hepatitis that never progressed to chronicity (3). However, recently the first chronic hepatitis E was identified in Europe and chronicity has since been documented in immunocompromised solid-organ transplant recipients and HIV-infected individuals (4, 5, 6, 7). Although hepatitis E infection generally causes a mild to moderate disease, it occasionally has caused fulminant liver failure in acute cases, in chronically infected patients, and especially in those with underlying chronic liver disease or pregnancy (1, 2, 4, 5, 6, 7, 8). Additionally, hepatitis E has been misdiagnosed as drug-induced liver injury, thus complicating drug trials or treatment regimens (9). Since its discovery in 1983, documented HEV transmission was linked almost exclusively to contaminated water; that changed abruptly with the discovery of HEV infection following ingestion of uncooked deer meat (10, 11). Hepatitis E is now recognized as not just a waterborne-disease of developing countries but also as an emerging food-borne disease of industrialized countries (11, 12).

HEV is a small non-enveloped, single-stranded RNA virus with a genome size of 7.2 kb (3). The 7.2 kb genome of HEV is a single strand of positive sense RNA with three overlapping reading frames (ORFs). Approximately the first 5 kb serve as mRNA for the ORF1 polyprotein; it is not known if the polyprotein is proteolytically processed. ORF1 contains regions encoding methyl transferase/guanylyltransferase, NTPase/helicase, RNA-dependent RNA polymerase and ubiquinating activities. In addition, ORF1 encodes a Y region and X, or macro, region of unknown function and a hypervariable region (HVR) located near the middle of the ORF. The HVR varies in length and sequence among strains and genotypes: it tolerates small deletions but replication levels are severely depressed in cell culture. ORF2 and ORF3 are translated from a single bicistronic, subgenomic RNA to produce a 660 aa capsid protein and a 113 to 114 aa protein, respectively. The ORF3 protein is important for efficient release of virus particles from cultured cells and is required for infection of macaques.

To date, four HEV genotypes that infect humans are recognized (17). Genotype 1 and 2 infections have been identified exclusively in humans, whereas genotypes 3 and 4 viruses have been isolated from swine, deer, mongoose, cattle and rabbits in addition to humans (18). Genotypes 3 and 4 are ubiquitous in swine and undercooked pork may be a major source of zoonotic infections of humans (12, 18). However, cross-species transmission has not been extensively studied and additional zoonotic reservoirs probably exist.

HEV infection was long thought to be an acute infection lasting 2 to 7 weeks and that never progressed to chronicity. Recently, however, chronic HEV infection has been identified in immunesuppressed organ transplant patients or aids patients. Even more unexpectedly, some of these chronically ill patients have developed neurological symptoms and HEV has been isolated from cerebrospinal fluid. These chronic cases have been identified as genotype 3 infections.

HEV usually replicates to low titers in vivo and it has been exceedingly difficult to grow it in cultured cells and much of the virus life cycle is unknown. Okamoto and colleagues recently adapted a genotype 3 and a genotype 4 strain to replicate to high titers in two human cell lines, A549 lung cells and PLC/PRF/5 hepatoma cells (19, 20).

The epidemiology of HEV is far from understood and, in particular, the zoonotic aspects require further study. There is a need, therefore to develop HEV genotype strains that can replicate in cell culture. Further, there is a need to develop HEV vaccines, e.g., vaccines for genotype 3 strains.

The present invention relates, in part, to the discovery of a genotype 3 virus isolated from a chronically-infected patient (5) that was adapted to grow in human hepatoma cells and used to identify a set of human, swine and deer cell cultures permissive for HEV infection. The invention additionally relates to the characterization of the adapted virus to identify sequence changes that provide the ability to replicate in cell culture.

BRIEF SUMMARY OF THE INVENTION

As explained above, until recently, hepatitis E was rarely identified in industrialized countries. Hepatitis E is now increasingly reported throughout Western Europe, some Eastern European countries and Japan: most of these cases are caused by genotype 3, which is endemic in swine, and these cases are thought to be zoonotically acquired. However, transmission routes are not well understood. HEV that infect humans are divided into non-zoonotic (types 1, 2) and zoonotic (types 3, 4) genotypes. HEV cell culture is inefficient and limited and, thus far, HEV has been cultured in human cell lines only.

The invention relates, in part, on the identification of a new strain of HEV genotype 3 virus. Strain Kernow-C1 (genotype 3) of HEV, which was isolated from a chronically infected patient, was used to identify human, pig and deer cell lines permissive for infection. Adaptation of the Kernow-C1 strain to growth in human hepatoma cells selected for a rare virus recombinant that contained an insertion of 174 ribonucleotides (58 amino acids) of a human ribosomal protein gene and additional mutations. In the context of this invention, in discussing the 174 ribonucleotide insertion identified in the experiments described in the Examples section, the insert into the Kernow virus genome contained 171 ribonucleotides, which could encode only 57 amino acids by itself. However, since it was inserted between ribonucleotides within a codon, its insertion resulted in 58 new amino acids. Therefore, this insertion is referred to herein as having 174 ribonucleotides and encoding 58 amino acids.

Thus, in some embodiments, the invention relates to cDNA clones to develop a vector platform to insert desired sequences into HEV without inactivating the virus. In some embodiments, the invention provides a wild type strain of genotype 3 hepatitis E virus and its cell culture-adapted progeny. In some embodiments, the invention provides a vector comprising sequences of the wild-type strain of the genotype 3 hepatitis E virus described herein. In some embodiments, the invention provides infectious cDNA clones of a replicative genotype 3 hepatitis E virus as described herein, or a chimeric or attenuated virus derived from a replicative genotype 3 hepatitis E virus as described herein, and a cell culture system, e.g., that can be used for studying zoonotic spread of Hepatitis E and for the development of HEV vaccines and immunogenic compositions.

In some embodiments, the invention relates to a vaccine for HEV that comprises sequences from the genotype 3 hepatitis E virus described herein, and attenuated virus derivatives thereof.

In one aspect, the invention relates to an infectious hepatitis E virus (HEV) cDNA clone, wherein the cDNA clone has at least 95% sequence identity to SEQ ID NO:1 and comprises an insert in ORF1 as determined with reference to the HEV nucleotide sequence of SEQ ID NO:5. In some embodiments, the HEV cDNA clone comprises the nucleic acid sequence of SEQ ID NO:1. In some embodiments, the HEV cDNA clone has an insert in the ORF1 sequence that encodes an in-frame amino acid sequence of 20 to 100 amino acids in length. In some embodiments, the insert encodes an amino acid sequence of 30, 35, 40, 41, 42, 43, 44, 45, 46, 47, 48, 49, 50, 51, 52, 53, 54, 55, 56, 57, 58, 59, or 60 amino acids in length. In some embodiments, the insert in the ORF1 has at least 50% identity, or at least 60%, at least 65%, at least 70%, at least 75%, at least 80%, or at least 85% identity to SEQ ID NO:9. In some embodiments, the insert in the ORF1 has at least 90% identity, or at least 95%, at least 96%, at least 97%, or at least 98% identity to SEQ ID NO:9. In some embodiments, the insert comprises the amino acid sequence set forth in SEQ ID NO:9. In some embodiments, the insert is at a position in the HEV ORF1-encoding region where the first amino acid sequence of the insert is amino acid 750, relative to the amino acid sequence set forth in SEQ ID NO:6.

In another aspect, the invention relates to an infectious cDNA clone comprising a hepatitis E virus (HEV) nucleic acid sequence, wherein the clone comprises an insert in the region of the nucleic acid sequence that encodes the hypervariable region of ORF1. In some embodiments, the HEV cDNA clone has an insert in the ORF1 sequence where the insert encodes an in-frame amino acid sequence of 20 to 100 amino acids in length. In some embodiments, the insert encodes an amino acid sequence of 30, 35, 40, 41, 42, 43, 44, 45, 46, 47, 48, 49, 50, 51, 52, 53, 54, 55, 56, 57, 58, 59, or 60 amino acids in length. In some embodiments, the insert in the ORF1 has at least 50% identity, or at least 60%, at least 65%, at least 70%, at least 75%, at least 80%, or at least 85% identity to SEQ ID NO:9. In some embodiments, the insert in the ORF1 has at least 90% identity, or at least 95%, at least 96%, at least 97%, or at least 98% identity to SEQ ID NO:9. In some embodiments, the insert comprises the amino acid sequence set forth in SEQ ID NO:9. In some embodiments, the insert is in the hypervariable region of ORF1, e.g., the insert immediately follows position 749 such that the insertion amino acid sequence starts at position 750, as determined with reference to SEQ ID NO:6. In some embodiments, the infectious cDNA clone is a genotype 3 HEV. In some embodiments, the cDNA clone is a genotype 1 HEV. In some embodiments, the infectious cDNA clones is a genotype 2 or genotype 4 clone.

In a further aspect, the invention relates to a cell culture system comprising cells that comprise an RNA transcript of the cDNA clone of any one of the infectious cDNA clones of the invention, e.g., as described in the preceding two paragraphs.

In an additional aspect, the invention relates to a method of producing a vaccine, the method comprising introducing an RNA transcript from a cDNA clone of the invention, such as a cDNA clone described above, into a cell line, e.g., a human or swine cell line, and obtaining virus produced by the cDNA clone.

In a further aspect, the invention provides viruses that are producted by an infectious HEV clone as described herein, and pharmaceutical compositions comprising such viruses.

In one aspect, the invention relates to a method of producing a vaccine, the method comprising introducing an expression cassette comprising a heterologous nucleic acid sequence encoding an ORF2 having a sequence set forth in SEQ ID NO:4 or SEQ ID NO:8 operably linked to a promoter into a host cell; and obtaining the ORF2 protein.

In a further aspect, the invention relates to a method of producing a vaccine, the method comprising introducing an RNA obtained from an infectious cDNA clone of a genotype 3 HEV into a cell line, wherein the HEV clone comprises an insert of at least 10 amino acid in length in the region of the nucleic acid sequence that encodes the hypervariable region of ORF1 in comparison to the HEV nucleic acid sequence set forth in SEQ ID NO:5; and wherein the RNA is incapable of producing ORF3. In some embodiments, the cell line is a swine or human cell line.

The invention additionally relates to a method of obtaining an HEV strain that has the ability to replicate in cell culture, the method comprising obtaining virus from a chronically infected patient; infecting a cell line in culture, serially passaging the virus, e.g., for at least 3, at least 4, at least 5, at least 6, or more passages; and selecting mutants from a chronically infected patient that replicate in cell culture.

In some embodiments, the invention relates to a method of using HEV virus produced from an RNA transcript of a replicating HEV cDNA clone as an indicator for assessing the HEV viral status of a product of interest. In some embodiments, such a method comprises adding a known amount of an HEV virus as described herein to a material to be analyzed, e.g., blood, water, food; subjecting the material to a process that removes virus, e.g., filtration, heat, etc; and determining the amount of added HEV virus that is present in a sample of the material following the virus removal process. The amount of remaining HEV virus is indicative of the efficacy of the virus removal process.

BRIEF DESCRIPTION OF THE DRAWINGS

FIG. 2. Comparative titration of hepatitis E viruses on human and swine cells. Serial dilutions of each virus were inoculated in triplicate onto human HepG2/C3A cells (solid bars) or LLC-PK1 pig cells (open bars) in 8-well chamber slides. Three days later, slides were coded, immunostained for ORF2 protein, and foci at the endpoint were counted manually. The code was not broken until all samples were counted. Student's t-test p values ranged from 0.006 to 0.016.

FIG. 4. Insertion of a human sequence into the hypervariable region of Kernow-C1. Alignment of human ribosomal gene S17 sequence and that obtained by direct sequencing of RT-PCR product amplified from virus passed 6 times in HepG2/C3A cells. HEV sequences flanking the insert are underlined. (A) nucleotide: HEV (SEQ ID NO:11), S17 (SEQ ID NO:12); (B) amino acid HEV (SEQ ID NO:13), S17 (SEQ ID NO:14).

DETAILED DESCRIPTION OF THE INVENTION

Definitions

Figure 1:
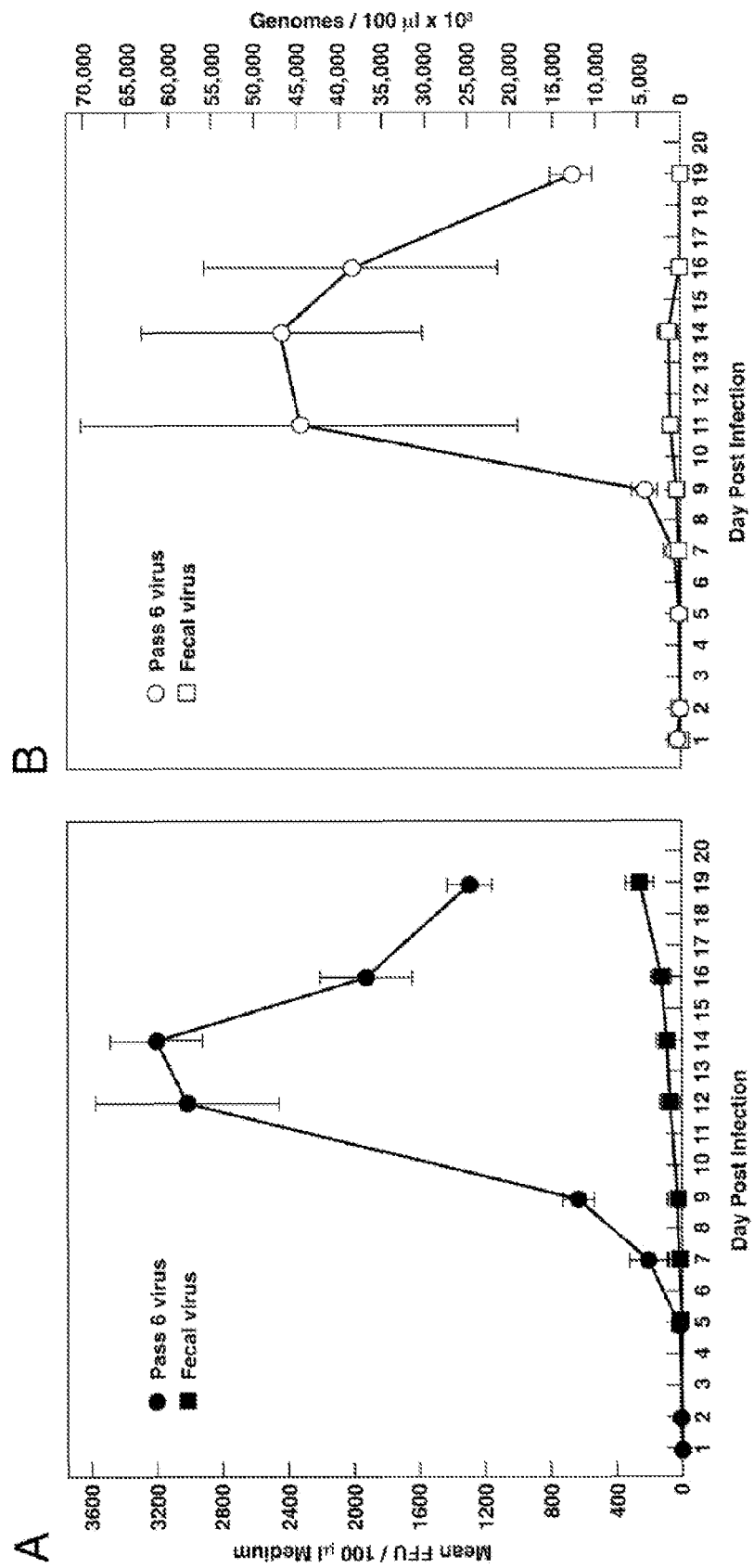
FIG. 1. Adaptation of Kernow-C1 virus to grow in human hepatoma cells. Approximately equal amounts of virus present in the feces (square) or serially passed 6 times in HepG2/C3A cells (circle) were inoculated at a low MOI onto HepG2/C3A cells and infectious viruses (Panel A) and total viruses (Panel B) released into the medium were quantified by focus-forming assay on HepG2/C3A cells and by RT-PCR, respectively. Focus assays of all harvested samples and of the reserved inocula were performed at the same time, in triplicate and under code: direct comparison indicated that the fecal inoculum, which produced many fewer viruses, actually had contained 5 times more infectious virus than the passaged inoculum. Note the difference in scales for the FFU and RNA. Error bars are standard deviation.

The term "hepatitis E virus" ("HEV") as used herein refers to a virus, virus type, or virus class. HEV is classified in the genus Hepevirus and is a positive-sense single-stranded RNA icosahedral virus with a genome 7.2 kb in size with three open reading frames (ORFs) and 5' and 3' cis acting elements. ORF1 codes for methyl transferase, protease, helicase and replicase; ORF2 codes for the capsid protein and ORF3 for a protein of undefined function. There are four major genotypes with a single known serotype.

In the current invention a patient that is "chronically infected" with an HEV virus has an infection of at least six months. The duration of the infection can be measured, e.g., by measuring levels of HEV sequences in the patient, typically by measuring the level of viral RNA in a serum or feces sample.

As used herein, "infectious" with respect to an HEV variant of the invention refers to the ability of the HEV to replicate in culture. In the context of this invention, a cDNA clone is considered to be an "infectious clone" or a "replicating cDNA clone" because it encodes a viral RNA genome that is able to infect and replicate in cells. In typical embodiments, the viral RNA genome is synthesized in vitro from the cDNA clone using a phage polymerase and then the RNA is introduced into cells. In the current invention "infectious" also refers to the ability to replicate in a cell line. For example, when transfecting a cell line, e.g., a human or swine liver or kidney cell line, such as the HepG2 hepatoma cell line or LLC-PK1 kidney swine cell line, obtaining a greater number of transfectants, e.g., at least 10%, at least 20%, at least 50%, at least 75%, or at least 100%, or greater, number of transfectants in comparison to the number obtained with a genotype that has not been modified to include an insert that confers the ability to replicate. In typical embodiments, the levels of ORF2 are assessed to determine the greater number of transfectants. In some embodiments, the number of infectious viruses (peak virus production) is assessed to determine the ability of an HEV variant of the invention to replicate. Well known assays, e.g., focus assays can be employed as a measure of the number of infectious viruses. As used herein, a "replicating" HEV strain is an "infectious" HEV strain; and an "infectious" HEV strain is understood to be a "replicating" HEV strain. Methodology to measure ORF2 production is well known in the art. For example, flow cytometry or fluorescent microscopy can be employed. As understood in the art, although liver and kidney cells may often be used in assessing the ability of a variant of the invention to replicate in culture, other cells, e.g., MRC 5 lung cells, may also be used.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operable linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The phrase "specifically (or selectively) binds" to an antibody or "specifically (or selectively) immunoreactive with," when referring to a protein or peptide, refers to a binding reaction where the antibody binds to the protein of interest. In the context of this invention, the antibody typically binds to an antigen, such as an HEV polypeptide of the invention, with an affinity that is at least 10-fold better than its affinity for other antigens.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another:

1) Alanine (A), Serine (S), Threonine (T);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V); and

6) Phenylalanine (F), Tyrosine (Y), Tryptophan (W).

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated.

The terms "isolated" or "substantially purified", means a chemical composition that is essentially free of other cellular components. Such a composition can be in a homogeneous state although it can be in either a dry or aqueous solution. Purity and homogeneity are typically determined using analytical chemistry techniques such as polyacrylamide gel electrophoresis or high performance liquid chromatography or mass spectrometry. A protein which is the predominant species present in a preparation is substantially purified. Generally, a substantially purified or isolated protein will comprise more than 80% of all macromolecular species present in the preparation. In some embodiments, the protein is purified to represent greater than 90%, 95% of all macromolecular species present or is purified to essential homogeneity, wherein other macromolecular species are not detected by conventional techniques.

The terms "identical" or percent "identity," in the context of two or more nucleic acids or polypeptide sequences, refer to two or more sequences or subsequences that are the same or have a specified percentage of nucleotides or amino acid residues that are the same (e.g., at least 60% identity, optionally at least 65%, at least 70%, at least 75%, at least 80%, at least 85%, at least 90%, at least 95%, at least 97% or at least 99% identity over a specified region), when compared and aligned for maximum correspondence over a comparison window, or designated region as measured using one of the following sequence comparison algorithms or by manual alignment and visual inspection. Alternatively, percent identity can be any integer from 60% to 100%. These definitions also refer to the complement of a nucleic acid sequence.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

A "comparison window," as used herein, includes reference to a segment of any one of the number of contiguous positions in which a sequence may be compared to a reference sequence of the same number of contiguous positions after the two sequences are optimally aligned. Methods of alignment of sequences for comparison are well known in the art.

Examples of an algorithm that is suitable for determining percent sequence identity and sequence similarity are the BLAST and BLAST 2.0 algorithms, which are described in Altschul et al. (*Nuc. Acids Res.* 25:3389-402, 1977), and Altschul et al. (*J. Mol. Biol.* 215:403-10, 1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89:10915, 1989) alignments (B) of 50, expectation (E) of 10, M=5, N=−4, and a comparison of both strands. For purposes of this application, percent identity is typically determined using BLAST2 algorithm set to the default parameters.

"Corresponding to," "reference to", "in comparison to", or "relative to," when used in the context of the positioning of a given amino acid or polynucleotide sequence, refers to the positioning of the residues of a specified sequence of interest when the given amino acid or polynucleotide sequence is compared to the reference sequence. For example, when referring to the positioning of an insert in the hypervariable region of an HEV ORF1 coding sequence, the sequence of interest is aligned with the HEV ORF1 reference sequence and compared to the reference sequence to determine the insertion point in the ORF1 hypervariable region.

The term "a" or "an" is generally intended to mean "one or more" unless otherwise indicated.

Introduction

The invention is based, in part, on the discovery of sequence mutations in a genotype 3 HEV strain that confer the ability to replicate in different cell types in cell culture. The invention thus provides nucleic acid sequences that encode HEV genotype 3 proteins or fragments of HEV genotype 3 proteins that have a biological function, diagnostic and therapeutic reagents, as well as methods of using HEV clones as described herein e.g., for preparing vaccines.

In one aspect, the present invention relates to nucleic acids, specifically cDNAs, encoding the full-length nucleotide sequence of a replicating variant of a hepatitis E virus genotype 3 Kernow strain and variants thereof.

In an additional aspect, the invention relates to modifying a hepatitis E virus strain to increase the ability of the strain to replicate in cell culture by inserting a nucleic acid sequence in-frame into the region of the hepatitis E virus nucleic acid sequence that encodes ORF1, e.g., the hypervariable region of ORF1.

This invention employs routine techniques in the field of recombinant genetics relating to synthesizing polynucleotides encoding a polypeptide of interest and expressing those polynucleotides in an expression system. Generally, the nomenclature and the laboratory procedures in recombinant DNA technology described below are those well known and commonly employed in the art. Basic texts disclosing the general methods of use in this invention include Sambrook & Russell, Molecular Cloning, A Laboratory Manual (3rd Ed, 2001); Kriegler, Gene Transfer and Expression: A Laboratory Manual (1990); and Current Protocols in Molecular Biology (Ausubel et al., eds., 1994-2009 and updates, Wiley Interscience).

Replicating HEV Strains

The present invention relates to HEV cDNAs that are able to replicate in cell culture. In one embodiment, an HEV cDNA of the invention that has the ability to replicate in cell culture has at least 75%, at least 80%, at least 85%, at least 90%, at least 95%, or a at least 96%, at least 97%, at least 98%, or at least 99% identity or greater identity to a cDNA clone having the nucleotide sequence set forth in SEQ ID NO:1. In some embodiments, an HEV cDNA of the invention encodes an HEV ORF1 that has at least 85%, typically at least 90%, at least 95%, at least 96%, at least 97%, at least 98%, or at least 99% identity or greater identity to the ORF1 sequence set forth in SEQ ID NO:2. In some embodiments, a full-length clone in accordance with the invention that has the ability to replicate has at least 75%, at least 80%, at least 85%, at least 90%, at least 95%, or a at least 96%, at least 97%, at least 98%, or at least 99% identity or greater identity to a cDNA clone having the nucleotide sequence set forth in SEQ ID NO:1. and includes an insertion, relative to SEQ ID NO:6, in the hypervariable region of ORF1, which is indicated by underlining in SEQ ID NO:6. In some embodiments, the insertion starts at amino acid 750, as determined with reference to SEQ ID NO:6. In some embodiments, the insertion encodes an amino acid sequence of about 20, about 30, about 40, about 50, about 60, about 70, about 80, about 90, about 100, or about 200 amino acids or greater in length in length. In some embodiments, the insert amino acid sequence is from 50 to 65 amino acids in length. In some embodiments, the insert amino acid sequence is 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 amino acids in length. In some embodiments, the insert amino acid sequence is at least 40, 45, 50, or 55 amino acids in length. In some embodiments, the insert is 58 amino acids in length. In some embodiments the insert has the sequence set forth in SEQ ID NO:9. In some embodiments, the size of the nucleotide insertion that encodes the insert is ORF1 is from about 60 nucleotides to about 300 nucleotides in length.

In some embodiments, a replicating HEV clone of the invention has mutations, relative to SEQ ID NO:5, in the region encoding ORF2. In some embodiments, a replicating HEV clone invention has an insert, relative to the nucleotide sequence set forth in SEQ ID NO:5, in the region encoding the hypervariable region of ORF1 and has additional mutations, relative to SEQ ID NO:5, in the region encoding ORF2.

In further embodiments, the replicating clones of the invention have one or more nucleotide changes encoding 13 amino acid positions in ORF1 relative to SEQ ID NO:6 and/or 2 amino acid positions in ORF2 relative to SEQ ID NO:8. In some embodiments, the replicating clones has an insertion as described herein and one or more additional mutations that encode an amino acid position selected from the positions shown in Table 4 that are mutated in the p6 Kernow virus relative to the original virus.

In some embodiments, a replicating HEV cDNA of the invention comprises an insert in ORF1, typically in the hypervariable region of ORF1. The replicating HEV cDNA can be of any genotype. In some embodiments, an HEV genotype 1 strain comprises an insert in ORF1. In some embodiments, an HEV genotype 3 strain comprises an insert in ORF1. In some embodiments, an HEV genotype 2 or genotype 4 strain comprises an insert in ORF1. An HEV cDNA in accordance with the invention that comprises an insert has an enhanced ability to replicate in cell culture in comparison to the cDNA that does not contain the insert. In some embodiments, the insert is in the hypervariable region of ORF1. In some embodiments, the insertion follows position 749, such that the insertion amino acid sequence starts at position 750 of the ORF1 protein sequence, as determined with reference to SEQ ID NO:6. In some embodiments, the insert encodes a sequence of a ribosomal RNA protein. The insert may, for example, have at least 75%, 80%, 85%, 90%, or 95%, or greater, identity to SEQ ID NO:9.

In some embodiments, an insert in the ORF1 is encoded by the underlined portion of the sequence set forth in SEQ ID NO:10.

A replicating HEV cDNA can be constructed using techniques well known in the art. For example, a full-length cDNA clones may be assembled from cDNA fragments produced by RT-PCR. Such a cDNA clone may then be transcribed to obtain an RNA for transfecting into cells.

As noted above, the invention encompasses variants of the reference cDNA sequences provided as examples, e.g., SEQ ID NO:1, that retain the ability to replicate in a variety of cell lines in culture. Further, as understood in the art, due to the degeneracy of the genetic code, it is understood that numerous choices of nucleotides may be made that will provide a DNA sequence capable of directing production of the HEV open reading frames.

Polypeptides Encoded by an HEV cDNA of the Invention

In an additional aspect, the invention provides a polypeptide encoded by a replicating HEV cDNA clone of the invention and methods of producing such polypeptides using a replicating HEV cDNA clone of the invention. In some embodiments, such a polypeptide may be fully or partially purified from hepatitis E virus produced by cells transfected with nucleic acid sequence of the invention. In another embodiment, the polypeptide or polypeptides are produced recombinantly from a fragment of the nucleic acid sequences of the invention. In yet another embodiment, the polypeptides are chemically synthesized. The polypeptides of the invention, especially structural polypeptides, can serve as immunogens in the development of vaccines or as antigens in the development of diagnostic assays for detecting the presence of HEV in biological samples.

In some embodiments, the invention provides a polypeptide, or a fragment, having an ORF1 amino acid sequence set forth in SEQ ID NO:2 or SEQ ID NO:6; an ORF2 amino acid sequence set froth in SEQ ID NO:4 or SEQ ID NO:8; or an ORF3 amino acid sequence set forth in SEQ ID NO:3 or SEQ ID NO:7; or a fragment or variant thereof. In some embodiments, a polypeptide of the invention has a sequence at least 90%, 95%, or 100%, or greater to an ORF2 protein of SEQ ID NO:4 or SEQ ID NO:8. In some embodiments, a polypeptide of the invention has a sequence at least 95%, typically at least 96%, 97%, 98%, or 99%, or greater, amino acid sequence identity to a fragment of an ORF2 protein of SEQ ID NO:4 or SEQ ID NO:8, wherein the fragment is at least at least 200, at least 300, at least 400, at least 500, or at least 600 amino acids in length. In some embodiments, a polypeptide of the invention has a sequence at least 85%, at least 90%, at least 95%, typically at least 96%, 97%, 98%, 99%, or greater to a fragment of an ORF1 protein of SEQ ID NO:2 or SEQ ID NO:6, wherein the fragment is at 100, at least 200, at least 300, at least 400, at least 500, at least 700, at least 1000, or at least 1500 amino acids in length. In some embodiments, the invention provides a polypeptide comprising the amino acid sequence of SEQ ID NO:2, SEQ ID NO:6, SEQ ID NO:4, SEQ ID NO:3, or SEQ ID NO:7.

A polypeptide of the invention may be used, e.g., for diagnostic and prognostic purposes. For example, in some embodiments, a polypeptide of the invention may be used as an immunogen to stimulate the production of antibodies.

Vectors and Host Cells

A replicating virus of the invention may be cultured in any number of host cells. For example, in some embodiments, RNA is obtained from a replicating a cDNA clone of the invention and is introduced into a cell line, e.g., a human, swine, or rodent liver cell line. In some embodiments, the cell line may be a liver or kidney cell line, but other cell lines, e.g., a lung cell lines may also be employed. In some embodiments, a replicating cDNA clone may be introduced into primary cell cultures, e.g., a primary culture of hepatocytes. The RNA then produces infectious virus. In some embodiments, primary hepatocytes can be cultured, and then infected with HEV, or the hepatocyte cultures may be derived from the livers of infected animals. In addition, various immortalization methods known to those of skill in the art can be used to obtain cell-lines derived from hepatocyte cultures. For example, primary hepatocyte cultures may be fused to a variety of cells to maintain stability.

The infectivity of a cDNA clone of the invention may be assessed using a variety of assays. For example, in some embodiments, once RNA obtained from the cDNA clones has been introduced into cells, expression of a protein, e.g., ORF2 may be assessed. In alternative embodiments, RNA transcripts produced during viral replication initiated by introduction of the initial RNA copy of the cDNA may be assessed.

In typical embodiments, the replicative ability of an HEV clone of the invention is assessed by determining the number of transfectants obtained with the HEV clone (i.e, obtaining using an RNA copy of the cDNA clone). Variant cDNA clones of this invention that have an insert in ORF1 that are considered to be replicating cDNA clones have at least a 10% more, typically, at least 20% more, or at least 30%, 40%, 50%, 80%, or 100%, or more greater number of transfectants that express ORF2 compared to a version of the same cDNA clone that lacks the insert when assayed in a cell line, e.g., HepG2, or other cell line. In the context of the invention, a "replicating" cDNA clone is typically not introduced directly into the cell line, but is used for in vitro transcription. The RNA obtained from the transcription is introduced into the cell lines. One of skill in the art understands that alternative endpoints to measuring ORF2 levels may also be measured, e.g., peak production of virus particles.

In one embodiment, human cells may be grown in vitro and transfected with a nucleic acid of the invention. The human cell may then be assessed to determine if the cells show any indication of HEV infection. Such indications include the detection of viral antigens in the cell, for example, by immunofluorescence procedures commonly known in the art; the detection of viral polypeptides by Western blotting; and the detection of newly transcribed viral RNA within the cells via methods such as RT-PCR. The presence of live, infectious virus particles following such tests may also be shown by injection of cell culture medium or cell lysates into healthy, susceptible animals, with subsequent exhibition of the symptoms of HEV infection.

In some embodiments, an infectious nucleic acid of the invention may be introduced into a host animal, such as swine, for example to assess the virulence of an HEV clones. The virulence phenotype of the virus produced by transfection of the infectious nucleic acid sequence can be evaluated by methods known in the art, e.g., by measurement of liver enzyme levels (alanine aminotransferase (ALT) or isocitrate dehydrogenase (ICD)) or by histopathology of liver biopsies.

In one embodiment, a nucleic acid encoding a polypeptide of the invention may be incorporated into an expression cassette for expression in a host cell. Expression systems are well known in the art and include, e.g. bacteria, such as *E. coli*; yeast, insect cells or mammalian cells. Expression vector include viral-based vectors as well as plasmid vectors. In some embodiments, the HEV polypeptides and peptides are expressed in a human host cell.

In further embodiments, the invention also relates to "chimeric nucleic acid sequences" that are comprised of HEV sequences from different strains. Thus, in one embodiment, a chimeric nucleic acid sequence may have a sequence from an infectious clone of the invention, e.g., a polynucleotide encoding ORF1 from a replicating cDNA clone as described herein, and a sequence, e.g., a polynucleotide encoding ORF2, from another HEV strain. Such chimeric sequence can be produced by standard techniques.

In some embodiments, all or part of a gene or of the 5' or 3' nontranslated region contained in an infectious nucleic acid sequence may be deleted. Such a sequence may then be transfected into a host cell (animal or cell culture) with the mutated sequence. Viral replication can be measured using known methods, such as RT-PCR. In some embodiments, deletions of the central portion of an HEV gene are made, e.g., to conserve the cleavage site boundaries that exist between proteins in the HEV polyprotein and that are involved in proper processing of the polyprotein.

In some embodiments, nucleic acid sequence of the invention are designed to have optimized codons for expression in a cell culture system, e.g., a mammalian cell culture system. For example, codons may be selected to increase the rate at which expression of the peptide/polypeptide occurs in a particular prokaryotic or eukaryotic host in accordance with the frequency with which particular codons are used by the host. In some embodiments, codons are selected to produce RNA transcripts that have desired properties such as a greater half-life.

In one embodiment, animal cells (e.g., human cells) transfected with the nucleic acid sequences of the invention are cultured in vitro and the cells are treated with a candidate antiviral agent (a chemical, peptide etc.) for antiviral activity by adding the candidate agent to the medium. A sufficient period of time is then allowed to pass for infection to occur, following which the presence or absence of viral replication is determined versus untreated control cells by methods known to those of ordinary skill in the art. Such methods include, but are not limited to, the detection of viral antigens in the cell, for example, by immunofluorescence procedures well known in the art; the detection of viral polypeptides by Western blotting using antibodies specific therefor; the detection of newly transcribed viral RNA within the cells by RT-PCR; and the detection of the presence of live, infectious virus particles by injection of cell culture medium or cell lysates into healthy, susceptible animals, with subsequent exhibition of the symptoms of HEV infection. A comparison of results obtained for control cells (treated only with nucleic acid sequence) with those obtained for treated cells (nucleic acid sequence and antiviral agent) indicates, the degree, if any, of antiviral activity of the candidate antiviral agent. Of course, one of ordinary skill in the art readily understands that such cells may be treated with the candidate antiviral agent either before or after exposure to the nucleic acid sequence of the present invention so as to determine against what stage, or stages, of viral infection and replication said agent is effective.

Isolation of Replicating Viruses

The invention additionally provides a method of obtaining replicating viruses using chronically infected HEV patients as the additional source of the virus. In typical methods, virus is isolated from the patient, typically a fecal sample, and is used to infect a cell line, e.g., a hepatoma cell line. Method of serial passaging of viruses to adapt a virus to cell culture are well known in the art. For example, viruses may be passaged using the following protocol. Fecal material is obtained and homogenized to produce a suspension the suspension is clarified by centrifugation and the clarified suspension is used (or the virus may be further purified by ultracentrifugation, after which it can be diluted in the medium of choice). An aliquot of the fecal suspension or serum is overlaid onto a drained monolayer of cells (e.g., HepG2/C3A) in a small culture dish or flask and incubated (e.g., for [5 hours] in a $CO_2$ incubator at a temperature of around 34.5° C. The inoculum is aspirated and cell culture medium is added. Incubation is continued at the same temperature. Medium is removed and replaced once or twice weekly and the collected medium is titered for the amount of virus able to infect HepG2/C3A or another desired cell line, e.g., LLC-PK cells. When the virus titer in the medium has risen to a high enough level (e.g., 1000 focus forming units per mL) an aliquot is removed and used to inoculate another flask or dish of the cells (e.g., HepG2 cells) and this procedure is repeated, e.g., five times, until the desired titer of virus in the medium is reached.

To obtain a cDNA clone, viral RNA in an aliquot of medium is extracted, and reverse transcribed into cDNA which is amplified by PCR, usually as overlapping fragments, and cloned. A T7 polymerase promoter is incorporated into the 5' end of the genome and a unique restriction site is incorporated into the 3' end as part of the PCR primers. The cDNA fragments are digested with the appropriate restriction enzymes and ligated together to produce the full-length virus genome cDNA. The cDNA is amplified in *E. coli*, purified and linearized at the unique restriction site. The linearized cDNA is transcribed in vitro with T7 polymerase. This RNA can then be used to transfect cells and produces the replicating viral genome, viral proteins and infectious virus particles.

One of skill understands that there are many variations to these protocols. The protocols outlined above for serial passaging and cDNA clones are examples of protocols and not intended to limit the protocol employed.

Uses of HEV cDNAs, Viruses, and Proteins of the Invention

The hepatitis E viruses produced using the cDNA clones of the invention may be purified or partially purified from the transfected cells by methods known to those of ordinary skill in the art. In a preferred embodiment, the viruses are partially purified prior to their use as immunogens in the pharmaceutical compositions and vaccines of the present invention.

The present invention therefore relates to the use of the hepatitis E viruses produced from the HEV nucleic acid sequences of the invention, e.g., an HEV type 3 strain having an insert in the ORF1 relative to SEQ ID NO:5 (such as an HEV type 3 having a sequence set forth in SEQ ID NO:1, or a variant thereof), as immunogens in live or killed (e.g., formalin inactivated) vaccines to prevent hepatitis E in a mammal. In some embodiments, the HEV type 3 strain virus has an ORF3 that is not operational. In such an embodiment, the ORF3 may be inactivated by mutation or deletion.

The present invention further relates to the use of recombinant HEV proteins as diagnostic agents and vaccines. The vaccine, which acts as an immunogen, may be a cell, cell lysate from cells transfected with a recombinant expression vector or a culture supernatant containing the expressed protein. Alternatively, the immunogen is a partially or substantially purified recombinant protein.

In one embodiment, a vaccine is administered using direct gene transfer. This may be accomplished via administration of a eukaryotic expression vector containing a nucleic acid sequence of the invention. In some embodiments, the nucleic acid sequence is a replicating cDNA that encodes an infectious hepatitis E virus. As understood in the art, a cDNA or preferably an RNA produced from an infectious HEV cDNA clone of the invention, may be used to transfect a mammal, e.g., by direct injection into the liver tissue of the mammal as described in the Examples. In some embodiments, the immunogen is a polynucleotide of SEQ ID NO:1 or SEQ ID NO:5, or a variant thereof. Expression vectors suitable for producing high efficiency gene transfer in vivo include retroviral, adenoviral and vaccinia viral vectors. Expression vector can be administered by any number of methods, including intravenously, intramuscularly, subcutaneously, intraperitoneally and orally.

In some embodiments, direct gene transfer may be accomplished via intramuscular injection of, for example, plasmid-based eukaryotic expression vectors containing a nucleic acid sequence capable of directing host organism synthesis of HEV proteins. Such an approach has previously been utilized to produce the hepatitis B surface antigen in vivo and resulted in an antibody response to the surface antigen (Davis, H. L. et al. (1993) Human molecular Genetics, 2: 1847-1851; see also Davis et al. (1993) Human Gene Therapy, 4: 151-159 and 733-740).

The invention also relates to the use of the HEV nucleic acid sequence of the present invention, e.g., SEQ ID NO:1 or SEQ ID NO:5, or a variant thereof, to produce attenuated viral strains via passage in vitro or in vivo of the virus produced by transfection with the infectious nucleic acid sequence.

In some embodiments, a polypeptide produced from the nucleic acid sequences of the invention or fragments thereof, e.g., a capsid polypeptide encoded by ORF2, may be employed, e.g., as an immunogen. In one embodiment, polypeptides of the present invention can be recombinantly produced by synthesis from the nucleic acid sequences of the invention or isolated fragments thereof, and purified, or partially purified, from transfected cells using methods already known in the art. In an alternative embodiment, the polypeptides may be purified or partially purified from viral particles produced via transfection of a host cell with the nucleic acid sequences of the invention.

When used as immunogens, the nucleic acid sequences of the invention, or the polypeptides or viruses produced from the nucleic acid sequences, are preferably partially purified prior to use as immunogens in pharmaceutical compositions and vaccines of the present invention. When used as a vaccine, the nucleic acid sequences; and the polypeptide and virus products of the nucleic acid sequences, can be administered alone or in a suitable diluent, including water, saline, or a common buffered medium. The vaccine according to the present invention may be administered to an animal, such as a mammal, and especially a human, by a variety of routes, including, intradermally, intramuscularly, subcutaneously, or in any combination thereof.

Suitable amounts of material to administer for prophylactic and therapeutic purposes will vary depending on the route selected and the immunogen (nucleic acid, virus, polypeptide) administered. One skilled in the art will appreciate that the amounts to be administered for any particular treatment protocol can be readily determined without undue experimentation. The vaccines of the present invention may be administered once or periodically until a suitable titer of antibodies against HEV appear in the blood. For a nucleic acid immunogen, a suitable amount of nucleic acid sequence to be used for prophylactic purposes can be in the range of from about 100 µg to about 5 to 10 mg, often in the range of from about 500 μg to about 2 mg. For a polypeptide, a suitable amount to use for prophylactic purposes can be from 100 ng to 100 μg. When using a virus as an immunogen, the amount administered can be from about $10^2$ to about $10^6$ infectious doses. Such administration preferably occurs prior to any sign of HEV infection.

The formulations of the present invention, both for veterinary and for human use, comprise an immunogen as described above, together with one or more pharmaceutically acceptable carriers and optionally other therapeutic ingredients. The carrier (s) must be "acceptable" in the sense of being compatible with the other ingredients of the formulation and not deleterious to the recipient of the pharmaceutical composition. The formulations may conveniently be presented in unit dosage form and may be prepared by any method well-known in the pharmaceutical art.

Formulations of vaccines comprise the active ingredient with a carrier which constitutes one or more accessory ingredients. Formulations suitable for intravenous, intramuscular, subcutaneous, or intraperitoneal administration conveniently comprise sterile aqueous solutions of the HEV nucleic acid, polypeptide, or virus with solutions that are isotonic with the blood of the recipient. Such formulations may be conveniently prepared by dissolving the solid active ingredient in water containing physiologically compatible substances such as sodium chloride, glycine, and the like, and having a buffered pH compatible with physiological conditions to produce an aqueous solution, and rendering said solution sterile. These may be present in unit or multi-dose containers, for example, sealed ampules or vials.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and, in some embodiments, e.g., at a concentration of 25%-75%.

For aerosol administration, the polypeptides or nucleic acids are supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

Compositions may include a carrier, excipient or adjuvant. Adjuvants include, for example, aluminum hydroxide, lipid A, killed bacteria, polysaccharide, mineral oil, Freund's incomplete adjuvant, Freund's complete adjuvant, aluminum phosphate, iron, zinc, a calcium salt, acylated tyrosine, an acylated sugar, a CpG oligonucleotide, a cationically derivatized polysaccharide, an anionically derivatized polysaccharide, a polyphosphazine, a biodegradable microsphere, TLR agonists, a monophosphoryl lipid A, MF59, oil in water emulsions AS03 and AS04, ISCOM, and quil A.

Suitable formulations for use in the present invention are found in *Remington: The Science and Practice of Pharmacy*, 21st Edition, Philadelphia, Pa. Lippincott Williams & Wilkins, 2005.

When the nucleic acids, viruses and polypeptides of the present invention are used as vaccines or inocula, they normally exist as physically discrete units suitable as a unitary dosage for animals, such as mammals, preferably humans, wherein each unit contains a predetermined quantity of active material calculated to produce the desired immunogenic effect in association with the required diluent. The dose of said vaccine or inoculum is administered at least once. In order to increase the antibody level, one or more booster doses may be administered at some time after the initial dose. For example, booster dose (s) are often administered at some time between about 2 weeks to about 6 months following the initial vaccination. Subsequent doses may be administered as indicated. Amounts of the vaccine and dosing schedules effective for this use will depend upon a variety of factors including the e patient's health, age, weight, administration route, etc.

In one embodiment, the expressed recombinant proteins of this invention can be used in immunoassays for diagnosing or prognosing hepatitis E in a mammal, e.g., humans, chimpanzees, other primates, swine, and the like. In one embodiment, the immunoassay is useful in diagnosing hepatitis E infection in humans.

Essentially any assay can be used that detects the interaction of a HEV polypeptide with an antibody or fragment thereof in a biological sample. Biological samples include blood, serum, tissue, urine samples, and biopsy samples. One or more of the polypeptides may be attached to a solid substrate such as a bead, ELISA plate, dipstick, or microarray.

The presence or absence of the antibody in the biological sample can be determined using methods known to those of skill in the art to detect the antigen antibody complex. Such methods include contacting the antibody antigen complex with a detectably labeled moiety that will bind to the antigen antibody complex and not to antibody or antigen alone.

The nucleic acid sequences, viruses and polypeptides of the present invention can also be administered for purposes of therapy, where a mammal, e.g., a human, is already infected, as shown by well known diagnostic measures.

When the nucleic acid sequences, viruses or polypeptides of the present invention are used for such therapeutic purposes, much of the same criteria applies as when it is used as a vaccine, except that inoculation occurs post-infection. Thus, when the nucleic acid sequences, viruses or polypeptides of the present invention are used as therapeutic agents in the treatment of infection, the therapeutic agent comprises a pharmaceutical composition containing a sufficient amount of said nucleic acid sequences, viruses or polypeptides so as to elicit a therapeutically effective response in the organism to be treated. The amount of pharmaceutical composition to be administered may vary depending on the immunogen contained therein (nucleic acid, polypeptide, virus) and on the route of administration.

In some embodiments, anti-HEV antibodies may be administered to an individual. Thus, antibodies reactive with the HEV proteins of the invention can be passively administered alone or in conjunction with another anti-viral agent to a host infected with an HEV to enhance the immune response and/or the effectiveness of an antiviral drug.

Screening Assays

The present invention also relates to the use of cDNA sequences and polypeptides of the present invention to screen potential antiviral agents for antiviral activity against HEV. Such screening methods are known by those of skill in the art. Generally, the antiviral agents are tested at a variety of concentrations, for their effect on preventing viral replication in cell culture systems which support viral replication, and then for an inhibition of infectivity or of viral pathogenicity (and a low level of toxicity) in an animal model system.

In a further embodiments the nucleic acid sequences of the invention may be useful in identifying sequences critical for cell culture adaptation of HEV and hence, may be useful in identifying cell lines capable of supporting HEV replication.

In another aspect, the present invention involves a method of screening a library of molecules or compounds with an HEV-encoding polynucleotide to identify at least one molecule or compound therein which specifically binds to the HEV polynucleotide sequence. Such a method includes a) combining an HEV-encoding polynucleotide of the present invention with a library of molecules or compounds under conditions to allow specific binding; and b) detecting specific binding, thereby identifying a molecule or compound, which specifically binds to an HEV-encoding polynucleotide sequence, wherein the library is selected from DNA molecules, RNA molecules, artificial chromosome constructions, PNAs, peptides and proteins.

Uses in Processes to Assess Viral Clearance

In some embodiments, virus produced from an infectious cDNA clone of the invention, e.g., an HEV type 3 virus having an insert, e.g., that encodes an amino acid sequence set forth in SEQ ID NO:9, in the hypervariable region of ORF1 as described herein, can be used to assess the efficacy of a virus treatment procedure that removes or inactivates viruses, such as HEV viruses, that may be present in a product. In some embodiments, the product is water; food (which as used here, includes liquids) for animal consumption, e.g., food for human consumption; or blood. In such embodiments, a known amount of HEV type 3 virus produced using a replicating cDNA clone of the invention is introduced into a material to be analyzed, e.g., water, food, or blood; the material is subject to the process that is used to remove and/or or inactivate viruses, e.g., filtration, heat treatment, irradiation, or the like; and the amount of the added HEV type 3 virus that remains in the material is determined following the virus removal and/or inactivation process. The level of remaining HEV type 3 virus is indicative of the efficacy of the virus treatment procedure.

The level of remaining HEV type 3 virus in the product subjected to the virus treatment procedure may be determined using any method known in the art, e.g., using an immunoassay or PCR assay. In some embodiments, the level of remaining HEV type 3 virus is assessed using quantitative PCR. For example, the level of remaining HEV type 3 virus may be determined using primers and/or probes that are specific for the ORF1 insert present in a replicating clone of the invention. In some embodiments, a virus for use in assessing efficacy of a virus treatment1 procedure may comprise additional nucleotide or amino acid sequences that are introduced into the virus genome to use as a marker for identifying the HEV type 3 virus added to the material of interest.

EXAMPLES

Example 1

Genotype 3 Infection of Cells from 10 Different Species

Although certain genotype 3 and 4 strains are known to infect swine and/or deer as well as humans, there are no virus-cell culture systems suitable for exploring host range parameters. In an effort to develop such a system, genotype 3 Kernow-C1 strain of HEV was semi-purified from the feces of an HIV-1 patient infected with HEV (5). The patient had been chronically infected with HEV for two years when his feces were collected and found to contain approximately $10^{10}$ viral genomes per gram. The virus was inoculated onto 5 human and 1 rhesus cell line and 7 days later cells were stained for immunofluorescence microscopy with antibodies to ORF2 capsid protein and to ORF3 protein: since these viral proteins are translated from a subgenomic mRNA, their presence indicates viral RNA synthesis has occurred. Infected foci were found in all 6 cultures but the number of foci was more than 7.5 fold higher in HepG2/C3A human hepatoma cells than in human Huh7.5 or PLC/PRF/5 hepatoma cells, A549 lung carcinoma cells, Caco-2 intestinal cells, or rhesus kidney cells, suggesting that the HepG2/C3A cells were the most permissive.

Semi-purified virus was serially passed 6 times in HepG2/C3A cells for 7 months total. Whereas the virus in feces formed 80 and 90 times more foci on HepG2/C3A cells than on A549 or PLC/PRF/5 cells respectively, by passage 4, the virus produced 400 and 500 times more foci on the HepG2/C3A cells than on these other two cell lines. Growth curves on HepG2/C3A cells comparing production of infectious virus and virion RNA by fecal and passage 6 viruses confirmed that serial passage of the fecal virus had produced a virus able to grow more efficiently in HepG2/C3A cells (p=0.008 for FFU and 0.013 for RNA) (FIG. 1). At day 14 the fecal virus had released 89 FFU and $1.3 \times 10^6$ GE of RNA/100 μL medium to give a specific infectivity of 1 FFU/115,083 GE; on day 14 the pass 6 virus released 3203 FFU and $46.1 \times 10^6$ GE RNA/100 uL to give a specific infectivity of 1 FFU/14,399 GE. Similar attempts to adapt the fecal virus to grow on A549 cells or PLC/PRF/5 cells were unsuccessful.

The fecal virus was tested also for the ability to infect a variety of non-primate cells available from ATCC. Genotype 3 viruses have been isolated from pigs and deer and each of three pig kidney cell lines contained numerous ORF2 and ORF3 stained foci whereas the deer cell line had a moderate number (data not shown). Remarkably, the cow, mouse, chicken, cat, dog and rabbit cell cultures each also contained a few cells stained for both ORF2 and ORF3 proteins as determined by immunofluorescence (data not shown).

Titration of Genotypes 1 and 3 on Human, Pig and Deer Cells.

Figure 2:
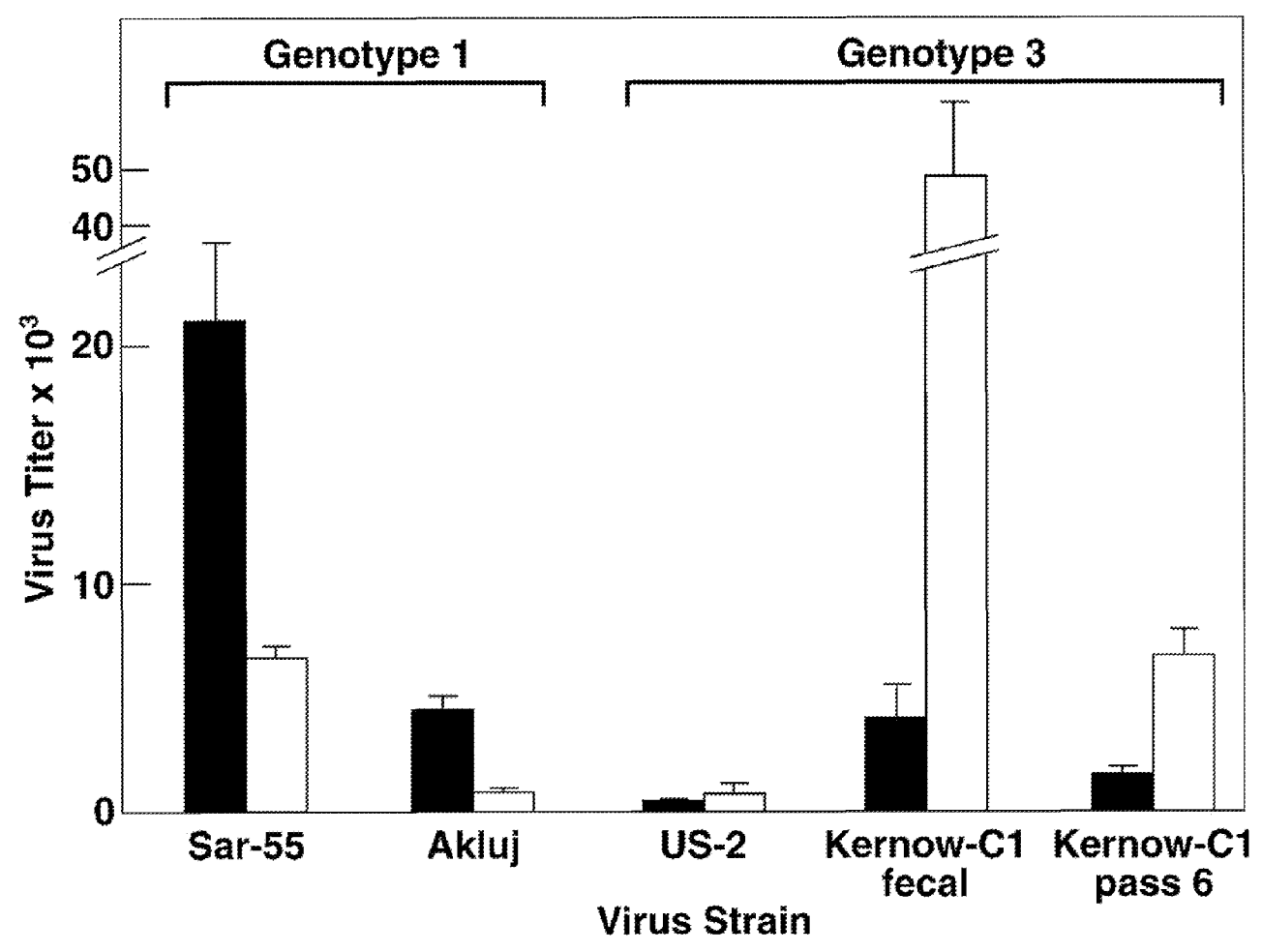

In order to revisit the question of host range restrictions on genotype 1, serial dilutions of the highest titered stocks available of genotypes 1 (Sar-55, Akluj), and 3 (US-2, Kernow-C1 fecal, Kernow-C1 pass 6) were inoculated onto HepG2/C3A, LLC-PK1 pig cells and deer cells and cultures were immunostained for ORF2 and ORF3 proteins 3 days later. The number of ORF2 positive foci at the last 1 or 2 positive dilutions was used to calculate the infectious titer (FIG. 2). As expected, both genotype 1 strains infected HepG2/C3A cells but, surprisingly, they also infected LLC-PK1 cells, albeit less efficiently (p=0.016 for Sar-55 and 0.009 for Akluj). In contrast, both genotype 3 strains infected LLC-PK1 cells more efficiently than they did HepG2/C3A cells (p=0.006 for fecal, 0.010 for pass 6 and 0.008 for US-2). Even though the pass 6 virus was adapted to grow in the HepG2/C3A cells, it still infected more pig cells than human cells. Similar results (with one exception for US-2) were obtained in multiple experiments although the virus titers and, therefore, the ratios varied from experiment to experiment (Table 3). Because of this variation, it is necessary to include at least one genotype 1 and one genotype 3 strain in each assay for comparison (Table 3).

The lower titer of the pass 6 virus compared to that of the fecal Kernow-C1 virus reflects a lower specific infectivity of the cell-cultured virus. Whereas the cultured viruses in FIG. 1 had a specific infectivity of about 1 FFU/15,000 GE on HepG2/C3A cells, the Kernow-C1 virus in the feces had a specific infectivity of 1 FFU/450 GE on these same cells.

Figure 3:
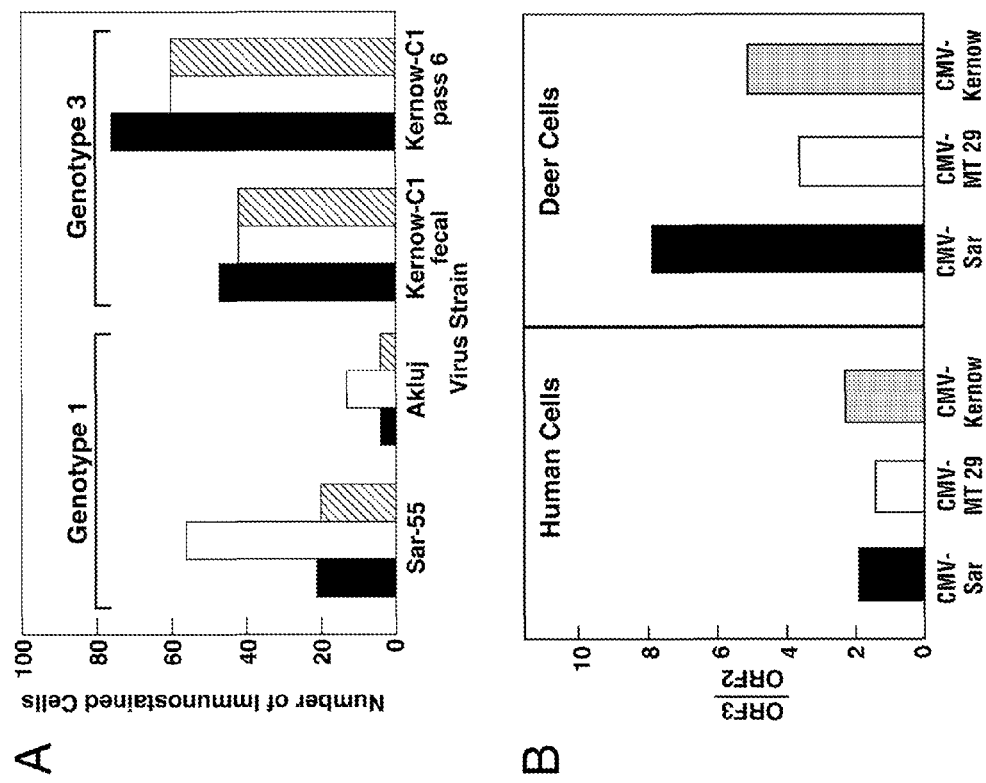
FIG. 3. Differential translation of ORF2 in deer cells. (A) Deer cells were infected with indicated strains, immunostained 3 days later and all cells containing ORF2 protein (solid bars), ORF3 protein (open bars), and both proteins (hatched bars), were counted. (B) Deer cells and S10-3 human cells were transfected with a CMV plasmid expressing a bicistronic mRNA containing the sequence of Sar-55 (CMV-Sar), Kernow-C1 (CMV-Kernow), or the Sar-55 sequence with the first 29 nucleotides replaced with those of Kernow-C1 (CMV-MT29). Two days later, cells immunostained for ORF2 or ORF3 protein were quantified by FACS and the ratio of ORF3 to ORF2 was calculated according to % of cells stained (shown above bars).

The infection of deer cells was more complicated. US-2 did not infect the deer cells in this experiment but each of the other strains did, with a titer 8 to 11 times lower than that on LLC-PK1 cells. Interestingly, dual-staining for ORF2 and ORF3 proteins suggested that genotype 1, but not genotype 3, strains were deficient in ORF2 capsid protein production. All stained deer cells in each well were counted: two thirds of the cells containing genotype 1 ORF3 protein had no detectable ORF2 protein whereas every cell containing genotype 3 ORF3 protein contained ORF2 protein (FIG. 3A). This imbalance was not seen in human cells infected with genotype 1, Sar-55: of 73 cells randomly scored positive for ORF3 protein, only 1 cell lacked detectable ORF2 protein. Because translation of ORF2 and ORF3 initiates from closely spaced methionine codons on the same bicistronic mRNA (16), this result suggested a translation bias towards initiation of ORF3 protein synthesis at the expense of ORF2 protein synthesis in deer cells infected with genotype 1 strain but not in those infected with genotype 3 strains.

Viral protein production in deer cells was not robust enough to permit FACS analysis. Therefore, FACS analysis of cells transfected with CMV promoter-driven mRNAs was performed to confirm the initiation bias. Bicistronic mRNAs of wild-type Sar-55, wild-type Kernow-C1, and Sar-55 with the first 29 nucleotides mutated to that of Kernow-C1 were transiently expressed in S10-3 human hepatoma cells and in deer cells. FACS analysis of cultures stained separately for ORF2 and ORF3 proteins demonstrated that significantly more ORF2 protein relative to ORF3 protein was produced by the mutant CMV-MT29 (p=0.024) and CMV-Kernow (p=0.052) than by CMV-Sar (p=0.003) (FIG. 3B). Since the CMV-Sar and CMV-MT29 differed by only these 29 nucleotides, the increased relative production of ORF2 by the mutant suggested that translation of Sar-55 ORF2 capsid protein was diminished in deer cells. Indeed, when the same 29 nucleotide mutation was introduced into the infectious full-length Sar-55 clone (pSK-E2-MT29) and it and the wild-type Sar-55 transcripts were transfected into deer cells and scored by immune microscopy 5 days later for ORF2 and ORF3 protein production, the average ratio of ORF3/ORF2-containing cells decreased from 3.68 for wild-type to 0.4 for the mutant (p=0.004) thus confirming that the 29 nucleotide genotype 3 sequence at the translation initiation site was sufficient to increase ORF2 production of Sar-55 in deer cells (Table 1). In comparison, a similar ratio of ORF3/ORF2-containing cells was obtained for human S10-3 cells transfected with either the wild-type or mutant clone (Table 2).

Example 2

HepG21C3A-Adapted Virus and Host-Cell Recombination

The RT-PCR consensus sequence of the virus in the feces and at passage 6 was determined. Sixteen amino acid differences (10 in ORF1, 5 in ORF2 and 1 in ORF3) along with an in-frame insert of 58 amino acids in the hypervariable region (HVR) of ORF1 (22) differentiated pass 6 from the fecal virus (Table 4). A Blast search identified the inserted sequence as belonging to the ribosomal 517e superfamily which is highly conserved across species. One hundred sixty seven of 170 nucleotides and 53 of 57 amino acids were identical to those in the human ribosomal protein S17 (GenBank DQ896701.2) (FIG. 4) compared to only 155 of 171 nucleotides in the swine S17 protein (AY5500731.1). RT-PCR with paired HEV and insertion sequence primers detected viral genomes with the insertion in the original fecal suspension indicating that a double-recombination event had occurred either in the patient or in a previous host. It is noteworthy that the recombinant genomes in the feces were a minor species since they were not detected by direct sequencing of the RT-PCR products from the feces or from first-pass virus in the culture medium 70 days post-infection. The entire HVR was amplified from the feces with HEV-specific primers, cloned and sequenced. Of 120 clones sequenced, none contained the insert.

In an attempt to determine whether the inserted sequence or its size was relevant, the insert sequence was cloned in frame into the hypervariable region of the Sar-55 infectious clone in either the sense, reverse, or reverse-complementary orientation and in vitro transcribed genomes were transfected into S10-3 cell. The wild-type genomes and those with the sense orientation of the insert were indistinguishable and produced many more virus-positive cells than could be counted; in contrast, wells containing cells transfected with the genomes containing the reversed and reversed-complementary insert contained only 16 and 12 virus-positive cells respectively as determined by immunofluorescence microscopy (data not shown).

Example 3

Preparation of Clones that Replicate

The complete nucleotide sequence of the Kernow-C1 virus genome present in the semipurified feces of an HIV-1 patient infected with HEV was determined by RT-PCR with Super-Script II Reverse Transcriptase (Life Technologies), Prime-Star HS DNA Polymerase (TAKARA) and 2-Step RT-PCR Kit (QIAGEN) initially using primers derived from the full-length cDNA clone of swine hepatitis E virus, strain 3 (Meng et. al). Subsequent primers were designed based on newly obtained sequences. The extreme 5' sequence was determined by 5'RACE Kit (Life Technologies).

For the construction of a full-length cDNA clone [K I], Kernow-C1 virus RNA was extracted with TRIZOL LS reagent (Life Technologies) from passage 1 virus released into the medium of HepG2 cells that had been inoculated with semi-purified fecal virus. The Kernow-C1 genome was amplified with SuperScript II Reverse Transcriptase (Life Technologies), Herculase HotStart Taq (Stratagene), and PrimeStar HS DNA Polymerase (TAKARA). A total of six overlapping fragments covering the entire Kernow-C1 genome were amplified and joined by fusion PCR into two overlapping fragments which were subsequently ligated together at a unique restriction site present in each fragment. The 5' terminus of the encoded genome was engineered to have a unique XbaI site and a T7 RNA polymerase core promoter. The 3' terminus was engineered to contain a stretch of sixteen adenosines followed by a unique MluI [site for plasmid linearization], which in turn was followed by HindIII. The full-length genomic cDNA was ligated into the pBlueScript SK(+) plasmid (Stratagene) between the XbaI and HindIII sites of the polylinker.

The RT-PCR consensus sequence of passage 6 was determined using a 2-Step RT-PCR kit (QIAGEN) that revealed an in-frame insertion of 58 amino acids in the hypervariable region (HVR). This insertion was identified by Blast search to be most closely related to human ribosomal protein S17.

The fact that virus selected by six serial passages in HepG2/C3A cells was a recombinant virus containing part of a human S17 gene was not discovered until the passage 6 virus was sequenced (above). Although viral genomes containing the 171 nt inserted S17 sequence could be detected in the feces by nested RT-PCR with virus/human primer pairs, they constituted such a minor quasispecies that they were not represented in 120 cDNA clones of the HVR region of viruses in the fecal inoculum (data not shown). In order to determine when in the passage series the virus containing this insert first emerged and when it became the dominant species, the HVR region of viruses in the medium at each of the 6 cell culture passage levels was amplified by RT-PCR, cloned and sequenced.

The results of the sequencing analysis showed that two of 11 clones from the first passage already contained the S17 sequence and from passage 2 onward, it was present in the majority of clones (Table 5). Amazingly, a different mammalian gene insert, 114 nt long, was present in 5 other of the 11 clones from the first cell culture passage and, in this case, an almost identical sequence was found in 2 of the 120 clones from the feces. This 114 nucleotide long sequence lacked 10 nt from the middle of the GTPase activating protein gene sequence and consisted of a rearranged gene segment (GenBank AB384614.1) in which GTPase nt 3009-3105 were followed by GTPase nt 2981-3008 at the 3' end, and the reading frame was changed so that the sequence, as inserted, encoded an unrelated amino acid sequence that did not match with anything when the sequence was searched against all known non-redundant protein data bases. However, this insert was not detected in any of the clones from subsequent passages 2 through 6.

Infectious cDNA Virus Clones.

The medium of cultured cells should contain the members of a virus quasispecies that are best able to infect and complete a replication cycle in these cells. Therefore, the first full-length cDNA clone of the Kernow virus was constructed from uncloned cDNA fragments amplified from the medium (passage 1 virus) of HepG2/C3A cells that had been inoculated 111 days previously with a stool suspension containing the original Kernow strain. This Kernow pass 1 cDNA clone, p1 lacked the S17 insert (GenBank HQ389543) and differed from the consensus sequence of virus in the feces by 15 amino acids (Table 7). It was transfected into S10-3 hepatoma cells which were monitored 5 to 6 days later by immunofluorescence microscopy for cells stained for ORF2 protein. Less than 2% of S10-3 cells transfected with in vitro transcripts of the pass 1 clone produced detectable ORF2 protein, suggesting that this virus genome, although infectious, lacked elements that contributed to robust replication. Incorporation of the S17 insert into the cDNA clone to yield p1/S17 increased the number of cells transfected, although levels remained below ~10%.

Figure 5:
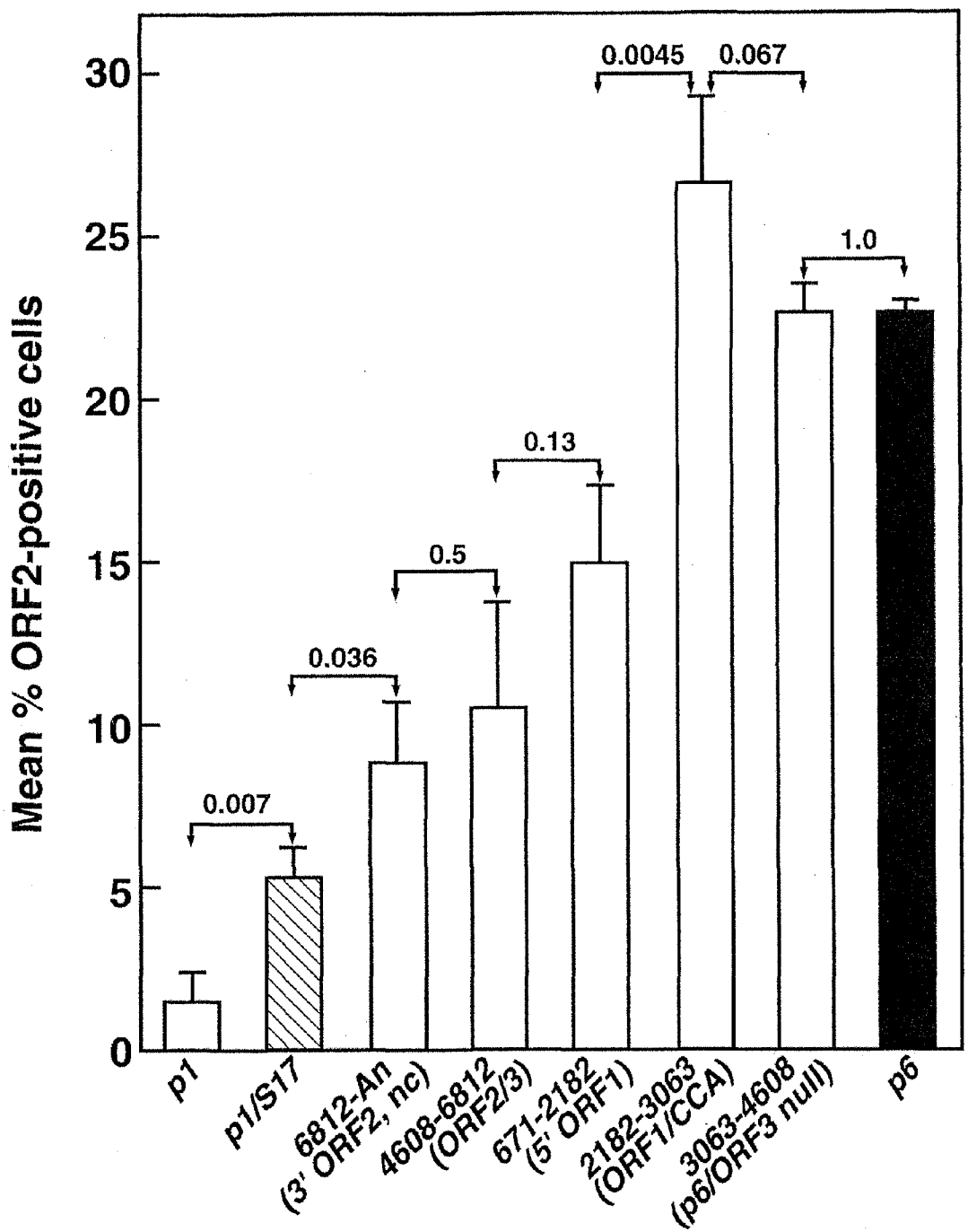
FIG. 5. Transfection of S10-3 cells with sequential plasmid constructs. The restriction fragment noted was replaced with the corresponding fragment amplified from the passage 6 virus quasispecies. The new construct served as the background for the next replacement and the procedure was repeated until all of p1 had been replaced with p6 sequences. All plasmids were transcribed, transfected and immunostained for ORF2 protein in the same experiment: triplicate samples were harvested and tested by flow cytometry 3 days posttransfection. The student's t-test P values are given for adjacent samples. P≤0.05 was considered significant. Error bars indicate standard deviations.

In order to derive a more robust virus and to identify regions which contributed to cell culture adaptation, convenient restriction fragments of p1/S17 cDNAs were sequentially replaced with the quasispecies of uncloned PCR product amplified from pass 6, cell culture-adapted virus (Table 6). Transcripts from multiple clones of these new full-length genomes were transfected into S10-3 cells and examined for ORF2 production by immunofluoresence microscopy. The clone producing the highest percentage of transfected cells was used as the backbone for the next substitution and this process was repeated 4 more times. Finally, all clones were compared by flow cytometry in the same experiment (FIG. 5). The first 3 sequential fragment substitutions had introduced mutations into the 3' ORF2 and non-coding regions (nt 6812-poly A), into the 3' ORF1 and ORF2/ORF3 overlap (nt 4608-6812), and into the 5' third of ORF1 (nt 671-2182): of the three fragments, only the 6812-$A_n$ substitution significantly increased the efficiency of transfection (FIG. 5). Of the pass 6 PCR amplicons spanning nt 4608-6812, the sequence that boosted transfection levels the most contained mutations that eliminated the only 2 methionine codons (aa 1 and 69) in ORF3 (Table 6); immunofluoresence microscopy confirmed that viruses from this cDNA clone and the 3 subsequent cDNA clones did not produce ORF3 protein (data not shown). The pass 6 fragment with the greatest enhancing effect spanned nt2182-3063 and contained 3 naturally-occurring amino acid mutations in the X domain and a single proline deletion in the HVR: additionally 4 proline codons in this fragment were changed by site-directed mutagenesis to CCA codons in order to preserve the amino acid sequence while disrupting a cluster of C residues in the HVR that greatly hindered PCR and sequence analyses. The $5^{th}$ fragment substitution (nt 3063-4608) contained a highly conserved region of the helicase and polymerase genes, did not introduce any amino acid changes and had no obvious effect (p=0.067). Finally, the methionine initiation codon of ORF3 was restored so that ORF3 protein could be produced by the p6 virus. The presence or absence of the methionine codon had no apparent effect on levels of transfection of S10-3 cells [(compare p6/ORF3 null and p6 transfection levels (p=1.0)]. This clone, excluding the insert, differed from the stool consensus sequence by 16 amino acids, from p1 by 25 amino acids, and from passage 6 consensus sequence by only two amino acids (aa 598=R to C in ORF1 and aa 593=T to A in ORF2). Transcripts of the final p6 clone routinely transfected between 10 to 45% of S10-3 cells.

Figure 6:
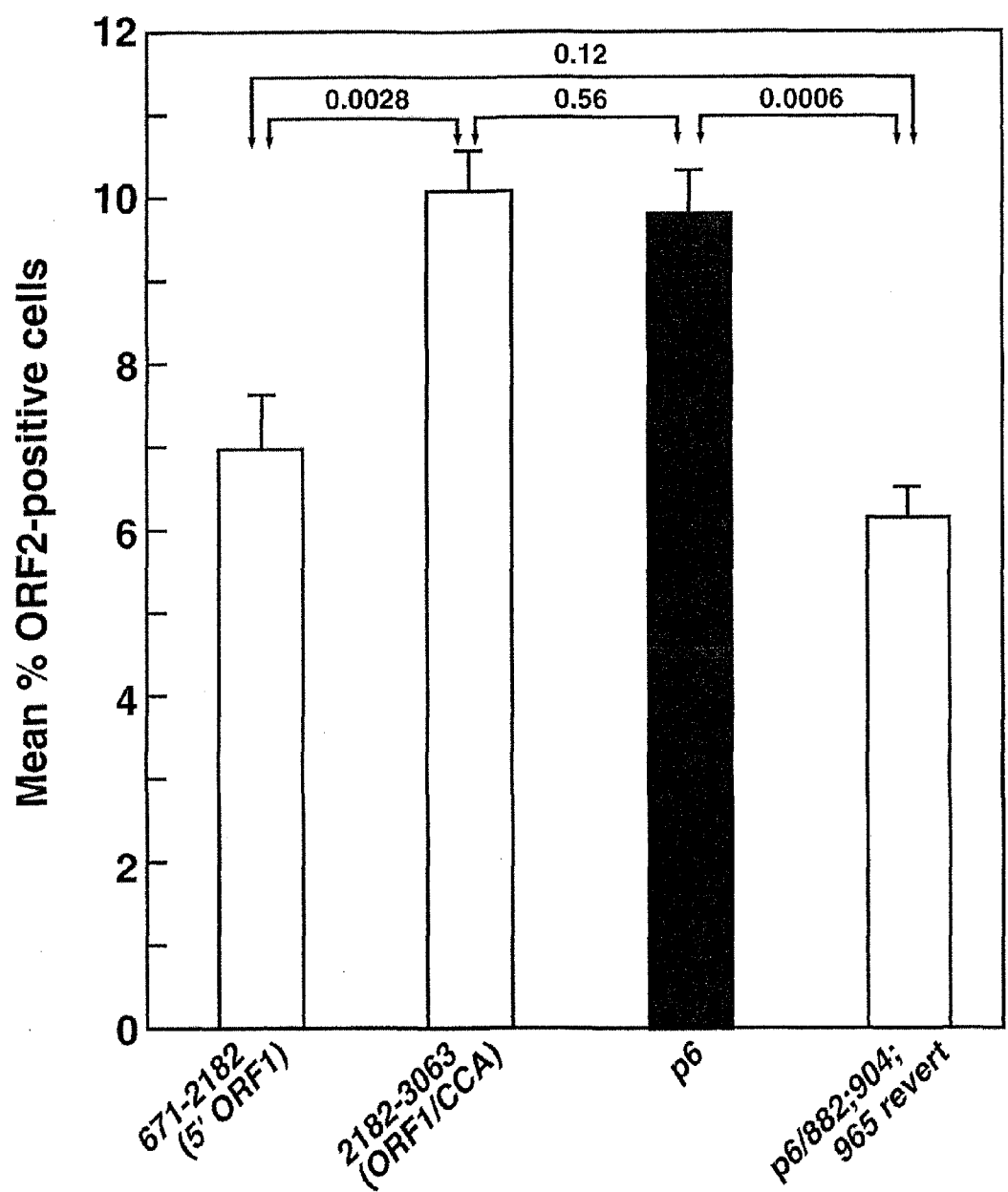
FIG. 6. Reversion of amino acids 882,904 and 965 in the X region reduces the level of transfection. S10-3 cells were transfected with the 5'ORF1 plasmid lacking the CCA and X region mutations, the ORF1/CCA plasmid containing both the CCA and X region mutations, p6, and a revertant plasmid containing the CCA but not the X region mutations. Cells in triplicate samples were immunostained and analyzed by flow cytometry at 6 days posttransfection. P values are given and error bars denote standard deviations.

Because the function of the X domain is unknown and the C to A changes in proline codons of the HVR were engineered rather than natural, it was determined whether the three mutations in the X domain or the C to A synonymous mutations in the HVR in fragment 2182-3063 were the most important for enhancing transfection. Because back-mutation of the proline codons would recreate the sequencing problems, the amino acid codons in the X domain were chosen for back mutation. All 3 mutations in the X domain were back-mutated to the original codons present in the p1 cDNA clone and the level of transfection was quantified by flow cytometry at day 6 post-transfection (FIG. 6). Transcripts from the clone containing the three reverted X domain mutations were significantly (P=0.0006) less efficient than those from the p6 cDNA clone in transfecting S10-3 cells and not significantly different (P=0.12) from the 671-2182 clone which lacked both the HVR proline mutations and the X domain mutations, suggesting that the engineered changes that interrupted the poly C tract had a minimal effect on transfection, whereas one or more of the three mutations in the X region played an important role.

Figure 7:
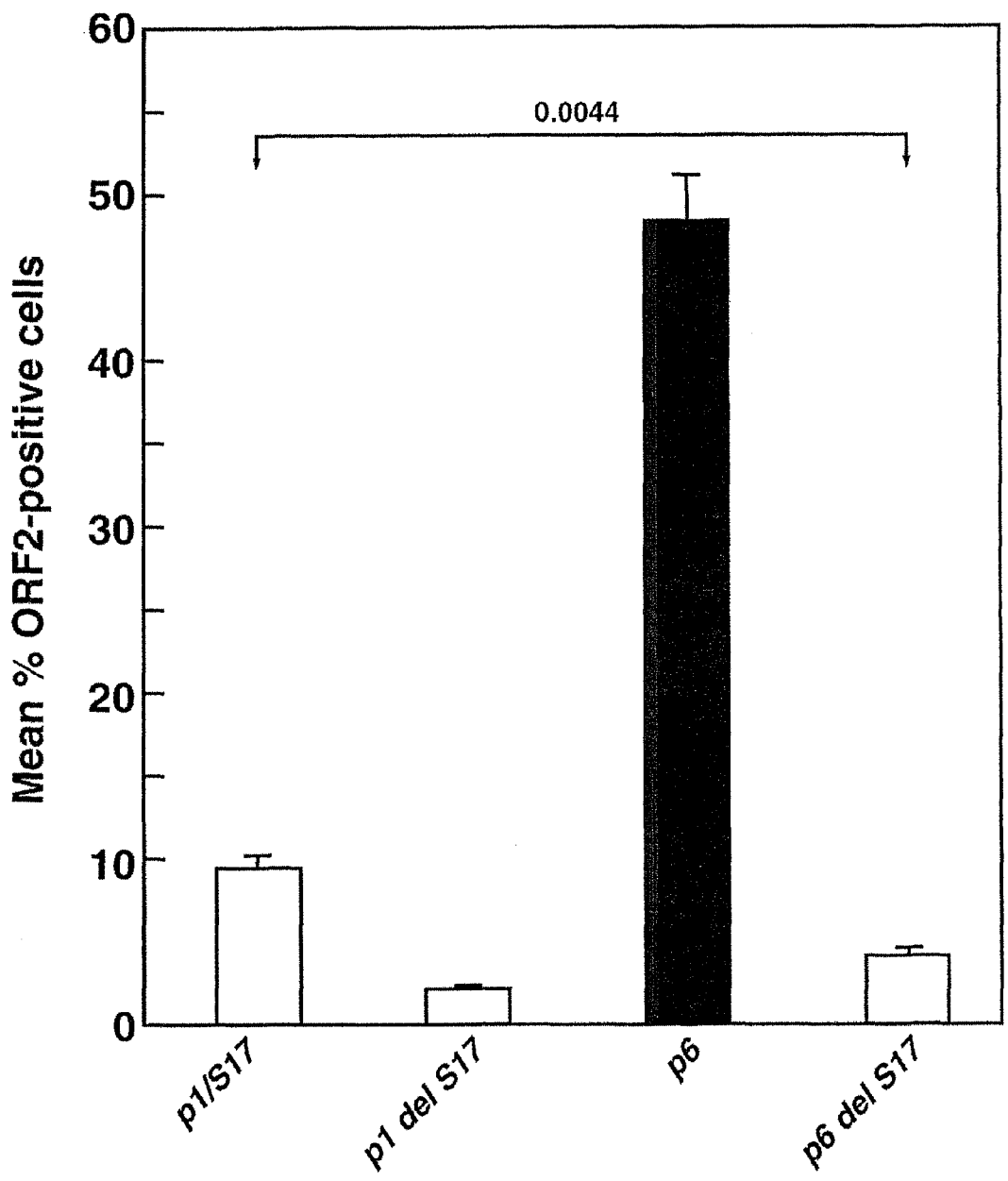
FIG. 7. Removal of S17 sequence from p6 eliminates the adaptive effect of most point mutations. S10-3 cells were transfected with p1 and p6 plasmids with or without S17 sequence. Triplicate samples were analyzed by flow cytometry at day 4 posttransfection. P values were all <0.0001 except for p1/S17 versus p6delS17. Error bars denote standard deviations.

In order to determine if the effect of the S17 sequence was limited to the modest increase in transfection levels observed following its insertion into the p1 cDNA clone, the S17 sequence was selectively removed from the p6 cDNA clone containing all the point mutations to yield p6delS17. Flow cytometry confirmed that addition of S17 sequence to p1 virus genomes significantly increased transfection efficiency by those genomes although levels did not approach those attained by the recombinant p6 genomes (FIG. 7). Surprisingly, removal of the S17 sequence from the p6 cell culture-adapted cDNA clone dramatically decreased the transfection efficiency of the genome transcripts to levels only 3 fold better than those of the p1 cDNA clone (FIG. 7). This result suggested that the point mutations responsible for the incremental improvement in transfection efficiency of the serial clones were mostly ineffective in the absence of S17 sequence.

The flow cytometry analyses based on ORF2 protein immunostaining revealed the percentage of cells that produced detectable ORF2 protein but they did not provide a quantitative comparison of the amount of ORF2 protein produced or of the duration of ORF2 synthesis. In order to confirm and extend the flow cytometry data, the 5' portion of ORF2 was replaced with the in-frame gaussia luciferase reporter gene to yield p6/luc: this luciferase has a signal sequence which results in its secretion and accumulation in the cell culture medium. Therefore, multiple time points can be taken from the same culture.

The luciferase system was validated by measuring the amount of luciferase secreted into the medium by p6/luc virus containing either a functional polymerase or a mutated, non-functional polymerase that could not synthesize viral RNA. Whereas the luciferase signal in medium from S10-3 cells transfected with the p6/luc polymerase mutant or from untransfected S10-3 cells was less than 111 units/24 hr at its peak on day 2, that in the medium of cells transfected with p6/luc rose from 2163 units/24 hr on day 1 to over 36 million units/24 hr on days 4 through 6 (data not shown).

Figure 12:
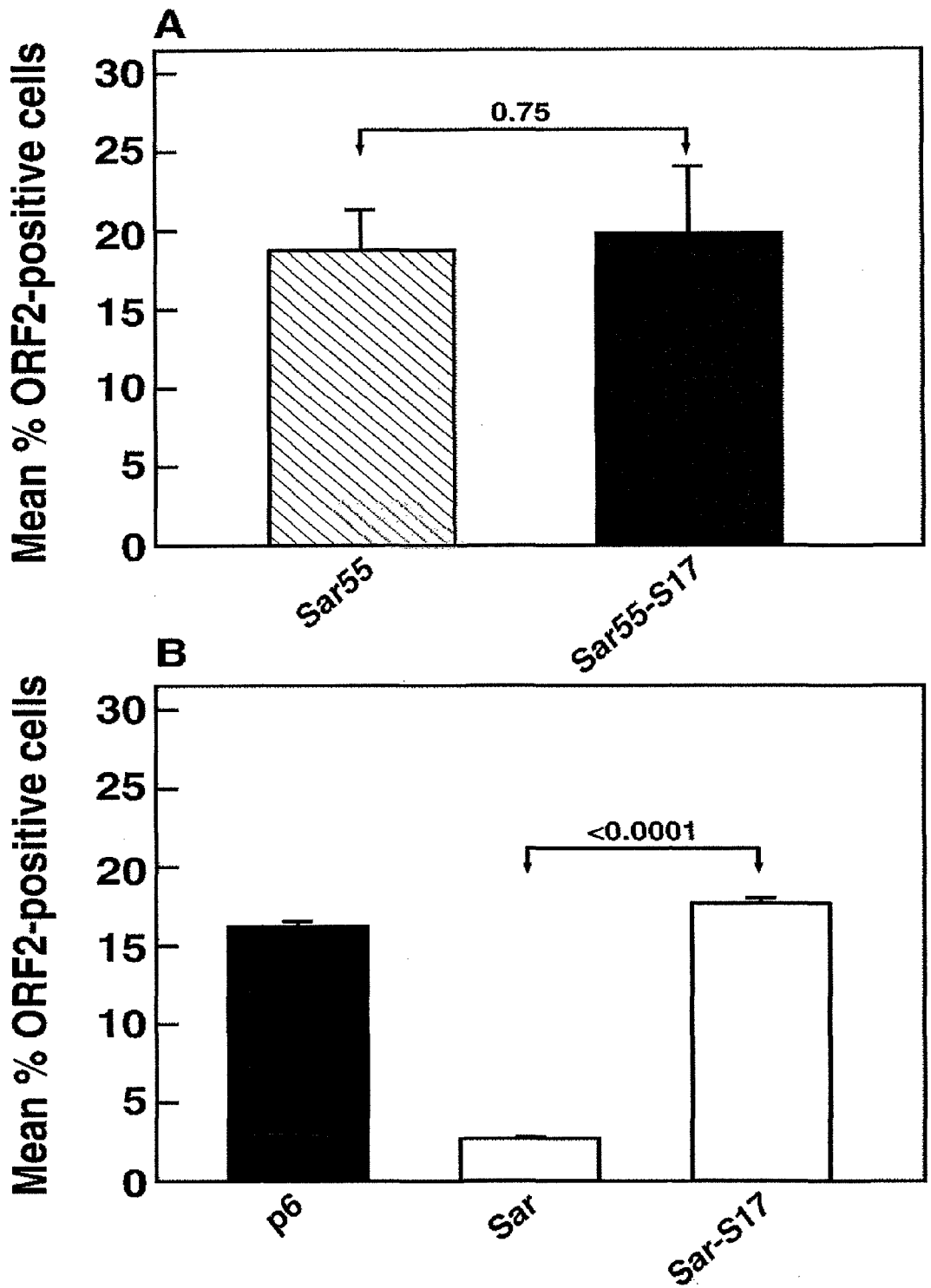
FIG. 12. The effect of the S17 insert on Sar55 transfection of S10-3 and BHK-21 cells. Efficiency of transfection of S10-3 (A) and BHK-21 (B) cells was monitored by flow cytometry.

Therefore, luciferase production requires viral RNA synthesis as predicted based on the ORF2 location of the luciferase gene in the subgenomic mRNA. Luciferase production by p6/luc virus was then compared to that by the p6/luc virus mutated to either delete the S17 insert or to eliminate the three X gene mutations. Production of luciferase by p6/luc virus, either with or without the S17 insert, peaked on day 6 posttransfection, but the ratio of p6/luc units to p6/luc(del S17) units steadily increased and reached 52-fold at day 7, thus confirming that the S17 insert conferred a significant growth advantage and served as a cell culture adaptive mutation (FIG. 8A). In addition, the luciferase data for the three X gene back-mutations was consistent with that from the flow cytometry analyses (FIG. 8B); cultures transfected with the p6/luc X gene revertant produced less luciferase than those transfected with the p6/luc virus. It is interesting to note that, as shown in both FIGS. 8A and 8B, the luciferase values on day 9 decreased substantially for the p6/luc virus but remained near plateau levels for the mutants.

Synonymous Mutations Did not Decrease Transfection.

The enhancing effect of the S17 insert could be due to either the RNA or the protein sequence. In an attempt to distinguish between these possibilities, the third base (93% and 70% of the 58 codons in S17) was changed (purine to purine and pyrimidine to pryimidine) in two clones without altering the encoded AA except for two M to I changes. The number of cells successfully transfected by each of these two clones did not differ significantly from that of p6 (FIG. 9) even though the predicted RNA structures and delta G differed from those of p6 (delta G=−120.38) and each other (delta G=−102.99 and 98.97 for clone #1 and 2 respectively). Therefore, it appeared that the enhancing effect occurred at the protein level.

Effect of Insert Size.

The previous studies demonstrated the importance of the S17 insert for growth of the Kernow virus in cell culture but did not provide any insights into how it functioned. Since the first passage of the stool inoculum had provided evidence for a possible enhancing effect of the GTPase insert on growth of the Kernow strain in cell culture, this insert was substituted for that of the S17 insert in the p6 clone to evaluate its effect. Although the 114 nt GTPase insert increased the number of transfected cells, it was only about half as effective as the 171 nt S17 insert (FIG. 10A). In order to determine if length of the insert per se was a factor, sequence encoding the N-terminal or C-terminal 58 amino acids of green fluorescent protein (GFP) was substituted for the S17 sequence. GFP was chosen because it has been shown to be relatively benign when expressed as a fusion protein with many partners in many cell types. And, indeed, fluorescence microscopy indicated GFP was produced when the entire coding region was fused in-frame to the 3' terminus of the S17 insert (data not shown); however, neither the 174 nt encoding 58 aa of the N-terminual or C-terminal amino acids of GFP had a detectable effect on the levels of transfection of S10-3 cells (FIG. 10A,B). Therefore, number of nucleotides and/or amino acids in itself was not a determining factor. The effect of size was tested also by removing half of the nucleotides from the S17 inserted sequence in p6 to yield 87 to 90 nt of sequence encoding the N-terminal half, the C-terminal half, or the middle portion of the S17 insert. All 3 constructs transfected cells to a similar extent that averaged 2 to 6-fold less than if the entire insert was present and 2.5-fold more than if it was absent (FIG. 10C). Finally, 117 nucleotides of another mammalian gene sequence (S19 ribosomal protein), which we discovered inserted into the HVR of another genotype 3 strain from a different chronically infected hepatitis E patient, was substituted for the S17 sequence in the p6 clone. Although genomes carrying the S19 sequence in this different genotype 3 strain had been selected during culture in HepG2/C3A cells, much as had the S17-containing Kernow genomes, transfer of this sequence from that genotype 3 strain to the Kernow strain resulted only in a modest enhancement. (FIG. 10D).

P6 Encodes a Virus that can Infect Both Swine and Human Cells.

Both the S10-3 cells used for transfection and the HepG2/C3A cells to which the pass 6 virus was adapted are human hepatoma cells so it was important to determine if the p6 virus retained the ability of the original fecal inoculum to grow also in swine cells. Transcripts of p6 and p6del S17 were electroporated into LLC-PK1 swine kidney cells which were assayed by flow cytometry 5 days later. ORF2 protein was produced in swine cells by both constructs demonstrating that both the negative strand genomes and the subgenomic mRNAs had been synthesized by each. Over 31% of the swine cells were transfected by the p6 clone compared to 12% by the p6 clone missing the S17 insert, thus demonstrating that the S17 sequence enhanced transfection of swine cells as it did human cells (FIG. 11A). Next, p6 virus itself was tested for the ability to infect swine cells. Two different lots of p6 virus grown in HepG2/C3A cells were titered in parallel on HepG2/C3A cells and LLC-PK cells (FIG. 11B). In both cases, the infectivity titer was higher on the swine cells than on the human cells but the difference varied for the two preparations and reached significance (p=0.0087) in the first case but not in the second (p=0.064). However, the ratios of titers on LLP-CK cells divided by those on HepG2/C3A cells were 2.4 and 1.5 respectively, which were not substantially different from the ratios of 5.49 and 2.84 reported previously for two preparations of the uncloned pass 6 virus quasispecies. Clearly, the p6 cDNA clone encoded a virus that could infect cultured cells originating from each of the two major host species for genotype 3 HEV.

Effect of S17 Sequence on a Genotype 1 Strain

Transcripts from a genotype 1 cDNA clone, Sar 55, transfected S10-3 cells readily but initial experiments to adapt the virus to grow in cell culture failed. A previous experiment had demonstrated that recombinant Sar55 genomes containing the S17 sequence from p6 virus in their HVR (Sar 55/S17) were able to transfect S10-3 cells, but a quantitative comparison with Sar 55 genomes lacking the insert had not been performed. Therefore, Sar55 and Sar 55/S17 transcripts were transfected into S10-3 cells which were subjected to flow cytometry 5 days later. Both sets of transcripts produced a similar number of ORF2-positive cells, suggesting that the S17 sequence neither enhanced nor diminished transfection efficiency of Sar55 genomes in this system (FIG. 12A).

Since the Kernow virus had displayed such a diverse host range previously (see, above examples), p6 transcripts were tested for the ability to transfect hamster BHK-21 cells and were found to produce ORF2-positive cells, although with low efficiency (3.8% compared to 30.1% for BKH-21 and S10-3 respectively). Therefore, the Sar 55 and Sar-55/S17 transcripts also were tested by flow cytometry for the ability to transfect BHK-21 cells even though these cells were an unlikely host given the restricted host range of genotype 1 viruses. Amazingly, not only were the hamster cells transfected by the Sar55 genomes, the number of transfected cells was boosted almost 7-fold by inclusion of the S17 insert (FIG. 12B, P=<0.0001). The enhancement of transfection by the S17 insert was confirmed by immunofluoresence microscopy in an independent experiment (data not shown).

Figure 13:
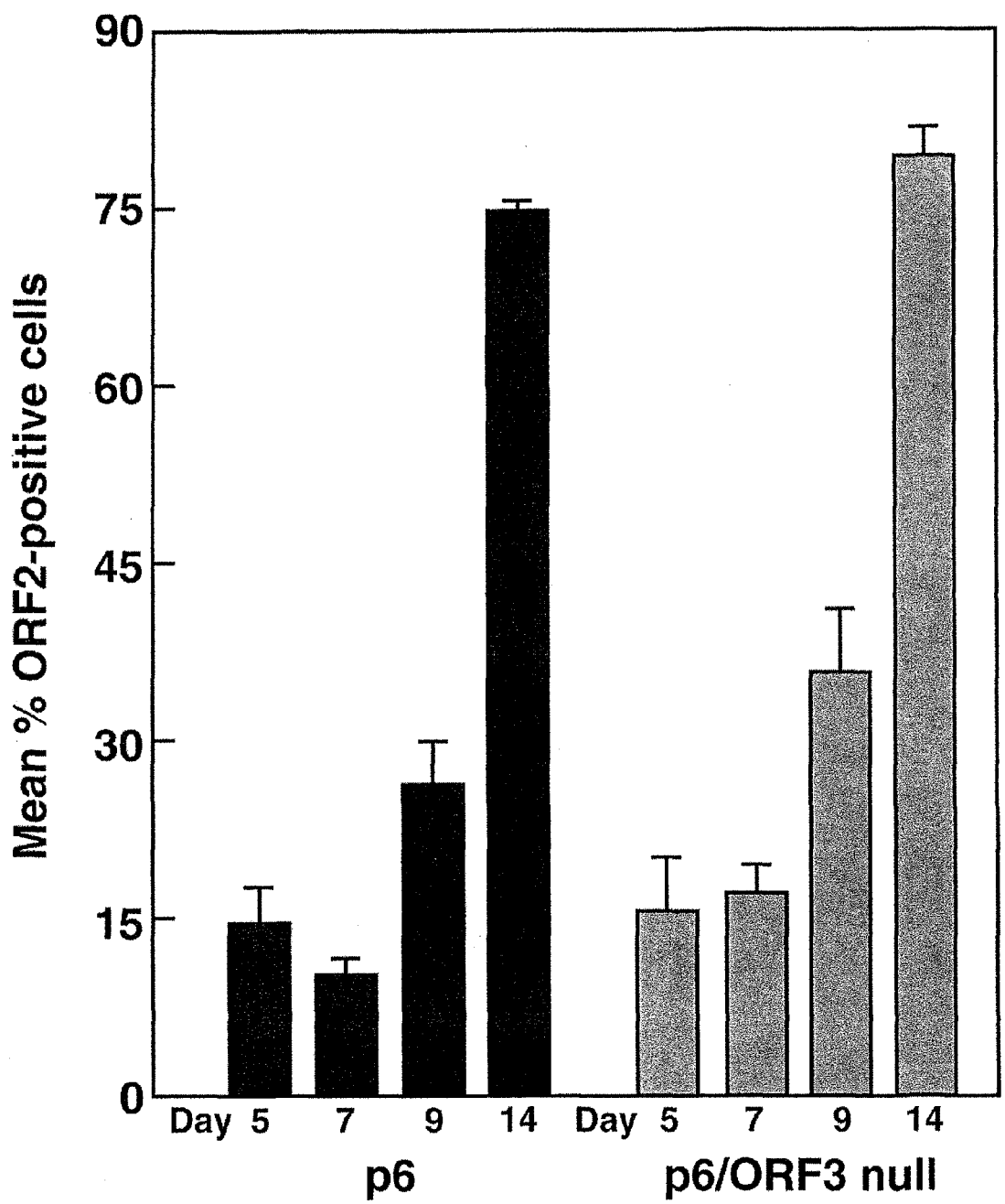
FIG. 13. Lack of ORF3 protein does not inhibit cell-to-cell spread in HepG2/C3A cultures. HepG2/C3A cells were electroporated with transcripts from p6 or p6/ORF3 null plasmids, mixed with naïve HepG2/C3A cells and cultured at 37° C. Triplicate samples were harvested on each of 4 days, fixed with methanol and stored at −80° C. until assayed by flow cytometry. Error bars are standard deviation. P=0.74 for day 5 values of the two viruses indicating that a similar number of cells had been transfected with each construct.

P6 encodes a virus that grows in and spreads among HepG2/C3A cells. Since the p6 cDNA genome was derived from virus adapted to grow in HepG2/C3A cells, the virus encoded by this cDNA clone was predicted to replicate and spread efficiently in cultures of these cells: in contrast, previous studies implicating ORF3 protein in virus egress suggested that a p6 virus genome incapable of producing ORF3 might transfect as many cells as did p6 genomes but that virus would not spread to other cells. P6 virus genomes and p6/ORF3 null genomes were electroporated into HepG2/C3A cells and virus production and spread was monitored by flow cytometry. The p6 virus and the ORF3 null mutant displayed surprisingly similar patterns and both appeared to replicate and spread efficiently throughout the culture: in both cases, the percentage of ORF2 protein-positive cells increased from about 15% on day 5 to over 70% on day 14 (FIG. 13). An independent experiment produced similar results with the percentage of positive cells increasing from 12.4% (+/−1.96) to 59.7% (+/−0.87) for p6 virus and from 13.3% (+/−0.31) to 67.8% (+/−5.57) for the ORF3 null mutant between days 5 to 15. Although these results demonstrated that the p6 clone did indeed encode a cell culture-adapted virus, the similar levels of cell-to-cell spread for the two viruses was puzzling because it had been reported (13, 14) that efficient viral egress required functional ORF3 protein; in those reports, virus release in the absence of ORF3 protein was only about 10% as much as that in its presence. Sequence analysis of the ORF3 region of the null mutant genomes amplified by RT-PCR from the day 9 medium confirmed that no methionine codons were present and ORF3 protein was not detected by immunofluoresence microscopy of the cells (data not shown). However, an infectious focus assay performed with the medium from the two cultures identified an average of 11630 FFU/mL of p6 virus and twice as many, 23200 FFU/mL, of the ORF3 null mutant (data not shown). Determination by real-time RT-PCR of the number of viral genomes in the medium was most revealing: there were indeed ~10-fold fewer viral genomes released into the medium for the ORF3 null mutant compared to the p6 virus. Calculations of the number of viral genomes per FFU indicated that the specific infectivity of the ORF3 null mutant virus was ~20-fold higher than that of p6 virus itself. Therefore, the decrease in egress from cells due to a lack of ORF3 was offset by the increase in infectiousness, thus enabling the null mutant to spread through the culture as efficiently as the parent p6 virus.

Summary

Example 3

An infectious cDNA clone of a hepatitis E virus adapted to grow in HepG2/C3A human hepatoma cells was constructed. This virus was unusual in that the hypervariable region of the adapted virus contained a 171 nucleotide insertion that encoded 58 amino acids of human S17 ribosomal protein. Analyses of virus from 6 serial passages indicated that genomes with this insert were selected during the first passage suggesting it conferred a significant growth advantage. RNA transcripts from this cDNA and the viruses encoded by them were infectious for cells from both human and swine, the major host species for this zoonotic virus. Mutagenesis studies demonstrated that the S17 insert was a major factor in cell culture adaptation. Introduction of 54 synonomous mutations into the insert had no detectable effect thus implicating protein, rather than RNA, as the important component. Truncation of the insert by 50% decreased levels of transfection approximately 3-fold. Substitution of the S17 sequence by a different ribosomal protein sequence or by GTPase activating protein sequence resulted in a partial enhancement of transfection levels, whereas substitution with 58 amino acids of green fluorescent protein had no effect. The S17 sequence did not affect transfection of human hepatoma cells when inserted into the hypervariable region of a genotype 1 strain, but this chimeric genome acquired a dramatic ability to replicate in hamster cells.

Discussion

Examples 1 and 2

The Kernow-C1 strain is the first HEV strain from a chronically-infected patient to be grown in cell culture; among other unique characteristics, it exhibited an exceptionally broad host range. Not only is it the first HEV strain found to infect cells from non-primate species, the range of cross-species infections spanning animals as diverse as chickens and mice was totally unexpected and would not have been predicted based on current knowledge. Note that none of the viruses used have been plaque purified so each inoculum likely represents a mixed population; therefore, the virus infecting primate cells may differ substantially from that infecting cells of other species. The effects of biological diversity and cell culture-acquired mutations should be possible to study once an infectious cDNA clone with robust replication capacity is constructed.

Although the pass 6 virus produced sufficient extracellular virus to permit experiments previously impossible, the low specific infectivity of cell cultured HEV imposes some difficulties. Both genotype 1 (14) and genotype 3 (13) viruses produced in cell culture differed significantly from those excreted in the feces in that they contain ORF3 protein and their virions are not precipitated by anti-ORF2 antibody that readily precipitates fecal virions.

The demonstration that genotype 3 viruses infect swine cells more efficiently than human cells is consistent with the documented ubiquitous infection of swine worldwide compared to the sporadic infection of humans by this genotype (18). The extent and consistency of the opposite tropism of genotype 1 and 3 strains evidenced for human cells versus swine or deer cells in this study (FIG. 2) indicated that the cell culture systems described here are useful for further studying those factors that affect cross-species HEV infections.

The question of how production of ORF2 versus ORF3 protein is regulated is unanswered but the observed bias against Sar-55 ORF2 production in deer cells and its amelioration following introduction of a short 5' RNA sequence from the Kernow-C1 strain (FIG. 3B) suggests that modulation of translation from closely spaced codons can differ significantly according to host species and this may provide one mechanism for restricting host range. Clearly, inhibition of ORF2 capsid protein synthesis would compromise the ability to assemble the virions which could infect additional cells.

Selection of an AUG codon for initiation of translation is directed by position and by the nucleotides adjacent to the codon according to rules defined by Kozak (23). Although genotype 1 and 3 bicistronic mRNAs have the same canonical Kozak sequences, the relevant AUG codons for ORF3 and ORF2 of genotype 3 are three nucleotides closer together than those of genotype 1 and distance between codons is known to affect initiation preferences. Therefore, this difference in AUG spacing (which is conserved within genotypes) probably explains the different translation patterns of genotypes 1 and 3 in deer cells.

In pig cells, differential translation of ORF2 was not observed and Kernow-C1 (genotype 3) and Sar-55 (genotype 1) appeared to have a similar ratio of the two proteins whether in human or pig cells. However, since titer determinations were based on detectable ORF2 production, inefficient genotype-specific translation of ORF2 in one species relative to the other could explain why the titer of Sar-55 was consistently lower on pig cells compared to human cells and the opposite held for Kernow-C1 (FIG. 2)

Receptor differences, either quantitative or qualitative, offer an alternative explanation for host range differences. Specific receptors for HEV have not been identified. In favor of receptor-determined host range, the pass 6 virus maintained a higher titer for pig cells than human cells even though adapted to grow in human cells. There are 54 amino acid differences (8.2%) between Sar-55 and Kernow-C1 capsid proteins and only 5 between the fecal and pass 6 capsid proteins suggesting that the adapted virus may have retained the receptor-interacting specificity of the fecal virus.

ORF3 also is a serious candidate for restricting host range. ORF3 protein is required for virus egress, perhaps through interactions with one or more cellular proteins (13, 14). Since the Sar-55 and Kernow-C1 ORF3 proteins differ by 17.5% (20 of 114 amino acids), Kernow-C1, but not Sar-55 ORF3 may be able to interact efficiently with pig cellular proteins potentially involved in virus exit and, thus, the replication cycle of Sar-55 would be aborted.

Inter- and intra-genomic recombination for HEV has been reported only rarely (24). It is, therefore, quite remarkable that a human RNA sequence was acquired in the pass 6 virus. Since genomes with this insertion were detected in the feces, the insertion is not an artifact of cell culture.

The HVR of Sar-55 could be experimentally truncated but not eliminated, suggesting that the sequence per se was not critical (22). The HVRs compared by Pudupakam et. al. (22) correspond to amino acids 706 to 792 of Kernow-C1 ORF1. The HVR and surrounding region approximately encompassing amino acids 215 to 957 of ORF1 in all strains have no defined functions and they are designated simply as Y and papain-like domains upstream of HVR and as proline hinge and X domain downstream. Therefore, insertions within the HVR would not be expected to disrupt any function. The HVR has not been extensively characterized but one comparison (22) suggests that, within each genotype, certain sequence patterns may be conserved; the HVR sequences of genotypes) and 3 differed substantially in this comparison. The Kernow-C1 fecal consensus sequence contains 86 amino acids compared to 71 for Sar-55. However, the fact that both the Kernow-C1 and the constructed Sar-55 chimera were viable when the S17 insert was present, demonstrated that this region is able to tolerate substantial changes.

Takahashi et al recently showed that virtually any sera with a high HEV titer could infect cultured cells (25). RNA viruses exist as quasispecies and, given the tremendous difficulties in developing a cell culture system for HEV, it appears that a sample with a high titer has an increased probability of containing a variant with the correct constellation of mutations needed to permit infection of a cultured cell. The extraordinary ability of the Kernow-C1 strain to infect cells from such a broad spectrum of species, ranging from rodent to primate, most likely reflects a high titer and a complex quasispecies generated during a prolonged infection in an immunocompromised host: that possibility, along with the demonstration that HEV can acquire new information through recombination with host cell sequences, leads to the conclusion that chronic HEV infection of a patient has important implications for evolution of this "emerging virus". Therefore, it may be desirable to cure HEV infections before they become chronic, not just for the patient's well-being but also for future control of the virus.

Discussion

Example 3

Figure 8:
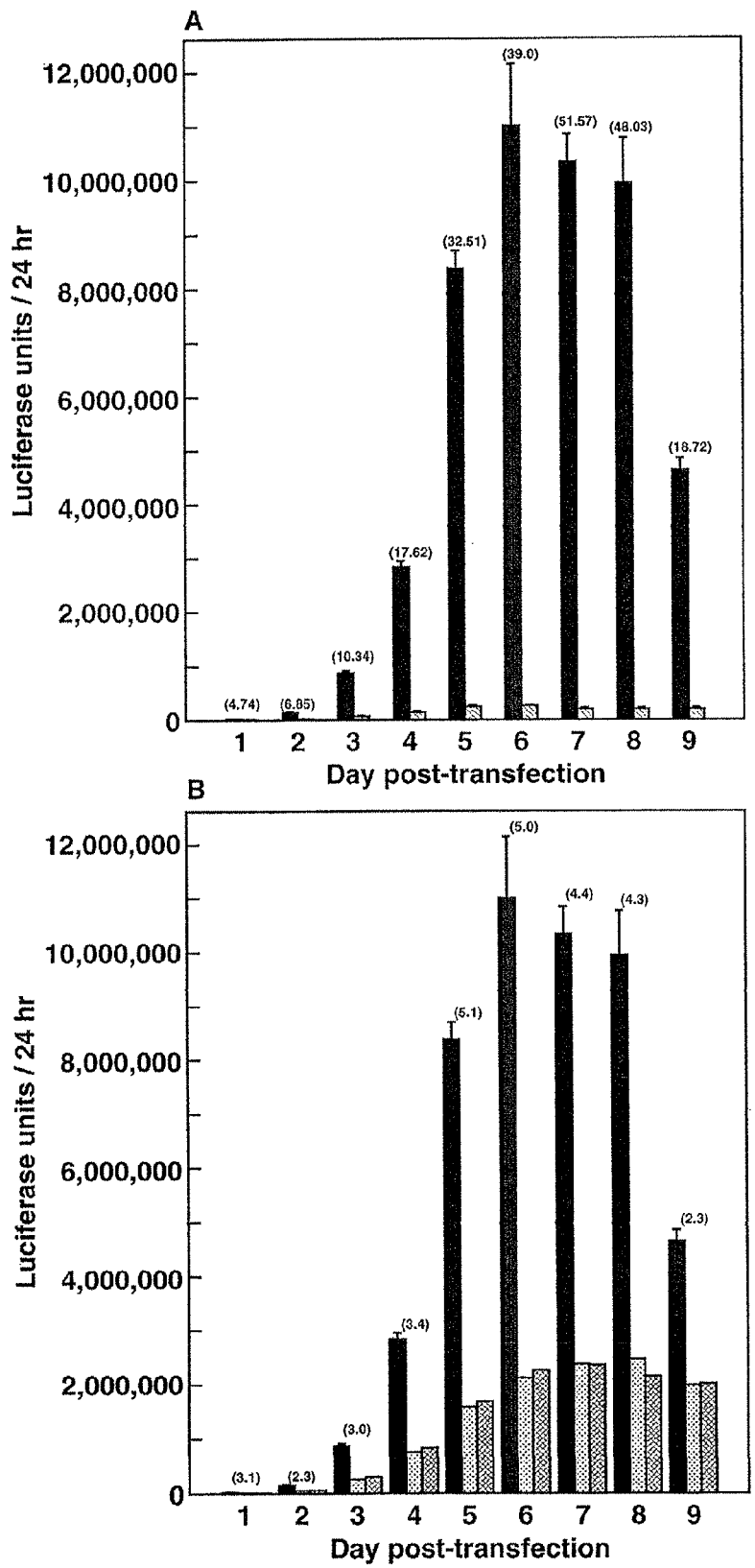
FIG. 8. Expression of luciferase from ORF2 is substantial and prolonged in the presence of the S17 insert. The ORF2 viral capsid protein was replaced with the gaussia luciferase gene in p6 genomes lacking the S17 insert or the X gene region mutations. Following transfection of S10-3 cells, culture medium was completely replaced every 24 hr. Panel A. The ratio of luciferase units produced by genomes with (solid bars) or without (hatched bars) the S17 insert is shown in parentheses above each time point. Error bars are standard deviation. Panel B. The average luciferase production from genomes encoded by two independent cDNA clones lacking the three X gene mutations (stippled bars and cross-hatched bars) was decreased 2.3 to 5.1-fold compared to that from p6/luc genomes (solid bars). Ratios are shown in parentheses above each time point.

With respect to HEV research, the infectious genotype 3 cDNA clone we constructed provides an additional tool. Since the liver is the target organ for this virus, the ability to transfect or infect human liver (HepG2/C3A) cells and to produce large quantities of viable virus may provide a more authentic model system in which to revisit numerous, well-executed studies that produced intriguing data but were limited by their reliance on over-expression of single viral proteins out of context. Additionally, the ability of p6 virus to infect swine cells may prove useful for identifying parameters that restrict the host range of genotype 1 and 2 strains to humans and non-human primates. The luciferase replicon we developed should be especially useful for some studies since it permits convenient sequential sampling and is exquisitely sensitive: since the luciferase gene is located on the subgenomic mRNA, luciferase production can act as an indirect indicator of subgenomic RNA synthesis and stability. This new model system has already provided the first evidence that the previously uncharacterized X gene region has a function in viral replication since three mutations in it contributed substantially to establishment of the infected state following transfection (FIGS. 6 and 8).

Figure 9:
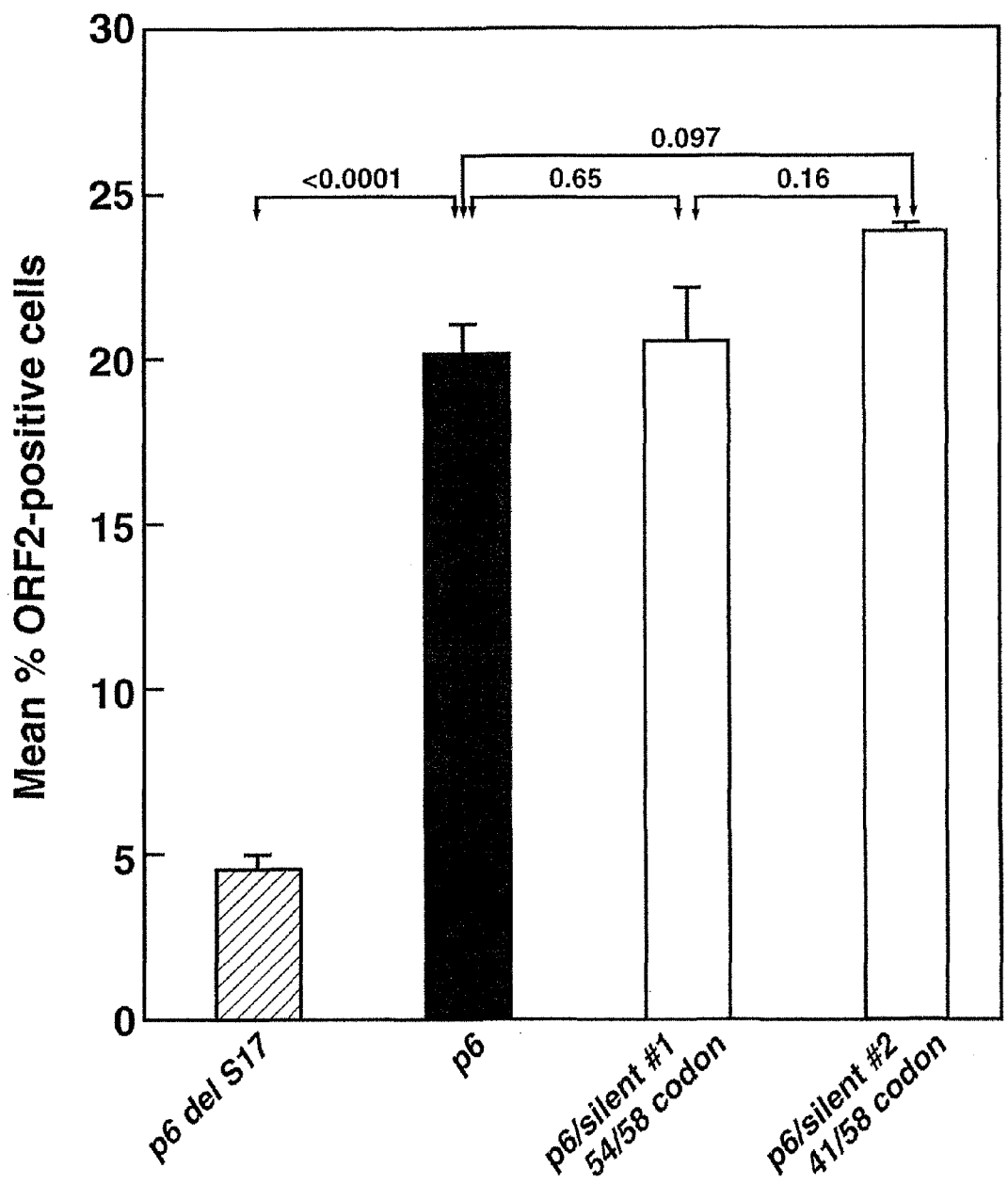
FIG. 9. Synonymous mutations in the S17 insert have little effect on efficiency of transfection. Mutations that preserved the amino sequence were introduced into the third base of 54/58 codons (mutant #1) or 41/58 codons (mutant #2) in the S17 insert and RNA transcripts were transfected into S10-3 cells. Efficiency of transfection was determined by flow cytometry of triplicate samples 5 days posttransfection.
Figure 10:
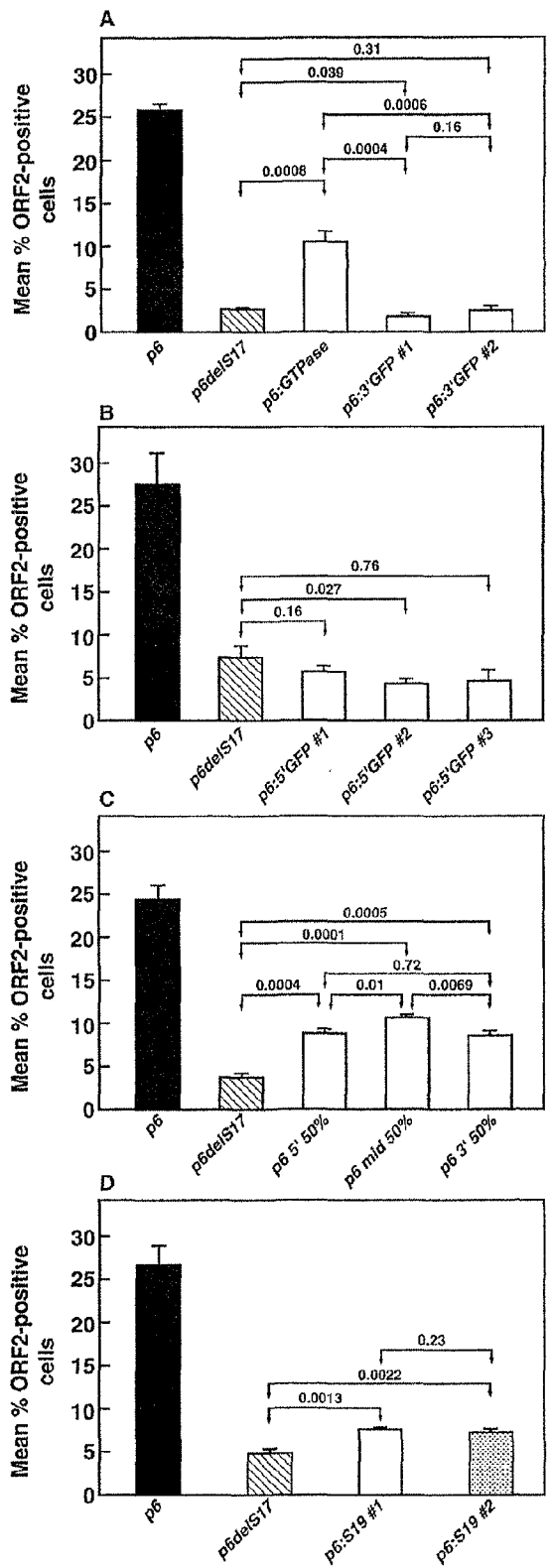
FIG. 10. Comparison of efficiency of transfection by p6 genomic transcripts encoding different HVRs. Triplicate samples were subjected to flow cytometry at day 5 or 6 posttransfection. Error bars represent standard deviation and brackets denote Student's t test P values. The 174 nts encoding the 58 amino acid S17 insert was deleted or replaced with A: the 114 nt GTPase insert from passage 1 or with the 3' terminal 174 nt of green fluorescent protein (GFP). #1 and 2 are two independent clones. P values for p6 versus any other genome=≤0.0003. B: the 5' 174 nt encoding the first 58 amino acids of GFP. #1 to 3=3 independent clones. P values for p6 versus any other genome=<0.001. C: the 5', middle, or 3' 87 nt half of the S17 insert. P values for p6 versus any other genome≤0.0002. D: the 117 nt S19 ribosomal protein gene insert. #1 and 2 are 2 independent clones. P values for p6 versus any other genome<0.001 and P values among the 3 GFP clones=>0.27.

The discovery of the human S17 gene sequence embedded in the HEV genome had been totally unexpected (Example 1); it was especially surprising since it indicated first, that the virus genome had recombined with host RNA and second, that this event had apparently imparted properties that resulted in selection of this extremely minor quasispecies virus in cell culture. This scenario was subsequently repeated with a genotype 3 strain from another chronically-infected patient (Nguyen et al., in press 2012, *J. General Virol.*), suggesting that illegitimate recombination by HEV is not necessarily a rare event. In the present study, we demonstrated that this recombinant virus emerged as soon as the first passage in cell culture (Table 5): its dominance in all passages thereafter strongly suggested that it played a critical role in cell culture adaptation. Mutagenesis studies of the infectious cDNA clone demonstrated unequivocally that the insert was a major factor in enabling efficient virus propagation in cell culture. The stepwise cloning strategy demonstrated that mutations other than the S17 insert also contributed to adaptation (FIG. 5): it was striking, therefore, to find an almost total elimination of enhancement of transfection by point mutations upon removal of the S17 insert from the final construct (FIG. 7). A likely explanation is that that the inserted S17 sequence enhanced the stability/translatability of the RNA or aided the folding/processing/stability of ORF1 protein. The question of proteolytic processing has not yet been resolved for HEV. However, since introduction of synonomous mutations into 24 to 32% of the nucleotide positions in the S17 insert did not appreciably affect the level of transfection (FIG. 9), it seems unlikely that the viral RNA is the important factor, but rather suggests that the effect is at the protein level. Deletion experiments by Pudupakam et al, showed that decreasing the size of the standard HVR could decrease the virulence of HEV or reduce its replication in cell culture. Our data based on the 50% truncations of the S17 insert demonstrated that the size of the insert, and hence of the HVR, matters but the experiments substituting GFP, GTPase or S19 gene fragments (FIG. 10 A, B, D) suggested that the amino acid composition of both the insert and the genomic background contributed to enhancement. This conclusion is in agreement with data showing decreased replication in vitro when the HVR of a genotype 1 and a genotype 3 strain were swapped.

The fact that the S17 sequence increased the ability of Sar55 genomes to replicate in such an unlikely species as hamster cells, leads one to speculate that new syndromes such as neurological disorders recently associated with HEV infections may reflect the ability to infect new cell types because of changes in the HVR. Certainly, this possibility merits exploration.

HEV is not noted for recombination and intergenotypic recombination has been reported only rarely. In retrospect, this might reflect the different transmission pathways and localized geographic distribution of the 4 human genotypes resulting in a low number of co-infections with 2 or more readily distinguishable genomes; intragenotypic recombination might not be noticed unless specifically searched for. However, our discovery of three different human sequences embedded in HEV genomes from the only two patients examined suggests that HEV may undergo recombination more frequently than realized. Additional studies are required to determine whether insertion of these specific ribosomal protein genes occurred by chance or reflected some unknown aspect of HEV replication.

Transfection and infection experiments with human HepG2/C3A and swine LLC-PK1 cells demonstrated that the p6 virus retained the ability of the fecal virus quasispecies to cross species boundaries and displayed a preference for swine cells, although in only one case was the higher titer on swine cells statistically significant. In contrast, the titer of the fecal inoculum was previously reported to be up to 13-fold higher on swine cells compared to human cells, which suggests that there might be other members of the fecal quasispecies that either had mutations favorable for infection of swine cells or detrimental for infection of human cells (FIG. 13). It is not known if receptors or other factors determine host range. Between the p6 cloned virus and the consensus sequence of viruses in the feces, there are four AA differences in the capsid protein which might affect receptor interactions. Two of the four mutations were also present in the p1 virus clone which represented the first selection step for HepG2/C3A cells, so it will be interesting to determine if reversion of any of these mutations to the consensus sequence in the feces will increase the relative titer on swine cells.

Figure 11:
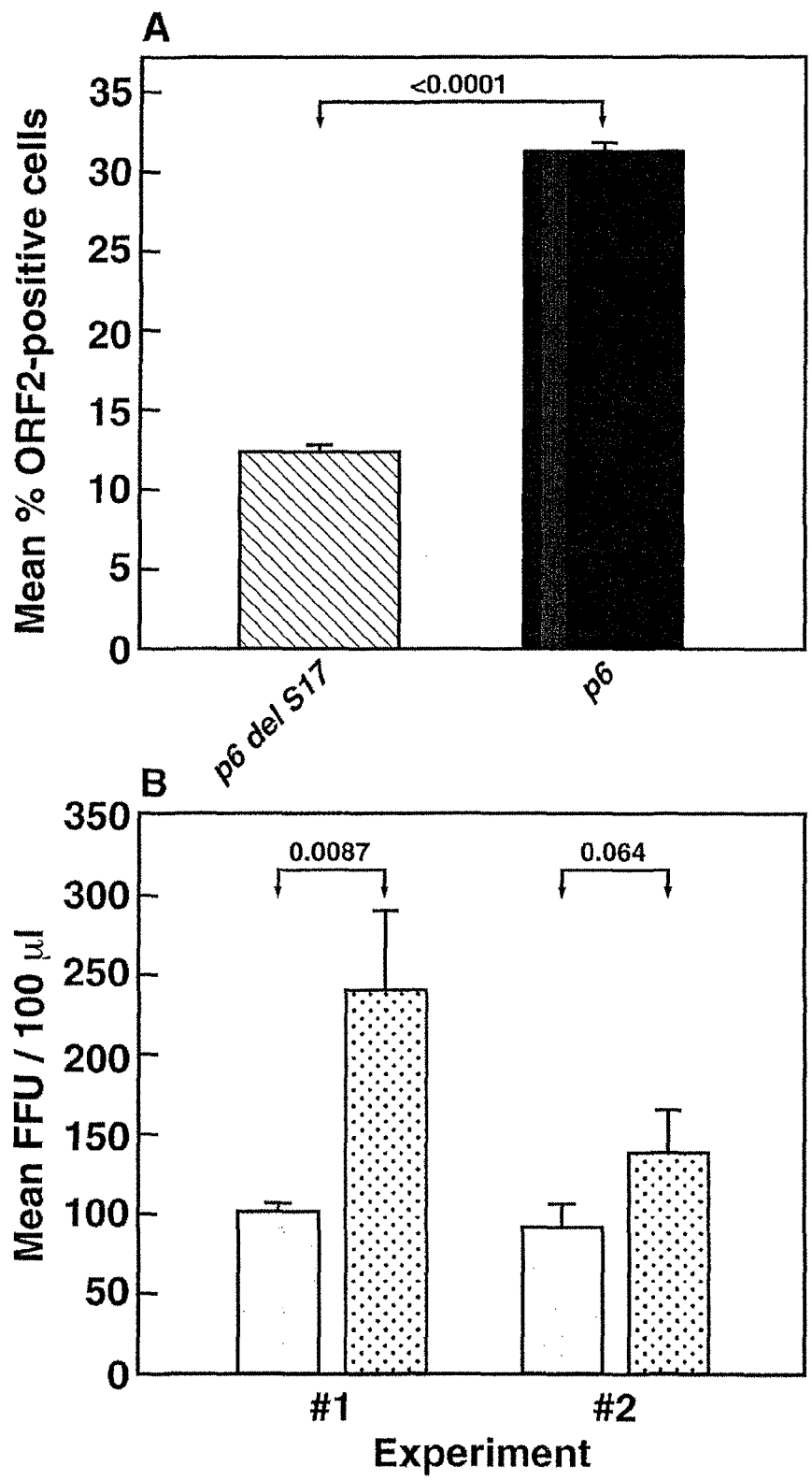
FIG. 11. Genomes or viruses encoded by p6 can replicate in, and infect swine LLC-PK1 cells. A: Swine cells transfected with transcripts from p6 lacking or containing the S17 insert were assayed by flow cytometry at day 5 posttransfection. B: Triplicate samples of p6 virus harvested from the medium of transfected HepG2/C3A cells were titered in parallel on HepG2/C3A cells (open bar) and LLP-CK1 cells (stippled bar) under code.

Although both the p6 virus and ORF3 null virus eventually spread and infected the majority of HepG2/C3A cells in a culture, they did so relatively slowly and the percentage of infected cells did not begin to increase until after day 7 (FIG. 11). In contrast, luciferase expression was detected in the culture medium as soon as day 1 post-transfection (2163 units) and had jumped 38 fold by day 2 (FIG. 8A). Since the luciferase is translated from the subgenomic mRNA, viral negative strand and subgenomic RNA synthesis must have been greatest between days 0 and 2 in this experiment suggesting that synthesis of viral RNA and/or proteins is probably not rate limiting but rather that assembly, maturation and/or excretion are responsible for the relatively slow production of infectious HEV virions. It is worth noting that since the luciferase construct lacks a capsid gene, it cannot spread so the data in FIG. 8C suggested that translation of p6 subgenomic mRNA continued at peak rates through day 7 or 8 before declining.

Perhaps the most confounding result was the discovery that a virus unable to make ORF3 protein spread throughout the culture as efficiently as one synthesizing ORF3 protein. This result poses more questions than answers. The observed difference in specific infectivities provides an explanation of why it happened, but the question of why the specific infectivities differed remains.

MATERIALS AND METHODS

Source Patient

HEV particles were purified from the feces of a 48 year old HIV-1 infected man who was chronically co-infected with HEV for at least 2 years (5). At presentation, the patient had established liver cirrhosis with an active inflammatory component. In addition, he had clinical features of peripheral neuropathy. This was felt to be an HEV-related complication, since HEV was detected in his CSF and symptoms resolved with viral clearance. The virus strain obtained from this patient was designated Kernow-C1 HEV (26).

Cell Culture

Huh-7 human hepatoma cells were originally isolated in Japan (Nakabayashi et al, 1982). Both S10-3 cells, a subclone of Huh-7 cells and C25j cells, a subclone of Caco-2 cells (HTB-37), were isolated in-house. All other cell lines were purchased from the American Type Culture Collection and are described in Supplementary Methods. Most cell lines were propagated in Dulbecco's modified Eagle's medium (cellgro, Mediatech, Manassas, Va.) supplemented with 2 mM L-glutamine, penicillin/streptomycin (Sigma, St. Louis, Mo.) and 10% fetal bovine serum (20% for C25j) (Bio-Whittaker, Walkersville, M D). Deer liver cells and chicken liver cells were cultured in Opti-MEM (Gibco) supplemented with 20% fetal bovine serum (Bio-Whittaker, Walkersville, Md.). The HepG2/C3A, C25j, deer and chicken cells were grown on rat tail collagen type 1 (Millipore). All cell stocks were grown at 37° C. in the presence of 5% $CO_2$.

Virus Stocks

All virus stocks, except pass 6 virus, consisted of 10% fecal suspension in PBS (pH 7.4); RT-PCR titers ranged from $10^6$ to $10^8$ genome equivalents per 100 uL and were not predictive of infectivity titers. Genotype 1 strains Sar-55 (GenBank M80581.1) and Akluj (GenBank AF107909) were isolated from patients in Pakistan and India, respectively. Genotype 3 US-2 strain (GenBank AF060669) was obtained from a patient in the USA and amplified in a rhesus macaque. Genotype 3 Kernow-C1 (ancient Cornish for "Cornwall") strain was obtained from a chronically-infected hepatitis E patient co-infected with HIV as described above. The pass 6 virus is the Kernow-C1 fecal virus that was adapted to grow in HepG2/C3A cells by serial passage.

Plasmid Constructs

The infectious cDNA clone of HEV strain Sar-55, pSK-E2 (GenBank accession no. AF444002) and plasmid CMV-Sar were described previously (16, 27). Plasmid CMV-MT29 was generated by replacing the first 29 nucleotides of Sar-55 subgenomic RNA with that of Kernow-C1 HEV in the plasmid CMV-Sar. Plasmid CMV-Kernow was constructed by amplifying the entire bicistronic mRNA of the Kernow-C1 virus in the feces and cloning it into pCMV5122 as had been done for Sar-55 (16). The Sar-55 cDNA clones containing human S17 gene sequences in sense (Sar55-S17), reverse (Sar55-S17R) and reverse-complement (Sar55-S17RC) orientation were constructed by amplifying the human S17 gene from pass 6 Kernow-C1 virus and inserting it in frame by fusion PCR between nucleotides 2251 and 2252 within the HVR region of pSK-E2. The infectious plasmid pSK-E2-MT29 was generated by replacing the first 29 nucleotides of the Sar-55 bicistronic region in pSK-E2 with that of Kernow-C1.

In Vitro Transcription and Transfection of Cultured Cells

Full-length viral cDNA was transcribed with T7 polymerase and capped transcripts were transfected into S10-3 or deer cells with DMRIE-C (Invitrogen) as described previously (27) and detailed in Supplemental Methods. LLC-PK1 cells were killed by all transfection methods tried. CMV plasmids were transfected into S10-3 and deer cells using Lipofectamine 2000 (Invitrogen) as described in Supplementary Methods.

Infection of Cultured Cells 100,000 cells/well were seeded onto 8 well Lab-Tek™ II-CC²™ slides (Nunc) a day before infection. Virus stocks were diluted in Opti-MEM (Gibco) and 100 µL of the diluted virus was added to each chamber and incubated for 5 h at 34.5° C. in a $CO_2$ incubator. The virus mixture was removed, cells were washed with PBS and medium was added, followed by incubation at 34.5° C. for 3 days.

Immunofluorescence Analysis and Focus Forming Assay

Cells on 8-well chamber slides were fixed with acetone and doubly stained with chimpanzee anti-ORF2 and rabbit anti-ORF3. Stained cells or foci were visualized with a fluorescence microscope and manually counted as described previously (28) and in Supplementary Methods.

Flow Cytometric Analysis for the Quantification of ORF2 and ORF3 Proteins

Transfected cells cultured in 100 mm dishes (Corning) were trypsinized and fixed with 1 mL methanol for 15 min at 4° C. Immunostaining was the same as for adherent cells except separate aliquots of cells were stained for ORF2 and ORF3 proteins. After washing with PBS, cells were resuspended in 1 mL PBS and analyzed using a FACScan flow cytometer (Becton Dickinson). A total of 20,000 events were acquired for each sample and the data were analyzed using BD CellQuest™ software.

RT-PCR

RNA was extracted with Trizol LS (Invitrogen), reverse transcribed, and amplified with a Qiagen kit. PCR products eluted from agarose gels were directly sequenced to provide the fecal and pass 6 consensus sequences or were cloned, then sequenced to provide representative HVR sequences. See Supplemental Methods for details.

Growth Curve

A T25 flask seeded with $10^6$ HepG2/C3A cells was inoculated with 1 mL of previously-titrated fecal or pass 6 virus stock diluted to contain approximately equal FFU for HepG2/C3A cells. An aliquot of each diluted inoculum was frozen at −80° C. for re-titration at the end of the experiment. After 5 hr incubation at 37° C., medium was removed, cells were washed 3 times with Optimem, 2.5 mL of DMEM with 10% fetal bovine serum and antibiotics was added and the flasks were incubated at 37° C. The medium was collected and replaced with fresh medium on the days indicated. The collected medium was passed through a 0.45 µm filter and frozen at −80° C. as 100 uL aliquots. Triplicates of all frozen samples, including the inoculua, were processed in parallel to determine FFU and RNA concentration under identical conditions: direct comparison in the same test indicated the fecal inoculum contained 22,000 FFU compared to 4,200 FFU for the pass 6 virus. The Wilcoxon test was performed on the values from day 7 onward.

Statistics

Statistics were performed by mathematical statisticians in the Biostatistics Research Branch of the National Institute of Allergy and Infectious Diseases. The Student's t-test was used for all but the growth curve analysis.

Supplemental Materials and Methods

Cells. Cell lines purchased from the American Type Culture Collection were human hepatoma HepG2/C3A (CRL-10741) and PLC/PRF/5 (CRL-8024), human lung carcinoma A549 (CCL-185), deer liver OHH1. Li (CRL-6194), swine kidney LLC-PK1 (CL-101), LLC-PK1A (CL-101.1), and SK-RST (CRL-2842), dog kidney MDCK, (CCL-34), cat kidney CRFK (CCL-94), rabbit kidney LLC-RK1 (CCL-106), chicken liver LMH(CRL-2117), and mouse liver Hepa 1-6 (CRL-1830).

In Vitro Transcription and Transfection of Cultured Cells. Plasmid pSK-E2 was linearized at a BglII site located downstream of the poly(A) tail of hepatitis E virus (HEV). Capped RNA transcripts were generated with the T7 Riboprobe in vitro transcription system (Promega) and Anti-Reverse Cap Analog (Ambion) as described previously (Emerson, 2001, supra). For transfection of S10-3 or C25j cells, 40 µL RNA transcription mixture, 1 mL Opti-MEM (Gibco), and 16 µL DMRIE-C (Invitrogen) were mixed and added to one well of a six-well plate. These cell lines were chosen for their high RNA transfection rates: C25j cells produced the highest levels of infectious virus, but they remained intracellular and had to be harvested by cell lysis. For transfection of deer cells, the in vitro-transcribed RNA was purified with the RNeasy kit (Qiagen) following the manufacturer's protocol. The purified RNA (2.5 µg) was diluted in 500 µL Opti-MEM (Gibco), added drop-wise to a mixture containing 500 µL Opti-MEM (Gibco) and 5 µL Lipofectamine 2000 (Invitrogen), incubated at room temperature for 20 min, and added to one well of a six-well plate. After incubation with transfection mixture for 5 h at 34.5° C. in a $CO_2$ incubator, the transfection mixture was replaced with culture medium, and incubation was continued at 34.5° C. LLC-PK1 cells were killed by all transfection methods tried. For plasmid DNA transfection, S10-3 and/or deer cells were grown on six-well plates and transfected with 2 µg DNA using Lipofectamine 2000 (Invitrogen) as described above. The DNA transfection of S10-3 and/or deer cells was performed at 37° C. for 6 h in a $CO_2$ incubator. After the transfection mixture was replaced with culture medium, incubation was continued at 37° C.

Electroporation, HepG2/C3A and LLC-PK1 cells were killed by DMRIE-C, they were thus transfected by electroporation using a BioRad Gene Pulser II at settings of 240 volts and 950 capacitance and a BioRad cuvette #165-2086. RNA transcripts from a 100 ul transcription mixture were extracted with TRIzol LS (Invitrogen), precipitated with isopropanol, washed with 75% ethanol and resuspended in 50 ul water. Cells in a confluent monolayer in a 100 mm dish were detached with trypsin/EDTA, mixed with an equal volume of 1% crystalline bovine serum albumin in PBS and pelleted at 1600 RPM at 40 C for 5 min. Cells were resuspended in 400 uL Optimum, mixed with the RNA, pulsed and added to culture medium containing 20% fetal bovine serum. Cells were placed in plates or flasks and incubated at 370 C (HepG2/C3A) or 34.50 C overnight; HepG2/C3A electroporated cells in a T25 flask were supplemented with one fourth of the untreated cells from a T25 flask in order to provide a dense enough culture to promote growth. The next morning, medium was replaced with fresh medium containing 10% serum and the incubation was continued.

Immunofluorescence Analysis and Focus-Forming Assay. Transfected or infected cells on chamber slides were washed with PBS and fixed and permeabilized with acetone. ORF2 and ORF3 proteins were detected by incubating fixed cells with a mixture of HEV ORF2-specific hyperimmune plasma from an HEV-infected chimpanzee (Ch1313) (Emerson, 2004, supra) and rabbit anti-ORF3 peptide antibody (Emerson, 2004, supra) for 45 min at room temperature. (The chimpanzee plasma was preadsorbed on the respective cell lines to minimize background staining) After washing with PBS, cells were incubated with a mixture of Alexa Fluor 488 goat anti-human IgG (Molecular Probes) and Alexa Fluor 568 goat anti-rabbit IgG (Molecular Probes) for 30 min at room temperature. After washing with PBS, Vectashield mounting medium with DAPI (Vector Laboratories) was added, and cells were visualized at 40× magnification with a Zeiss Axioscope 2 Plus fluorescence microscope. Positive cells or foci were counted manually.

Transfection of S10-3 and Deer Cells with Wild-Type and Mutant cDNA Clones. S10-3 and deer cells were plated on six-well plates 1 d before transfection and were transfected at ~70-80% confluency. Three wells of each plate were transfected with wild-type infectious cDNA of Sar-55 (pSKE2) or with a mutant in which the first 29 nucleotides of the pSK-E2 bicistronic region were replaced with those of Kernow-C1 (pSK-E2-MT29). For FACS analysis of HEV proteins in transfected S10-3 cells, the cells in each well were trypsinized and transferred into separate tubes. The immunostaining of ORF2 and ORF3 proteins and FACS analysis was done as described in Materials and Methods. For immunostaining of deer cells on day 5, cells in each well were trypsinized on day 4, transferred under code to separate wells of eight-well chambered slides, and immunostained on day 5. All ORF2- and ORF3-stained cells were counted manually before the code was broken.

RT-PCR. RNA was extracted with TRIzol LS (Invitrogen). For the consensus sequence of the fecal and passage 6 viruses, RNA was reverse transcribed with SuperScript II RNase H-Reverse Transcriptase (Invitrogen) and usually was amplified with the Qiagen LongRange PCR Kit; a troublesome C-rich region was amplified with the Qiagen LongRange 2Step RT-PCR Kit. Products were electrophoresed on agarose gels, eluted, and directly sequenced. The hypervariable region (HVR) was amplified by nested RT-PCR with the Qiagen LongRange 2 Step RT-PCR Kit. Each pair of the four primer sets for detecting the 174-base insert included one primer matching the HEV sequence and one matching the insert sequence. After electrophoresis, the products were sequenced directly. The nested primer sets for amplifying the entire HVR matched the HEV sequences on either side of the HVR. The visible product and the regions just above and below it were eluted from an agarose gel and cloned with the Zero Blunt TOPO PCR Cloning Kit (Invitrogen), and 120 individual colonies were sequenced. RNA genomes in culture medium were quantified by real-time RT-PCR (TaqMan).

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, accession numbers, patents, and patent applications cited in this specification are herein incorporated by reference as if each was specifically and individually indicated to be incorporated by reference.

ADDITIONAL REFERENCES

1. Kumar A, Beniwal M, Kar P, Sharma J B, Murthy N S (2004) Hepatitis E in pregnancy. *Int J Gynaecol Obstet* 85:240-244.
2. Boccia D, et al. (2006) High mortality associated with an outbreak of hepatitis E among displaced persons in Darfur, Sudan. *Clin Infect Dis* 42:1679-1684.
3. Meng X J (2010) Recent advances in Hepatitis E virus *J Viral Hepat* 17:153-161.
4. Peron J M, et al. (2006) Prolonged hepatitis E in an immunocompromised patient. *J Gastroenterol Hepatol* 21:1223-1224.
5. Dalton H R, Bendall R P, Keane F E, Tedder R S, Ijaz S (2009) Persistent carriage of hepatitis E virus in patients with HIV infection. *N Engl J Med* 361:1025-1027.
6. Legrand-Abravanel F, et al. (2010) Characteristics of autochthonous hepatitis E virus infection in solid-organ transplant recipients in France. *J Infect Dis* 202:835-844.
7. Pischke S, Wedemeyer H (2010) Chronic hepatitis E in liver transplant recipients: a significant clinical problem? *Minerva Gastroenterol Dietol* 56:121-128.
8. Kc S, Sharma D, Basnet B K, Mishra A K (2009) Effect of acute hepatitis E infection in patients with liver cirrhosis. *JNMA J Nepal Med Assoc* 48:226-229.
9. Dalton H R, et al. (2007) The role of hepatitis E virus testing in drug-induced liver injury. *Aliment Pharmacol Ther* 26:1429-1435.
10. Tei S, Kitajima N, Takahashi K, Mishiro S (2003) Zoonotic transmission of hepatitis E virus from deer to human beings. *Lancet* 362:371-373.
11. Purcell R H, Emerson S U (2008) Hepatitis E: An emerging awareness of an old disease. *J Hepatol* 48:494-503.
12. Purcell R H, Emerson S U (2010) Hidden danger: the raw facts about hepatitis E virus. *J Infect Dis* 202:819-821.
13. Yamada K, et al. (2009) ORF3 protein of hepatitis E virus is essential for virion release from infected cells. *J Gen Virol* 90:1880-1891.
14. Emerson S U, et al. (2010) Release of genotype 1 hepatitis E virus from cultured hepatoma and polarized intestinal cells depends on open reading frame 3 protein and requires an intact PXXP motif. *J Virol* 84:9059-9069.
15. Chandra V, Taneja S, Kalia M, Jameel S (2008) Molecular biology and pathogenesis of hepatitis E virus. *J Biosci* 33:451-464.
16. Graff J, Torian U, Nguyen H, Emerson SU (2006) A bicistronic subgenomic mRNA encodes both the ORF2 and ORF3 proteins of hepatitis E virus. *J Virol* 80:5919-5926.
17. Emerson S U, Anderson D, Arankalle A, Meng X J, Prudy M, Schlauder G G and Tsarev S A. (2004) *Hepevirus*. In: *Virus Taxonomy*, VIIIth Report of the ICTV (C. M. Fauquet, M. A. Mayo, J Maniloff, U. Desselberger, and L. A. Ball, eds), 851-855. Elsevier/Academic Press, London.
18. Pavio N, Meng X J, Renou C (2010) Zoonotic hepatitis E: animal reservoirs and emerging risks. *Vet Res* 41:46.

19. Yamada K, et al. (2009) Construction of an infectious cDNA clone of hepatitis E virus strain JE03-1760F that can propagate efficiently in cultured cells. *J Gen Virol* 90:457-462.
20. Tanaka T, et al. (2009) Development and characterization of a genotype 4 hepatitis E virus cell culture system using a HE-JF5/15F strain recovered from a fulminant hepatitis patient. *J Clin Microbiol* 47:1906-1910.
21. Graff J, et al. (2005) In vitro and in vivo mutational analysis of the 3'-terminal regions of hepatitis E virus genomes and replicons. *J Virol* 79:1017-1026.
22. Pudupakam R S, et al. (2009) Deletions of the hypervariable region (HVR) in open reading frame 1 of hepatitis E virus do not abolish virus infectivity: evidence for attenuation of HVR deletion mutants in vivo. *J Virol* 83:384-395.
23. Kozak M (1995) Adherence to the first AUG rule when a second AUG codon follows closely upon the first. *Proc Natl Acad Sci USA* 92:2662-2666.
24. Wang H, et al. (2010) Recombination analysis reveals a double recombination event in hepatitis E virus. *Virol J* 7:129.
25. Takahashi M, et al. (2010) Hepatitis E Virus (HEV) strains in serum samples can replicate efficiently in cultured cells despite the coexistence of HEV antibodies: characterization of HEV virions in blood circulation. *J Clin Microbiol* 48:1112-1125.
26. Dalton H R, et al. (2010) Neurological sequelae of acute and chronic HEV genotype 3 infection. *Gut* 59: suppl II A36.
27. Emerson S U, et al. (2001) Recombinant hepatitis E virus genomes infectious for primates: importance of capping and discovery of a cis-reactive element. *Proc Natl Acad Sci USA* 98:15270-15275.
28. Emerson S U, et al. (2004) In vitro replication of hepatitis E virus (HEV) genomes and of an HEV replicon expressing green fluorescent protein. *J Virol* 78:4838-4846.
29. Nakabayashi H, Taketa K, Miyano K, Yamane T, Sato J (1982) Growth of human hepatoma cell lines with differentiated functions in chemically defined medium. *Cancer Res* 42:3858-3863.

TABLE 1

Production of ORF2 and ORF3 proteins in deer cells transfected with infectious transcripts of wild-type and mutant cDNA clones.

| Experiment number[1] | pSK-E2[2] | | | Experiment number[1] | pSK-E2-MT29[3] | | |
| --- | --- | --- | --- | --- | --- | --- | --- |
| | ORF2[4] | ORF3[4] | ORF3/ORF2 | | ORF2[4] | ORF3[4] | ORF3/ORF2 |
| 1 | 149 | 510 | 3.42 | 4 | 43 | 19 | 0.44 |
| 2 | 146 | 420 | 2.88 | 5 | 56 | 24 | 0.43 |
| 3 | 74 | 351 | 4.74 | 6 | 28 | 9 | 0.32 |

[1]Three cultures were transfected with each viral genome.
[2]The infectious cDNA clone of HEV strain Sar-55.
[3]The infectious cDNA clone of HEV in which the first 29 nucleotides of the Sar-55 bicistronic region in pSK-E2 were replaced with that of Kernow-C1.
[4]Transfected cells were transferred under code to 8-well chamber slides, immunostained on day 5 and all ORF2- and ORF3-positive cells in each well were counted before the code was broken.

TABLE 2

FACS analysis of ORF2 and ORF3 proteins in S10–3 cells after transfection with infectious transcripts of wild-type and mutant cDNA clones.

| Experiment number[1] | pSK-E2[2] | | | Experiment number[1] | pSK-E2-MT29[3] | | |
| --- | --- | --- | --- | --- | --- | --- | --- |
| | ORF2[4] | ORF3[4] | ORF3/ORF2 | | ORF2[4] | ORF3[4] | ORF3/ORF2 |
| 1 | 22.45%[5] | 37.73% | 1.68 | 4 | 21.97% | 29.07% | 1.32 |
| 2 | 23.16% | 38.84% | 1.67 | 5 | 22.21% | 26.96% | 1.21 |
| 3 | 19.78% | 39.70% | 2.00 | 6 | 21.67% | 31.71% | 1.46 |

[5]Three cultures were transfected with each viral genome.
[6]The infectious cDNA clone of HEV strain Sar-55.
[7]The infectious cDNA clone of HEV in which the first 29 nucleotides of the Sar-55 bicistronic region in pSK-E2 were replaced with that of Kernow-C1.
[8]Cells were immunostained for ORF2 and ORF3 proteins on day 5 posttransfection.
[9]Percentage of cells stained for indicated viral proteins.

TABLE 3

Titers of genotype 1 and genotype 3 HEV on HepG2/C3A and LLC-PK1 cells[1].

| | Virus titer in HepG2/C3A cells[2] | | | | | Virus titer in LLC-PK1 cells[2] | | |
| --- | --- | --- | --- | --- | --- | --- | --- | --- |
| Experiment | Sar-55[4] | Akluj | US-2 | Kernow-C1 fecal[5] | Kernow-C1 pass 6 | Sar-55[4] | Akluj | US-2 |
| Exp. 1 | 98,800 | 99,000 | 1,200 | 460,000 | —[6] | 13,000 | 11,400 | 315 |
| | 85,000 | 81,000 | 400 | 560,000 | — | 20,200 | 10,900 | 500 |
| | 78,000 | 80,000 | 560 | 710,000 | — | 12,900 | 11,600 | 560 |
| Exp. 2 | — | — | 250 | 230,000 | — | — | — | 2,100 |
| | — | — | 180 | 240,000 | — | — | — | 1,800 |
| | — | — | 190 | 260,000 | — | — | — | 1,700 |

TABLE 3-continued

Titers of genotype 1 and genotype 3 HEV on HepG2/C3A and LLC-PK1 cells[1].

| Exp. 3[7] | 19,000 | 4,800 | 15 | 4,000 | 1,500 | 64,00 | 530 | 330 |
|---|---|---|---|---|---|---|---|---|
| | 19,000 | 3,800 | 25 | 2,000 | 1,100 | 6,700 | 450 | 390 |
| | 25,000 | 3,700 | 35 | 5,000 | 900 | 5,700 | 490 | 450 |
| Exp. 4 | 69,400 | — | — | — | 6,100 | 24,000 | — | — |
| | 70,000 | — | — | — | 5,400 | 20,000 | — | — |
| | 61,000 | — | — | — | 8,200 | 22,000 | — | — |

| | Virus titer in LLC-PK1 cells[2] | | LLC-PK1/HepG2/C3A[3] | | | | |
|---|---|---|---|---|---|---|---|
| Experiment | Kernow-C1 fecal[5] | Kernow-C1 pass 6 | Sar-55[4] | Akluj | US-2 | Kernow-C1 fecal[5] | Kernow-C1 pass 6 |
| Exp. 1 | 1,120,000 | — | 0.18 | 0.13 | 0.64 | 1.60 | — |
| | 830,000 | — | | | | | |
| | 770,000 | — | | | | | |
| Exp. 2 | 1,040,000 | — | — | — | 9.03 | 4.10 | — |
| | 1,090,000 | — | | | | | |
| | 860,000 | — | | | | | |
| Exp. 3[7] | 40,000 | 6,400 | 0.30 | 0.12 | 15.60 | 13.09 | 5.49 |
| | 53,000 | 5,300 | | | | | |
| | 51,000 | 7,500 | | | | | |
| Exp. 4 | — | 15,000 | 0.31 | — | — | — | 2.84 |
| | — | 19,000 | | | | | |
| | — | 22,000 | | | | | |

TABLE 4

Comparison of consensus sequence of viruses in feces with that passed 6 times in HepG2/C3A cells[1].

| Region of genome | Nucleotide Position[2] | Feces/p6 | Amino acid Position[2] | Feces/p6 |
|---|---|---|---|---|
| Unclassified | 1975 | G/C[3] | 650 | Gly/Ala[3] |
| HVR[4] | 2236 | U/C | 737 | Val/Ala |
| HVR | 2275 | Insert 174 nt | 750 | (Insert 58 aa) |
| HVR | 2329 | A/G | 768 | Asn/Ser |
| HVR | 2334 | A/G | 770 | Ile/Val |
| HVR | 2341 | U/C | 772 | Leu/Ser |
| HVR | 2346 | C/U | 774 | Pro/Ser |
| X Domain | 2562, 2563 | U/C, G/C | 846 | Trp/Ser |
| X Domain | 2899 | A/G | 958 | Asn/Ser |
| Helicase | 3029 | A/U | 1001 | Gln/His |
| Polymerase | 4401 | U/C | 1459 | Phe/Leu |
| Capsid | 5191 | C/U | 2 | Arg/Cys |
| Capsid | 5383 | G/A | 66 | Val/Ile |
| ORF3 | | | 69 | Met/Ile |
| Capsid | 6634 | A/G | 483 | Thr/Ala |
| Capsid | 7142 | U/C | 652 | Met/Ser |
| Capsid | 7144 | A/G | 653 | Lys/Glu |
| 3' NC[5] | 7181 | U/C | — | — |
| 3' NC | 7207 | C/U | — | — |
| 3' NC | 7208 | U/G | — | — |
| 3' NC | 7231 | C/U | — | — |

[1]Not listed: 44 scattered silent mutations with 37/44 U/C or C/U
[2]Position based on sequence of feces virus; insert not numbered
[3]Nucleotide or amino acid in feces virus followed by that in pass 6 virus
[4]Hypervariable region
[5]3' Non-coding region

TABLE 5

Comparison of HVR clones from each passage level. Number of clones

| Passage (No. Clones) | S17[1] | GTPase[2] | Deletion (No. nts)[3] |
|---|---|---|---|
| 1 (11) | 2 | 5 | 1 (171)[4]; 1 (612; 2 (501) |
| 2 (10) | 9 | 0 | 1 (738) |
| 3 (8) | 8 | 0 | 0 |
| 4 (10) | 8 | 0 | 2 (435)[5] |
| 5 (8) | 8 | 0 | 0 |
| 6 (11) | 10 | 0 | 1 (381) |

[1]Number of clones with S17 insert encoding 58 amino acids
[2]Number of clones containing 114 nts of GTPase but lacking S17
[3]Deletion compared to passage 6 but containing S17 insert
[4]Lacking deletions and S17 insert
[5]two identical clones with deletion removing 3' 45 nt of S17

TABLE 6

Stepwise modification of pass 1 Kernow virus by swapping fragments with pass 6 virus

| name | P6 sequence added | mutations added |
|---|---|---|
| p1 | None + pass1 cDNA clone | none |
| p1/S17 | S17 insert | Aa751-807[1] |
| 6812-An | SnaB1-Mlu1 [6812-polyA] | aa593-594[TL/AS][2] 652-653[MK/TE] nt7355-6[tt/cc] 7381[c/t] 7405[c/t] 7407[t/c] [A$_{36}$/A$_{85}$][3] |
| 4608-6812 | Nsi1-SnaB1[4608-6812] | aa483[T/A]; ORF3:aa1[M/T] 69[M/I] |
| 671-2182 | AsiS1-Not1[671-2182] | aa220[A/T] 598[R/C] 650[G/A] |
| 2182-3063 | Not1-BsiW1[2182-3063] | aa838[P/—] 882[L/P] 904[S/P] 965[R/Q] Nt2520-2534 [ccc/cca 4X] |
| 3063-4608 | BsiW1-Nsi1 [3063-4608] | No aa changes |
| p6 | Nsi1-Pml1 [4608-5743] | ORF3:aa1[T/M] |

[1]Parenthesis denotes mutation [pass1/pass6]: upper case = amino acid, lower case = nucleotide
[2]Underlined indicates amino acid mutation in ORF2
[3]Length of poly adenosine tract

TABLE 7

Comparison of consensus sequence of fecal virus to that of passaged viruses[1]

| | | FECAL consensus | p1 CLONE | P6 CLONE | Pass 6 consensus |
|---|---|---|---|---|---|
| ORF1 | yTy 220[2] | A[3] | T | T |
| | sRq 598 | R | C | R |
| | cGa 650 | G | A | A |
| | pVs 737 | V | A | A |
| | vSd 738 | G | S | S |
| | pNp 668 | N | S | S |
| | pIv 770 | I | V | V |
| | vLp 772 | L | S | S |
| | pS/Pp 774[4] | P | S | S |
| | pPp 777 | L | P | P |
| | pPp 779 | S | P | P |
| | pST 785-6 | FK | ST | ST |
| | pPS 789-90 | SA | PS | PS |
| | nPg 824 | L | P | P |
| | yWt 846 | S | P | P |
| | yQv 907 | R | Q | Q |
| | aNl 958 | S | S | S |
| | iQq 1001 | Q | Q | Q/H |
| | vFa1459 | L | L | L |
| ORF2 | mRc 2 | C | C | C |
| | dVv 66 | V | I | I |
| | qTt 483 | T | A | A |
| | pTS 593-4 | TL | AS | TS |
| | kMK 652-3 | MK | TE | TE |
| ORF3 | pMs 69 | M | I | I |
| | vI/Ts 93 | T | T | T |

[1]Numbering according to fecal virus without S17 insert [GenBank HQ389543] . . .
[2]Point mutations are in upper case with the adjacent amino acid in lower case. Numbers indicate the amino acid position of the upper case amino acid.
[3]Letters in each virus column indicate the amino acid present at that position.
[4]Slash indicates a mixture.

TABLE OF SEQUENCES

```
SEQ ID NO: 1 HEV Kernow genotype 3 replicating variant
    1 ggcagaccac gtatgtggtc gatgccatgg aggcccacca gttcattaag gctcctggca
   61 ttactactgc cattgagcag gctgctctgg ctgcggccaa ttccgccttg gcgaatgctg
  121 tggtggttcg gccgttttta tcccgtctac aaaccgagat tcttatcaat ttgatgcaac
  181 cccggcagtt ggttttccgc cctgaagtgc tttggaatca tcctatccag cgggttatac
  241 acaatgaact agaacagtac tgccgggccc gtgctggccg ctgtttggag gtcggagccc
  301 atccgagatc tattaatgat aaccccaacg tcttgcaccg tgtttccttt agaccggttg
  361 gcagggatgt tcagcgctgg tactctgccc ccacccgtgg ccctgcggcc aattgccgcc
  421 gctccgcgct gcgtggcctc cccccgttg accgcaccta ctgttttgat ggattctccc
  481 gttgtgcttt tgctgcagag accggtgtgg ccctttactc tttgcatgac cttggccag
  541 ctgatgttgc agaggcgatg gcccgtcatg ggatgacacg gttgtatgcc gcactacatc
  601 ttccccctga ggtgctgcta ccacccggca cctatcacac aacttcgtat ctcctgattc
  661 acgacggcga tcgcgccgtt gtaacctatg agggcgatac cagtgcgggc tataaccatg
  721 atgtttccat acttcgtgcg tggatccgta ctactaaaat agttggtgac cacccgttgg
  781 ttatagagcg tgtgcgggcc attgttgtc atttcgtgct gttgctcacc gcggcccctg
  841 agccgtcacc tatgccttat gtcccctacc ctcgttcaac ggaggtgtat gttcggtcta
  901 tatttggccc tggcggctct ccatctttgt ttccgtcagc ctgctctact aaatctacct
  961 tccacgctgt cccggtccat atctgggatc ggctcatgct ctttggtgcc accctggatg
 1021 atcaggcgtt ctgttgttca cgactcatga cttacctccg tggtattagc tacaaggtca
 1081 ctgttggtgc gcttgttgct aatgaggggt ggaacgcctc tgaagatgct cttactgcag
 1141 tgatcactgc ggcttatctg actatctgcc atcagcgcta cctccgtacc caggcgatat
 1201 ccaagggcat gcgccggttg gaggttgagc atgcccagaa atttatcaca agactctaca
 1261 gttggctatt tgagaagtct ggccgtgatt acatccccgg ccgccagctc cagtttatg
 1321 cacagtgccg acgtggcta tctgcaggat tccatctgga ccccaggtg cttgttttg
 1381 atgaatcagt gccatgtcgt tgtaggacgt tcctgaagaa agtcgcgggt aaattctgct
 1441 gttttatgcg gtggttaggg caggagtgca cctgcttcct ggagccagcc gagggtttag
 1501 ttggcgacca tggccatgac aatgaggctt atgaaggttc tgaggtcgac caggctgaac
 1561 ctgcccatct tgatgtttcg gggacttatg ccgtccacgg gcaccagctt gtagccctct
```

TABLE OF SEQUENCES-continued

```
1621 atagggcact taatgtccca catgatattg ccgctcgagc ttcccgatta acggctactg 1681 ttgagcttgt tgcaggtcca gaccgcttgg agtgccgcac tgtgctcggt aataagacct 1741 tccggacgac ggtggttgat ggcgcccatc ttgaagcgaa tggcccagag cagtatgtcc 1801 tgtcatttga cgcctcccgt cagtctatgg gggccgggtc gcacaacctc acttatgagc 1861 tcacccctgc cggtttgcag gttaggatct catctaacgg tctggattgc actgctacat 1921 tcccccccgg cggtgcccct agcgccgcgc caggggaggt ggcagccttc tgtgctgccc 1981 tttacagata taacaggttc acccagcggc actcgctgac cggtggacta tggttacacc 2041 ctgagggatt gctgggtatc ttccctccat tctcccctgg gcatatctgg gagtctgcta 2101 accccttttg cggggagggg actttgtata cccggacctg gtcaacatct ggcttttcta 2161 gtgatttctc tcccctgag gcggccgccc ctgcttcggc tgctgcccg gggctgcccc 2221 accctacccc gcctgctagt gatatttggg cgttaccacc gccctccgag gagtgctaca 2281 cgcgcctggg caacgacttc cacacgaaca agcgcgtgtg cgaggagatc gccattatcc 2341 ctagcaaaaa gccccgcaac aagatggcag gttatgtcac gcatctgatg aagcgaattc 2401 agagaggccc agtaagaggt atctccatca agctgcagga ggaggctcag gtcgatgcag 2461 catctgtgcc ccttaccctc gtgcctgctg ggtcgcccag ccctgttgtg tcaccttccc 2521 cccccccccc tcccccgtg cgtaagccat caacaccccc gccttctcgt acccgtcgcc 2581 tcctctacac ctaccccgac ggcgctaagg tgtatgcagg gtcattgttt gaatcagact 2641 gtgattggct ggttaacgcc tcaaacccgg gccatcgccc tggaggtggc ctctgtcatg 2701 cctttcatca acgttttccg gaggcgtttt atccgactga attcattatg cgtgagggcc 2761 tagcggcata caccctgacc ccgcgcccta tcatccacgc agtggcgccc gactacaggg 2821 ttgagcagaa cccgaagagg ctcgaggcag cgtaccggga aacttgctcc cgtcgtggca 2881 ccgctgctta cccgctttta ggctcgggca tataccaggt ccctgtcagc ctcagttttg 2941 atgcctggga acgcaatcat cgccccggcg atgagcttta cttgactgag cccgctgcgg 3001 cttggtttga ggctaataag ccggcgcagc cggcgcttac cataactgag gatacggctc 3061 gtacggccag cctggcatta gagatcgacg ccgctacaga ggttggccgt gcttgtgccg 3121 gctgcactat cagtcctggg attgtgcact atcagtttac cgctggggtc ccgggctcgg 3181 gcaagtcaag gtccatacaw cagggagatg ttgatgtggt ggttgtgccc acccgggagc 3241 tccgtaacag ttggcgccgc cggggtttcg cggctttcac acctcacaca gcggcccgtg 3301 ttactaacgg ccgccgcgtt gtgattgatg aggccccatc tctcccgcca cacctgttgc 3361 tgctacatat gcagcgggcc tcctcggtcc acctactcgg tgacccaaat cagatccctg 3421 ctatcgattt tgaacacgcc ggcctggtcc ccgcgatccg ccccgagctt gcaccaacga 3481 gctggtggca cgtcacacac cgttgcccgg ccgatgtgtg cgaactcata cgcggggcct 3541 accccaaaat ccagaccacg agccgtgtgc tacggtccct gttttggaat gaaccggcta 3601 tcggccagaa gttggttttty acgcaggctg ccaaggccgc taaccctggt gcgattacgg 3661 ttcacgaagc tcagggtgcc accttcactg agaccacagt tatagccacg gccgacgcca 3721 gggcctcat tcagtcatcc cgggcccatg ctatagttgc acttacccgc cacaccgaga 3781 agtgcgtcat tttggatgct cccggcctgc tgcgtgaagt sggtatctcg gatgtgattg 3841 tcaataattt tttccttgca ggcggagagg tcggccatca ccgcccttct gtgatacccc 3901 gcggtaaccc cgatcagaac ctcgggactt tacaagcctt cccgccgtcc tgccagatta 3961 gtgcttacca ccagctggct gaggaattag gccatcgccc tgccctgtt gccgccgtct
```

TABLE OF SEQUENCES-continued

```
4021 tgcccccttg ccccgagctt gagcagggcc tgctttacat gccacaagag cttaccgtgt
4081 ctgatagtgt gctggttttt gagcttacgg acatagtcca ctgccgcatg gccgctccaa
4141 gccagcgaaa ggctgttctt tcaacacttg tggggcggta tggccgtagg acgaagttat
4201 atgaggcagc acattcagat gtccgtgagt ccctagccag gttcatcccc actatcgggc
4261 ccgttcaggc caccacatgt gagttgtatg agttggttga ggccatggtg gagaagggtc
4321 aggacgggtc agccgtctta gagctagatc tctgcaatcg tgatgtctcg cgcatcacat
4381 ttttccaaaa ggattgcaac aagtttacaa ctggtgagac tattgcccat ggcaaggttg
4441 gtcagggtat atcggcctgg agcaagacct tctgcgcttt gtttggcccg tggttccgtg
4501 ccattgagaa agaaatactg gccctgctcc cgcctaatgt cttttatggc gatgcttatg
4561 aggagtcagt gcttgctgcc gctgtgtcag gggcggggtc atgcatggta tttgaaaatg
4621 acttttcgga gtttgatagc acccagaaca acttctctct cggccttgag tgtgtggtta
4681 tggaggagtg cggcatgcct caatggttaa ttaggttgta tcacctggta cggtcagcct
4741 ggattctgca ggcgccaaag gagtctctta agggtttctg gaagaagcat tctggtgagc
4801 ccggtaccct tctttggaac accgtttgga acatggcaat catagcacat tgctacgagt
4861 tccgtgactt tcgtgttgct gcctttaagg gtgatgattc ggtggtcctc tgtagcgact
4921 accggcagag ccgcaatgcg gcagctttga ttgctggctg tgggcttaaa ttgaaggttg
4981 actatcgccc cattgggctg tatgctgggg tggtggtggc ccctggcttg gggacactgc
5041 ctgatgtggt gcgttttgct ggtcggctgt ctgaaaagaa ttggggcccc ggcccggaac
5101 gtgctgagca gctacgtctt gctgtttgtg atttccttcg agggttgacg aacgttgcgc
5161 aggtctgtgt tgatgttgtg tcccgtgtct atggagttag ccccgggctg gtacataacc
5221 ttattggcat gttgcagacc attgccgatg gcaaggccca ctttacagag actattaaac
5281 ctgttcttga tcttacaaat tccatcatac agcgggtaga atgaataaca tgtttgttgc
5341 atcgcccatg ggatcaccat gtgccctagg gttgttctgc tgctgttctt cgtgtttctg
5401 cctatgctgc ccgcgccacc ggccggccag ccgtctggcc gtcgtcgtgg gcggcgcagc
5461 ggcggtgccg gcggtggttt ctggggtgac agggttgatt ctcagcccct cgccctcccc
5521 tatattcatc caaccaaccc cttcgccgcc gatatcgttt cacaatccgg ggctggaact
5581 cgccctcggc agccgccccg cccccttggc tccgcttggc gtgaccagtc ccagcgcccc
5641 tccgctgccc ccgccgtcg atctgcccca gctggggctg cgccgttgac tgctgtatca
5701 ccagcccctg acacagcccc tgtacctgat gttgattcac gtggtgctat tctgcgtcgg
5761 cagtataatt tgtccacgtc cccgctcacg tcatctgttg cttcgggtac caatttggtt
5821 ctctacgctg ccccgctaaa tcccctcttg cccctccagg atggcaccaa cacccatatc
5881 atggctactg aggcatccaa ctatgctcag taccgggtcg ttcgagctac gatccgctac
5941 cgcccgctgg tgccgaatgc tgttggtggt tatgctattt ctatttcttt ttggcctcaa
6001 actacaacta cccctacttc tgttgatatg aattctatta cttccactga tgttaggatt
6061 ttggtccagc ccgtattgc ctccgagtta gtcatcccta gtgagcgcct tcattatcgc
6121 aatcaaggct ggcgctctgt tgagaccaca ggtgtggctg aggaggaggc tacctccggt
6181 ctggtaatgc tttgcattca tggctctcct gttaactctt atactaatac accttacact
6241 ggtgcgttgg ggctccttga ttttgcacta gagcttgaat tcaggaattt gacacccggg
6301 aacaccaaca cccgtgtttc ccggtatacc agcacagccc gtcatcggtt gcgccgcggt
6361 gctgatggga ccgctgagct tactaccaca gcagccacac gatttatgaa ggatctgcat
```

TABLE OF SEQUENCES-continued

```
6421 ttcactggca ctaatggcgt tggtgaggtg ggtcgcggta tcgccctgac actgttcaat
6481 cttgctgata cgcttctagg tggtttaccg acagaattga tttcgtcggc tgggggtcag
6541 ttgttctact cccgcccctgt tgtctcggcc aatggcgagc cgacagtgaa gttatacaca
6601 tctgtggaga atgcgcagca agacaagggc attaccatcc cacacgatat agatttgggt
6661 gactcccgtg tggttattca ggattatgat aatcagcacg agcaagaccg acccacgccg
6721 tcacctgccc cctcacgccc tttctcagtc cttcgcgcta acgatgtttt gtggctctcc
6781 ctcactgccg ctgagtacga tcaggctacg tatgggtcgt ctaccaaccc tatgtatgtc
6841 tctgatacag ttacctttgt caatgtgcc actggtgctc aggctgttgc ccgctctctt
6901 gattggtcta aagttacttt ggatggtcgc ccccttacta ccattcagca gtattctaag
6961 acattttatg ttctcccgct ccgcgggaag ctgtccttt gggaggctgg cacaactagg
7021 gccggctacc catataacta taacaccact gctagtgatc aaattctgat tgagaatgcg
7081 gccgccatc gtgtcgctat ctccacctac actaccagcc tgggtgccgg ccctacctcg
7141 atctccgcgg tgggtgtatt agccccacac tcggcccttg ctgttcttga ggacactgtt
7201 gattaccctc tcgtgctca cacttttgat gatttctgcc cggagtgtcg taccctaggt
7261 ttgcagggtt gtgcattcca gtccactatt gctgagcttc agcgccttaa aacggaggta
7321 ggcaaaaccc gggagtctta attaattcct tccgtgcccc cttcgcagtc ttccttttgg
7381 ctttatttct tatttctgct ttccgcgctc cctggaaaaa aaaaaaaaa
```

SEQ ID NO: 2 "ORF1" amino acid sequence; the underlined region is an insertion in the hyervariable region
    /codon_start=1
    /product="non-structural protein"
    /protein_id="ADV71352.1"
    /db_xref="GI:319748766"

MEAHQFIKAPGITTAIEQAALAAANSALANAVVRPFLSRLQTE

ILINLMQPRQLVFRPEVLWNHPIQRVIHNELEQYCRARAGRCLEVGAHPRSINDNPNV

LHRCFLRPVGRDVQRWYSAPTRGPAANCRRSALRGLPPVDRTYCFDGFSRCAFAAETG

VALYSLHDLWPADVAEAMARHGMTRLYAALHLPPEVLLPPGTYHTTSYLLIHDGDRAV

VTYEGDTSAGYNHDVSILRAWIRTTKIVGDHPLVIERVRAIGCHFVLLLTAAPEPSPM

PYVPYPRSTEVYVRSIFGPGGSPSLFPSACSTKSTFHAVPVHIWDRLMLFGATLDDQA

FCCSRLMTYLRGISYKVTVGALVANEGWNASEDALTAVITAAYLTICHQRYLRTQAIS

KGMRRLEVEHAQKFITRLYSWLFEKSGRDYIPGRQLQFYAQCRRWLSAGFHLDPRVLV

FDESVPCRCRTFLKKVAGKFCCFMRWLGQECTCFLEPAEGLVGDHGHDNEAYEGSEVD

QAEPAHLDVSGTYAVHGHQLVALYRALNVPHDIAARASRLTATVELVAGPDRLECRTV

LGNKTFRTTVVDGAHLEANGPEQYVLSFDASRQSMGAGSHNLTYELTPAGLQVRISSN

GLDCTATFPPGGAPSAAPGEVAAFCAALYRYNRFTQRHSLTGGLWLHPEGLLGIFPPF

SPGHIWESANPFCGEGTLYTRTWSTSGFSSDFSPPEAAAPASAAAPGLPHPTPPASDI

WALPPPSEE<u>CYTRLGNDFHTNKRVCEEIAIIPSKKPRNKMAGYVTHLMKRIQRGPVRG

ISIKLQEEA</u>QVDAASVPLTLVPAGSPSPVVSPSPPPPPVRKPSTPPPSRTRRLLYTY

PDGAKVYAGSLFESDCDWLVNASNPGHRPGGGLCHAFHQRFPEAFYPTEFIMREGLAA

YTLTPRPIIHAVAPDYRVEQNPKRLEAAYRETCSRRGTAAYPLLGSGIYQVPVSLSFD

AWERNHRPGDELYLTEPAAAWFEANKPAQPALTITEDTARTASLALEIDAATEVGRAC

AGCTISPGIVHYQFTAGVPGSGKSRSIXQGDVDVVVVPTRELRNSWRRRGFAAFTPHT

AARVTNGRRVVIDEAPSLPPHLLLLHMQRASSVHLLGDPNQIPAIDFEHAGLVPAIRP

TABLE OF SEQUENCES-continued

```
ELAPTSWWHVTHRCPADVCELIRGAYPKIQTTSRVLRSLFWNEPAIGQKLVFTQAAKA

ANPGAITVHEAQGATFTETTVIATADARGLIQSSRAHAIVALTRHTEKCVILDAPGLL

REVGISDVIVNNFFLAGGEVGHHRPSVIPRGNPDQNLGTLQAFPPSCQISAYHQLAEE

LGHRPAPVAAVLPPCPELEQGLLYMPQELTVSDSVLVFELTDIVHCRMAAPSQRKAVL

STLVGRYGRRTKLYEAAHSDVRESLARFIPTIGPVQATTCELYELVEAMVEKGQDGSA

VLELDLCNRDVSRITFFQKDCNKFTTGETIAHGKVGQGISAWSKTFCALFGPWFRAIE

KEILALLPPNVFYGDAYEESVLAAAVSGAGSCMVFENDFSEFDSTQNNFSLGLECVVM

EECGMPQWLIRLYHLVRSAWILQAPKESLKGFWKKHSGEPGTLLWNTVWNMAIIAHCY

EFRDFRVAAFKGDDSVVLCSDYRQSRNAAALIAGCGLKLKVDYRPIGLYAGVVVAPGL

GTLPDVVRFAGRLSEKNWGPGPERAEQLRLAVCDFLRGLTNVAQVCVDVVSRVYGVSP

GLVHNLIGMLQTIADGKAHFTETIKPVLDLTNSIIQRVE

SEQ ID NO: 3 ORF3 CDS: 5348 . . . 5689
    /codon_start=1
    /product="viral protein"
    /protein_id="AD71353.1"
    /db_xref="GI:319748767"
MGSPCALGLFCCCSSCFCLCCPRHRPASRLAVVVGGAAAVPAVV

SGVTGLILSPSPSPIFIQPTPSPPISFHNPGLELALGSRPAPLAPLGVTSPSAPPLPP

AVDLPQLGLRR

SEQ ID NO: 4 ORF2 CDS: 5359 . . . 7341
    /codon_start=1
    /product="capsid protein"
    /protein_id="ADV71354.1"
    /db_xref="GI:319748768"
MCPRVVLLLFFVFLPMLPAPPAGQPSGRRRGRRSGGAGGGFWGD

RVDSQPFALPYIHPTNPFAADIVSQSGAGTRPRQPPRPLGSAWRDQSQRPSAAPRRRS

APAGAAPLTAVSPAPDTAPVPDVDSRGAILRRQYNLSTSPLTSSVASGTNLVLYAAPL

NPLLPLQDGTNTHIMATEASNYAQYRVVRATIRYRPLVPNAVGGYAISISFWPQTTTT

PTSVDMNSITSTDVRILVQPGIASELVIPSERLHYRNQGWRSVETTGVAEEEATSGLV

MLCIHGSPVNSYTNTPYTGALGLLDFALELEFRNLTPGNTNTRVSRYTSTARHRLRRG

ADGTAELTTTAATRFMKDLHFTGTNGVGEVGRGIALTLFNLADTLLGGLPTELISSAG

GQLFYSRPVVSANGEPTVKLYTSVENAQQDKGITIPHDIDLGDSRVVIQDYDNQHEQD

RPTPSPAPSRPFSVLRANDVLWLSLTAAEYDQATYGSSTNPMYVSDTVTFVNVATGAQ

AVARSLDWSKVTLDGRPLTTIQQYSKTFYVLPLRGKLSFWEAGTTRAGYPYNYNTTAS

DQILIENAAGHRVAISTYTTSLGAGPTSISAVGVLAPHSALAVLEDTVDYPARAHTFD

DFCPECRTLGLQGCAFQSTIAELQRLKTEVGKTRES

SEQ ID NO: 5 Kernow C1 HEV nucleic acid sequence
    1 ggcagaccac gtatgtggtc gatgccatgg aggcccacca gttcattaag gctcctggca
   61 ttactactgc cattgagcag ctgctctgg ctgcggccaa ttccgccttg gcgaatgctg
  121 tggtggttcg gccgttttta tcccgtctac aaacygagat tcttatcaat ttgatgcaac
  181 cccggcagtt ggttttccgc cctgaagtgc tttggaatca tcctatccag cgggttatac
  241 acaatgaact agaacagtac tgccgggccc gtgctggccg ctgtttggag gtcggagccc
  301 atccgagatc tattaatgat aaccccaacg tcttgcaccg gtgcttcctt agaccggttg
  361 gcagggatgt tcagcgctgg tactctgccc ccaccgtgg ccctgcggcc aattgccgcc
  421 gctccgcgct gcgtggcctc cccccgttg accgcaccta ctgttttgat ggattctccc
```

TABLE OF SEQUENCES-continued

```
 481 gttgtgcttt tgctgcagag accggtgtgg cccttactc tttgcatgac ctttggccag
 541 ctgatgttgc agaggcgatg gcccgtcatg ggatgacacg gttgtatgcc gcactacatc
 601 ttcctcctga ggtgctgcta ccacccggca cctatcacac aacttcgtat ctcctgattc
 661 acgacggcga tcgcgccgtt gtaacctatg agggcgatac cagtgcgggc tataaccatg
 721 atgtttccat acttcgtgcg tggatccgta ctactaaaat agttggtgac cacccgttgg
 781 ttatagagcg tgtgcgggcc attggttgtc atttcgtgct gttgctcacc gcggccctg
 841 agccgtcacc tatgccttat gtcccctacc ctcgttcaac ggaggtgtat gttcggtcta
 901 tatttggccc tggcggctct ccatccttgt ttccgtcagc ctgctctact aaatctacct
 961 tccatgctgt cccggtccat atctgggatc ggctcatgct ctttggtgcc accctggatg
1021 atcaggcgtt ctgttgttca cgactcatga cttacctccg tggtattagc tacaaggtca
1081 ctgttggtgc gcttgttgct aatgaggggt ggaacgcctc tgaagatgct cttactgcag
1141 tgatcactgc ggcttatctg actatctgcc atcagcgcta cctccgtacc caggcgatat
1201 ccaagggcat gcgccggttg gaggttgagc atgcccagaa atttatcaca agactctaca
1261 gttggctatt tgagaagtct ggccgtgatt acatccccgg ccgccagctc cagttttatg
1321 cacagtgccg acggtggcta tctgcaggat tccatctgga ccccagggtg cttgtttttg
1381 atgaatcagt gccatgtcgt tgtaggacgt tcttgaagaa agtcgcgggt aaattctgct
1441 gttttatgcg gtggttaggg caggagtgca cctgcttctt ggagccagcc gagggtttag
1501 ttggcgacca tggccatgac aatgaggctt atgaaggttc tgaggtcgac caggctgaac
1561 ctgcccatct tgatgtttcg gggacttatg ccgtccacgg gcaccagctt gtagccctct
1621 atagggcact taatgtccca catgatattg ccgctcgagc ttcccgacta acggctactg
1681 ttgagcttgt tgcaggtcca gaccgcttgg agtgccgcac tgtgctcggt aataagacct
1741 tccggacgac ggtggttgat ggcgcccatc ttgaagcgaa tggcccagag cagtatgtcc
1801 tgtcatttga cgcctcccgt cagtctatgg gggccgggtc gcacaacctc acttatgagc
1861 tcaccccctgc cggtttgcag gttaggatct catctaacgg tctggattgc actgctacat
1921 tccccccccgg cggtgcccct agcgccgcgc caggggaggg ggcagccttc tgtggtgccc
1981 tttatagata taacaggttc acccagcggc actcgctgac cggtggacta tggttacacc
2041 ctgagggatt gctgggcatc ttccctccat tctcccctgg gcatatctgg gagtctgcta
2101 accccttttg cggggagggg actttgtata cccggacctg gtcaacatct ggcttttcta
2161 gtgatttctc tccccctgag gcggccgccc ctgcttcggc tgctgccccg gggctgcccc
2221 atcctacccc gcctgttagt gatatttggg cgttaccacc gccctcagag gagtctcagg
2281 tcgatgcagc atctgtgccc cttaccctcg tgcctgctgg gtcgcccaac cctattgtgt
2341 tacctycccc ccccccccct cccccgtgc gtaagccatc aacaccccg ccttctcgta
2401 cccgtcgcct cctctacacc tatcccgacg gcgctaaggt gtatgcaggg tcattgtttg
2461 aatcagactg tgattggctg gttaacgcct caaacccggg ccatcgccct ggaggtggcc
2521 tctgtcatgc ctttcatcaa cgtttttccag aggcgtttta ttggactgaa ttcattatgc
2581 gtgagggcct agcggcatac accctgaccc cgcgccctat catccacgca gtggcgcccg
2641 actacagggt tgagcagaac ccgaagaggc tcgaggcagc gtaccgggaa acttgctccc
2701 gtcgtggcac cgctgcttac ccgcttttag gctcgggcat ataccaggtc cctgtcagcc
2761 tcagttttga tgcctgggaa cgcaatcatc gcccggcga tgagctttac ttgactgagc
2821 ccgctgcggc ttggtttgag gctaataagc cggcgcagcc ggcgcttacc ataactgagg
```

TABLE OF SEQUENCES-continued

```
2881 acacggctcg tacggccaac ctggcactag agatcgacgc cgctacagag gttggccgtg
2941 cttgtgccgg ctgcactatc agtcctggga ttgtgcacta tcagtttacc gctgggggtcc
3001 cgggctcggg caagtcaagg tccatacaac agggagatgt cgatgtggtg gttgtgccca
3061 cccgggagct ccgtaatagt tggcgccgcc ggggtttcgc ggctttcaca ccccacacag
3121 cggcccgtgt tactaacggc cgccgcgttg tgattgatga ggccccatct ctcccgccac
3181 acctgttgct gctacatatg cagcgggcct cctcggtcca cctactcggt gacccaaatc
3241 agatccctgc tatcgatttt gaacacgccg gcctggtccc cgcgatccgc cccgagcttg
3301 caccaacgag ctggtggcac gtcacacacc gctgcccggc cgatgtgtgc gaactcatac
3361 gcggggccta ccccaaaatc cagaccacga gccgtgtgct acggtccctg tttttggaatg
3421 aaccggctat cggccagaag ttggtttttta cgcaggctgc caaggccgct aaccctggtg
3481 cgattacggt tcacgaagct cagggtgcca ccttcactga gaccacagtt atagccacgg
3541 ccgacgccag gggcctcatt cagtcatccc ggccccatgc tatagttgca cttacccgcc
3601 acaccgagaa gtgcgtcatt ttggatgctc ccggcctgct gcgtgaagtc ggtatctcgg
3661 atgtgattgt caataatttt ttccttgcag gcggagaggt cggccatcac cgcccttctg
3721 tgataccccg cggtaacccc gatcagaacc tcgggacttt acaagccttc ccgccgtcct
3781 gccagattag tgcttaccac cagctggctg aggaattagg ccatcgccct gcccctgttg
3841 ccgccgtctt gccccccttgc cccgagcttg agcagggcct gctttacatg ccacaagagc
3901 ttaccgtgtc tgatagtgtg ctggtttttg agcttacgga catagtccac tgccgcatgg
3961 ccgctccaag ccagcgaaag gctgttcttt caacacttgt ggggcggtat ggccgtagga
4021 cgaagttata tgaggcagca cattcagatg tccgtgagtc cctagccagg ttcatcccca
4081 ctatcgggcc cgttcaggcc accacatgtg agttgtatga gttggttgag gccatggtgg
4141 agaagggtca ggacgggtca gccgtcttag agctagatct ctgcaatcgt gatgtctcgc
4201 gcatcacatt tttccaaaag gattgcaaca agtttacaac tggtgagact atcgcccatg
4261 gcaaggttgg tcagggtata tcggcctgga gcaagacctt ctgcgctttg tttggcccgt
4321 ggttccgtgc cattgagaaa gaaatactgg ccctgctccc gcctaatgtc ttttatggcg
4381 atgcttatga ggagtcagtg tttgctgccg ctgtgtcagg ggcggggtca tgcatggtat
4441 ttgaaaatga cttttcggag tttgatagca cccagaacaa cttctctctc ggccttgagt
4501 gtgtggttat ggaggagtgc ggcatgcctc aatggttaat taggttgtat cacctggtac
4561 ggtcagcctg gattttgcag gcgccaaagg agtctcttaa gggtttytgg aagaagcatt
4621 ctggtgagcc cggtacccctt cttttggaaca ccgtttggaa catggcaatc atagcacatt
4681 gctacgagtt ccgtgacttt cgtgttgctg cctttaaggg tgatgattcg gtggtcctct
4741 gtagcgacta ccggcagagc cgcaatgcgg cagctttgat tgctggctgt gggcttaaat
4801 tgaaggttga ctatcgcccc attgggctgt atgctgggt ggtggtggcc cctggcttgg
4861 ggacactgcc tgatgtggtg cgttttgctg gtcggctgtc tgaaaagaat tggggccccg
4921 gcccggaacg tgctgagcag ctacgtcttg ctgtttgtga tttccttcga gggttgacga
4981 acgttgcgca ggtctgtgtt gatgttgtgt cccgtgtcta tggagttagc cccgggctgg
5041 tacataacct tattggcatg ttgcagacca ttgccgatgg caaggcccac tttacagaga
5101 ctattaaacc tgttcttgat cttacaaatt ccatcataca gcgggtagaa tgaataacat
5161 gtttgttgca tcgcccatgg gatcaccatg cgccctaggg ttgttctgct gctgttcttc
5221 gtgtttctgc ctatgctgcc cgcgccaccg gccggccagc cgtctggccg tcgtcgtggg
```

TABLE OF SEQUENCES-continued

```
5281 cggcgcagcg gcggtgccgg cggtggtttc tggggtgaca gggttgattc tcagcccttc 5341 gccctcccct atattcatcc aaccaacccc ttcgccgccg atgtcgtttc acaatccggg 5401 gctggaactc gccctcggca gccgccccgc cccttggct ccgcttggcg tgaycagtcc 5461 cagcgcccct ccgctgcccc ccgccgtcga tctgccccag ctggggctgc gccgttgact 5521 gctgtatcac cggcccctga cacagcccct gtacctgatg ttgattcacg tggtgctatt 5581 ctgcgtcggc agtataattt gtccacgtcc ccgctcacgt catctgttgc ttcgggtacc 5641 aacttggttc tctacgctgc cccgctaaat ccctcttgc ccctccagga tggcaccaat 5701 acccatatca tggctactga ggcatccaac tatgctcagt atcgggtcgt tcgagctacg 5761 atccgctacc gcccgctggt gccaaatgct gttggtggtt atgctatttc tatttctttt 5821 tggcctcaaa ctacaactac cctacttct gttgatatga attccatcac ttccactgat 5881 gttaggattt tggtccagcc cggtattgcc tccgagttag tcatccctag tgagcgcctt 5941 cattatcgca atcaaggctg gcgctctgtt gagaccacag gtgtggctga ggaggaggct 6001 acctccggtc tggtaatgct ttgcattcat ggctctcctg ttaactctta tactaataca 6061 ccttacactg gtgcgttggg gctccttgat tttgcactag agcttgaatt caggaacttg 6121 acacccggga acaccaacac ccgtgtttcc cggtatacca gcacagcccg ccatcggttg 6181 cgccgcggtg ctgatgggac cgctgagctt actaccacag cagccacacg atttatgaag 6241 gatctgcatt tcactggtac taatggcgtt ggtgaggtgg gtcgcggtat cgccctgaca 6301 ctgttcaatc tcgctgatac gcttctaggt ggtttaccga cagaattgat ttcgtcggct 6361 gggggtcagt tgttctactc ccgccctgtt gtctcggcca atggcgagcc gacagtaaag 6421 ttatacacat ctgtagagaa tgcgcagcaa gacaagggca ttaccatccc acacgatata 6481 gatttgggtg attcccgtgt ggttattcag gattatgata atcagcacga gcaagaccga 6541 cccacgccgt cacctgcccc ctcacgccct ttctcagtcc ttcgcgctaa cgatgttttg 6601 tggctctccc tcactgccgc tgagtacgat cagactacg atgggtcgtc taccaaccct 6661 atgtatgtct ctgatacagt cacctttgtc aatgtggcca ctggtgctca ggctgttgcc 6721 cgctctcttg attggtctaa agttactttg atggtcgcc cccttactac cattcagcag 6781 tattctaaga cattctatgt tctcccgctc cgcgggaagc tgtccttttg ggaggctggc 6841 acaactaggg ccgctacccc atataactat aacaccactg ctagtgatca aattctgatt 6901 gagaatgcgg ccggccatcg tgtcgctatc tccacctaca ctaccagcct gggtgccggt 6961 cctacctcga tctccgcggt gggtgtatta gccccacact cggcccttgc tgttcttgag 7021 gacactgttg attaccctgc tcgtgctcac acttttgatg atttctgccc ggagtgccgt 7081 acctaggtt tgcagggttg tgcattccag tccactattg ctgagcttca gcgccttaaa 7141 atgaaggtag gcaaaacccg ggagtcttaa ttaattcctt tcgtgccccc ttcgcagtct 7201 tcctttckgc tttatttctt atttctgctt cccgcgctcc ctggaaaaaa aaaaaaaaaa 7261 aaaa
```

SEQ ID NO: 6 Kernow C1 ORF1 CDS: 27 . . . 5153
    /codon_start=1
    /product="polyprotein"
    /protein_id="ADV92628.1"
    /db_xref="GI:320005195"
MEAHQFIKAPGITTAIEQAALAAANSALANAVVRPFLSRLQTE

ILINLMQPRQLVFRPEVLWNHPIQRVIHNELEQYCRARAGRCLEVGAHPRSINDNPNV

LHRCFLRPVGRDVQRWYSAPTRGPAANCRRSALRGLPPVDRTYCFDGFSRCAFAAETG

VALYSLHDLWPADVAEAMARHGMTRLYAALHLPPEVLLPPGTYHTTSYLLIHDGDRAV

TABLE OF SEQUENCES-continued

VTYEGDTSAGYNHDVSILRAWIRTTKIVGDHPLVIERVRAIGCHFVLLLTAAPEPSPM

PYVPYPRSTEVYVRSIFGPGGSPSLFPSACSTKSTFHAVPVHIWDRLMLFGATLDDQA

FCCSRLMTYLRGISYKVTVGALVANEGWNASEDALTAVITAAYLTICHQRYLRTQAIS

KGMRRLEVEHAQKFITRLYSWLFEKSGRDYIPGRQLQFYAQCRRWLSAGFHLDPRVLV

FDESVPCRCRTFLKKVAGKFCCFMRWLGQECTCFLEPAEGLVGDHGHDNEAYEGSEVD

QAEPAHLDVSGTYAVHGHQLVALYRALNVPHDIAARASRLTATVELVAGPDRLECRTV

LGNKTFRTTVVDGAHLEANGPEQYVLSFDASRQSMGAGSHNLTYELTPAGLQVRISSN

GLDCTATFPPGGAPSAAPGEVAAFCGALYRYNRFTQRHSLTGGLWLHPEGLLGIFPPF

SPGHIWESANPFCGEGTLYTRTWSTSGFSSDFSPPEAAAPASAAAPGLPHPTPPVSDI

WALPPPSEESQVDAASVPLTLVPAGSPNPIVLPXPPPPPPVRKPSTPPPSRTRRLLYT

YPDGAKVYAGSLFESDCDWLVNASNPGHRPGGGLCHAFHQRFPEAFYWTEFIMREGLA

AYTLTPRPIIHAVAPDYRVEQNPKRLEAAYRETCSRRGTAAYPLLGSGIYQVPVSLSF

DAWERNHRPGDELYLTEPAAAWFEANKPAQPALTITEDTARTANLALEIDAATEVGRA

CAGCTISPGIVHYQFTAGVPGSGKSRSIQQGDVDVVVVPTRELRNSWRRRGFAAFTPH

TAARVTNGRRVVIDEAPSLPPHLLLLHMQRASSVHLLGDPNQIPAIDFEHAGLVPAIR

PELAPTSWWHVTHRCPADVCELIRGAYPKIQTTSRVLRSLFWNEPAIGQKLVFTQAAK

AANPGAITVHEAQGATFTETTVIATADARGLIQSSRAHAIVALTRHTEKCVILDAPGL

LREVGISDVIVNNFFLAGGEVGHHRPSVIPRGNPDQNLGTLQAFPPSCQISAYHQLAE

ELGHRPAPVAAVLPPCPELEQGLLYMPQELTVSDSVLVFELTDIVHCRMAAPSQRKAV

LSTLVGRYGRRTKLYEAAHSDVRESLARFIPTIGPVQATTCELYELVEAMVEKGQDGS

AVLELDLCNRDVSRITFFQKDCNKFTTGETIAHGKVGQGISAWSKTFCALFGPWFRAI

EKEILALLPPNVFYGDAYEESVFAAAVSGAGSCMVFENDFSEFDSTQNNFSLGLECVV

MEECGMPQWLIRLYHLVRSAWILQAPKESLKGFWKKHSGEPGTLLWNTVWNMAIIAHC

YEFRDFRVAAFKGDDSVVLCSDYRQSRNAAALIAGCGLKLKVDYRPIGLYAGVVVAPG

LGTLPDVVRFAGRLSEKNWGPGPERAEQLRLAVCDFLRGLTNVAQVCVDVVSRVYGVS

PGLVHNLIGMLQTIADGKAHFTETIKPVLDLTNSIIQRVE

SEQ ID NO: 7: Kernow C1 HEV ORF3 CDS: 5177 ... 5518
    /codon_start=1
    /product="unknown"
    /protein_id="ADV92630.1"
    /db_xref="GI:320005197"
MGSPCALGLFCCCSSCFCLCCPRHRPASRLAVVVGGAAAVPAVV

SGVTGLILSPSPSPIFIQPTPSPPMSFHNPGLELALGSRPAPLAPLGVXSPSAPPLPP

AVDLPQLGLRR

SEQ ID NO: 8: Kernow C1 HEV ORF2 CDS: 5188 ... 7170
    /codon_start=1
    /product="capsid protein"
    /protein_id="ADV92629.1"
    /db_xref="GI:320005196"
MRPRVVLLLFFVFLPMLPAPPAGQPSGRRRGRRSGGAGGGFWGD

RVDSQPFALPYIHPTNPFAADVVSQSGAGTRPRQPPRPLGSAWRDQSQRPSAAPRRRS

APAGAAPLTAVSPAPDTAPVPDVDSRGAILRRQYNLSTSPLTSSVASGTNLVLYAAPL

NPLLPLQDGTNTHIMATEASNYAQYRVVRATIRYRPLVPNAVGGYAISISFWPQTTTT

PTSVDMNSITSTDVRILVQPGIASELVIPSERLHYRNQGWRSVETTGVAEEEATSGLV

MLCIHGSPVNSYTNTPYTGALGLLDFALELEFRNLTPGNTNTRVSRYTSTARHRLRRG

TABLE OF SEQUENCES-continued

ADGTAELTTTAATRFMKDLHFTGTNGVGEVGRGIALTLFNLADTLLGGLPTELISSAG

GQLFYSRPVVSANGEPTVKLYTSVENAQQDKGITIPHDIDLGDSRVVIQDYDNQHEQD

RPTPSPAPSRPFSVLRANDVLWLSLTAAEYDQTTYGSSTNPMYVSDTVTFVNVATGAQ

AVARSLDWSKVTLDGRPLTTIQQYSKTFYVLPLRGKLSFWEAGTTRAGYPYNYNTTAS

DQILIENAAGHRVAISTYTTSLGAGPTSISAVGVLAPHSALAVLEDTVDYPARAHTFD

DFCPECRTLGLQGCAFQSTIAELQRLKMKVGKTRES

SEQ ID NO: 9 ORF1 insert present in HEV Kernow genotype 3 replicating variant
CYTRLGNDFHTNKRVCEEIAIIPSKKPRNKMAGYVTHLMKRIQRGPVRGISIKLQEEA SEQ ID NO: 10 nucleic acid encoding additional insert in HEV Kernow genotype replicating variant
TGATATTTGGGCGTTACCACCGCCCTCCGAGGAGG--------

TAAAAGACAAAGATGATCTGGGGCCTGACAGATTCTCAACACTCCCAGCCCTAGACTCAGTGCGCAAGCTCAGGT

GGCTGAGGATATTACCATTTAGAAAGAAAGGAAAACAAG-----

AGCAGGTCGATGCAGCATCTGTGCCCCTTACC

What is claimed is:

1. An infectious hepatitis E virus (HEV) type 3 cDNA clone, wherein the infectious clone comprises an insert, relative to the HEV nucleic acid sequence set forth in SEQ ID NO:5, in the region of the nucleic acid sequence that encodes the hypervariable region of ORF1, wherein the insert encodes an in-frame polypeptide sequence of 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65 amino acids in length that has at least 85% identity to SEQ ID NO:9 over its length when maximally aligned to SEQ ID NO:9.

2. The infectious HEV type 3 cDNA clone of claim 1, wherein the insert encodes an in-frame polypeptide sequence that comprises SEQ ID NO:9.

3. The infectious HEV type 3 cDNA clone of claim 1, wherein the insert is positioned in the hypervariable region of ORF1 such that the first amino acid encoded by the insert occurs at position 750 relative to SEQ ID NO:6.

4. An infectious hepatitis E virus (HEV) cDNA clone, wherein the cDNA clone has at least 75% sequence identity to SEQ ID NO:1 and comprises an insert in the region of the nucleic acid sequence that encodes the hypervariable region of ORF1, relative to the HEV nucleic acid sequence set forth in SEQ ID NO:5, wherein the insert encodes an in-frame polypeptide sequence that is 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65 amino acids in length and has at least 85% identity to SEQ ID NO:9 over its length when maximally aligned to SEQ ID NO:9.

5. The HEV cDNA clone of claim 4, wherein the cDNA clone has at least 85% identity, or at least 95% identity, to SEQ ID NO:1; or comprises the nucleic acid sequence of SEQ ID NO:1.

6. The HEV cDNA clone of claim 4, wherein the insert encodes an in-frame polypeptide sequence of 50 to 65 amino acids in length.

7. The HEV cDNA clone of claim 4, wherein the in-frame polypeptide sequence has at least 90% identity, or at least 95% identity, to SEQ ID NO:9.

8. The HEV cDNA clone of claim 4, wherein the in-frame polypeptide sequence comprises SEQ ID NO:9.

9. An infectious genotype 3 or genotype 1 cDNA clone comprising a hepatitis E virus (HEV) nucleic acid sequence, wherein the infectious clone comprises an insert in the region of the nucleic acid sequence that encodes the hypervariable region of ORF1 and wherein the insert encodes an in-frame polypeptide sequence that is 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65 amino acids in length and has at least 85% identity to SEQ ID NO:9 over its length when maximally aligned to SEQ ID NO:9.

10. The cDNA clone of claim 9, wherein the insert in-frame polypeptide sequence has at least 90% identity, or at least 95% identity, to the amino acid sequence set forth in SEQ ID NO:9.

11. The cDNA clone of claim 9, wherein the in-frame amino acid sequence comprises the SEQ ID NO:9.

12. A cell culture system comprising cells that comprise a cDNA clone claim 1.

13. A method of producing a viral composition, the method comprising introducing an RNA obtained from a cDNA clone of claim 1 into cells and obtaining virus produced by the RNA.

14. The method of claim 13, wherein the RNA is introduced into the cells as virus particles.

15. The method of claim 13, wherein the cells are MRC 5 lung cells.

16. A method of producing a viral composition, the method comprising:

introducing an RNA obtained from a cDNA clone of claim 1 into a cell line, wherein the RNA is incapable of producing ORF3; and obtaining virus produced by the RNA.

17. The method of claim 16, wherein the insert encodes an in-frame polypeptide sequence that comprises SEQ ID NO:9.

18. The method of claim 16, wherein the insert is positioned in the hypervariable region of ORF1 such that the first amino acid encoded by the insert occurs at position 750 relative to SEQ ID NO:6.

19. A method of assessing the virus status of a product of interest subjected to a virus treatment process, the method comprising:

adding HEV virus produced using a cDNA clone of claim 1 into the product;

subjecting the product to a virus treatment process that removes and/or inactivates virus present in the product; and determining the level of added virus in the product remaining after or during the virus treatment process.

* * * * *